(12) United States Patent
Gage et al.

(10) Patent No.: US 8,480,757 B2
(45) Date of Patent: Jul. 9, 2013

(54) IMPLANTS AND METHODS FOR REPAIR, REPLACEMENT AND TREATMENT OF DISEASE

(75) Inventors: Gary Gage, Chesterfield, MO (US); H. Davis Adkisson, IV, St. Louis, MO (US); Cheryl R. Blanchard, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 317 days.

(21) Appl. No.: 12/063,291

(22) PCT Filed: Aug. 28, 2006

(86) PCT No.: PCT/US2006/033687
§ 371 (c)(1),
(2), (4) Date: Dec. 10, 2008

(87) PCT Pub. No.: WO2007/025290
PCT Pub. Date: Mar. 1, 2007

(65) Prior Publication Data
US 2009/0143867 A1    Jun. 4, 2009

Related U.S. Application Data

(60) Provisional application No. 60/712,004, filed on Aug. 26, 2005.

(51) Int. Cl.
*A61F 2/28* (2006.01)
(52) U.S. Cl.
USPC ............... 623/23.55; 623/16.11; 623/11.11
(58) Field of Classification Search
USPC .......... 623/23.55–23.59, 23.12–23.14, 11.11, 623/16.11; 424/499
IPC ......................................................... A61F 2/28
See application file for complete search history.

(56) References Cited

U.S. PATENT DOCUMENTS

| | | |
|---|---|---|
| 1,347,622 A | 7/1920 | Deininger |
| 2,533,004 A | 12/1950 | Ferry et al. |

(Continued)

FOREIGN PATENT DOCUMENTS

| | | |
|---|---|---|
| AU | 199871003 B2 | 4/1998 |
| AU | 2006282754 A2 | 8/2006 |

(Continued)

OTHER PUBLICATIONS

Adkisson H.D. et al, In Vitro Generation of Scaffold Independent Neocartilage, Clinical Orthopaedics and Related Research, 2001, pp. S280-S294, No. 391S.

(Continued)

*Primary Examiner* — Thomas Sweet
*Assistant Examiner* — Jason-Dennis Stewart
(74) *Attorney, Agent, or Firm* — Schwegman, Lundberg & Woessner P.A.

(57) ABSTRACT

Implants comprising cartilage and trabecular metal, and methods of making the implants are disclosed. Further disclosed are therapeutic uses of the implants, which include methods of treatment or repair of an chondral or osteochondral defect, such as a chondral or osteochondral injury, lesion or disease. An implant comprises cartilage or chondrocytes and a subchondral base comprising trabecular metal. An implant can comprise a geometric shape such as a cylinder or an anatomical shape such as a condyle, and can be used in conjunction with a positioning structure.

42 Claims, 8 Drawing Sheets

U.S. PATENT DOCUMENTS

| | | | |
|---|---|---|---|
| 2,621,145 A | 12/1952 | Sano | |
| 3,400,199 A | 9/1968 | Balassa | |
| 3,476,855 A | 11/1969 | Balassa | |
| 3,478,146 A | 11/1969 | Balassa | |
| 3,772,432 A | 11/1973 | Balassa | |
| RE28,093 E | 7/1974 | Balassa | |
| 3,966,908 A | 6/1976 | Balassa | |
| 4,440,680 A | 4/1984 | Cioca | |
| 4,453,939 A | 6/1984 | Zimmerman et al. | |
| 4,479,271 A | 10/1984 | Bolesky et al. | |
| 4,522,096 A | 6/1985 | Niven, Jr. | |
| 4,566,138 A | 1/1986 | Lewis et al. | |
| 4,587,766 A | 5/1986 | Miyatake et al. | |
| 4,609,551 A | 9/1986 | Caplan et al. | |
| 4,627,879 A | 12/1986 | Rose et al. | |
| 4,640,834 A | 2/1987 | Eibl et al. | |
| 4,641,651 A * | 2/1987 | Card | 606/184 |
| 4,642,120 A | 2/1987 | Nevo et al. | |
| 4,656,137 A | 4/1987 | Balassa | |
| 4,660,755 A | 4/1987 | Farling et al. | |
| 4,714,457 A | 12/1987 | Alterbaum | |
| 4,773,418 A | 9/1988 | Hettich | |
| 4,818,633 A | 4/1989 | Dinwoodie et al. | |
| 4,846,835 A | 7/1989 | Grande | |
| 4,851,354 A | 7/1989 | Winston et al. | |
| 4,863,474 A | 9/1989 | Brown et al. | |
| 4,863,475 A | 9/1989 | Andersen et al. | |
| 4,904,259 A | 2/1990 | Itay | |
| 4,911,720 A * | 3/1990 | Collier | 623/23.12 |
| 4,928,603 A | 5/1990 | Rose et al. | |
| 4,952,403 A | 8/1990 | Vallee et al. | |
| 4,963,489 A | 10/1990 | Naughton et al. | |
| 4,997,444 A | 3/1991 | Farling | |
| 4,997,445 A | 3/1991 | Hodorek | |
| 5,002,071 A | 3/1991 | Harrell | |
| 5,002,582 A | 3/1991 | Guire et al. | |
| 5,013,324 A | 5/1991 | Zolman et al. | |
| 5,018,285 A | 5/1991 | Zolman et al. | |
| 5,030,215 A | 7/1991 | Morse et al. | |
| 5,032,508 A | 7/1991 | Naughton et al. | |
| 5,041,138 A | 8/1991 | Vacanti et al. | |
| 5,053,050 A | 10/1991 | Itay | |
| 5,067,963 A | 11/1991 | Khouri et al. | |
| 5,067,964 A | 11/1991 | Richmond et al. | |
| 5,069,881 A | 12/1991 | Clarkin | |
| 5,080,674 A | 1/1992 | Jacobs et al. | |
| 5,092,887 A | 3/1992 | Gendler | |
| 5,130,418 A | 7/1992 | Thompson | |
| 5,139,527 A | 8/1992 | Redl et al. | |
| 5,189,148 A | 2/1993 | Akiyama et al. | |
| 5,198,308 A | 3/1993 | Shetty et al. | |
| 5,206,023 A | 4/1993 | Hunziker | |
| 5,217,954 A | 6/1993 | Foster et al. | |
| 5,219,363 A | 6/1993 | Crowninshield et al. | |
| 5,226,914 A | 7/1993 | Caplan et al. | |
| 5,236,457 A | 8/1993 | Devanathan | |
| 5,254,471 A | 10/1993 | Mori et al. | |
| 5,269,785 A | 12/1993 | Bonutti | |
| 5,270,300 A | 12/1993 | Hunziker | |
| 5,281,422 A | 1/1994 | Badylak et al. | |
| 5,282,861 A | 2/1994 | Kaplan | |
| 5,290,552 A | 3/1994 | Sierra et al. | |
| 5,290,558 A | 3/1994 | O'Leary et al. | |
| 5,312,417 A | 5/1994 | Wilk | |
| 5,323,954 A | 6/1994 | Shetty et al. | |
| 5,326,357 A | 7/1994 | Kandel | |
| 5,345,927 A | 9/1994 | Bonutti | |
| 5,356,629 A | 10/1994 | Sander et al. | |
| 5,368,858 A | 11/1994 | Hunziker | |
| 5,372,821 A | 12/1994 | Badylak et al. | |
| 5,387,243 A | 2/1995 | Devanathan | |
| 5,403,317 A | 4/1995 | Bonutti | |
| 5,405,607 A | 4/1995 | Epstein | |
| 5,410,016 A | 4/1995 | Hubbell et al. | |
| 5,443,454 A | 8/1995 | Tanabe et al. | |
| 5,443,510 A | 8/1995 | Shetty et al. | |
| 5,443,512 A | 8/1995 | Parr et al. | |
| 5,445,833 A | 8/1995 | Badylak et al. | |
| 5,456,723 A | 10/1995 | Steinemann et al. | |
| 5,456,828 A | 10/1995 | Tersi et al. | |
| 5,461,953 A | 10/1995 | McCormick | |
| 5,475,052 A | 12/1995 | Rhee et al. | |
| 5,482,929 A | 1/1996 | Fukunaga et al. | |
| 5,496,375 A | 3/1996 | Sisk et al. | |
| 5,504,300 A | 4/1996 | Devanathan et al. | |
| 5,510,396 A | 4/1996 | Prewett et al. | |
| 5,514,536 A | 5/1996 | Taylor | |
| 5,516,532 A | 5/1996 | Atala et al. | |
| 5,516,533 A | 5/1996 | Badylak et al. | |
| 5,535,810 A | 7/1996 | Compton et al. | |
| 5,545,222 A | 8/1996 | Bonutti | |
| 5,549,704 A * | 8/1996 | Sutter | 623/23.13 |
| 5,549,904 A | 8/1996 | Juergensen et al. | |
| 5,554,389 A | 9/1996 | Badylak et al. | |
| 5,556,429 A | 9/1996 | Felt | |
| 5,565,519 A | 10/1996 | Rhee et al. | |
| 5,571,187 A | 11/1996 | Devanathan | |
| 5,577,517 A | 11/1996 | Bonutti | |
| 5,578,492 A | 11/1996 | Fedun | |
| 5,585,007 A | 12/1996 | Antanavich et al. | |
| 5,605,887 A | 2/1997 | Pines et al. | |
| 5,612,028 A | 3/1997 | Sackier et al. | |
| 5,618,925 A | 4/1997 | Dupont et al. | |
| 5,624,463 A | 4/1997 | Stone et al. | |
| 5,639,280 A | 6/1997 | Warner et al. | |
| 5,643,192 A | 7/1997 | Hirsh et al. | |
| 5,650,494 A | 7/1997 | Cerletti et al. | |
| 5,654,166 A | 8/1997 | Kurth | |
| 5,655,546 A | 8/1997 | Halpern | |
| 5,656,587 A | 8/1997 | Sporn et al. | |
| 5,662,710 A | 9/1997 | Bonutti | |
| 5,669,544 A | 9/1997 | Schulze et al. | |
| 5,672,284 A | 9/1997 | Devanathan et al. | |
| 5,673,840 A | 10/1997 | Schulze et al. | |
| 5,673,841 A | 10/1997 | Schulze et al. | |
| 5,680,982 A | 10/1997 | Schulze et al. | |
| 5,681,353 A | 10/1997 | Li et al. | |
| 5,692,668 A | 12/1997 | Schulze et al. | |
| 5,694,951 A | 12/1997 | Bonutti | |
| 5,695,998 A | 12/1997 | Badylak et al. | |
| 5,709,854 A | 1/1998 | Griffith-Cima et al. | |
| 5,713,374 A | 2/1998 | Pachence et al. | |
| 5,714,371 A | 2/1998 | Ramanathan et al. | |
| 5,723,010 A | 3/1998 | Yui et al. | |
| 5,723,011 A | 3/1998 | Devanathan et al. | |
| 5,723,331 A | 3/1998 | Tubo et al. | |
| 5,734,959 A | 3/1998 | Krebs et al. | |
| 5,735,875 A | 4/1998 | Bonutti et al. | |
| 5,736,132 A | 4/1998 | Juergensen et al. | |
| 5,736,396 A | 4/1998 | Bruder et al. | |
| 5,749,968 A | 5/1998 | Melanson et al. | |
| 5,753,485 A | 5/1998 | Dwulet et al. | |
| 5,755,791 A | 5/1998 | Whitson et al. | |
| 5,769,899 A | 6/1998 | Schwartz et al. | |
| 5,770,194 A | 6/1998 | Edwardson et al. | |
| 5,782,835 A | 7/1998 | Hart et al. | |
| 5,782,915 A | 7/1998 | Stone | |
| 5,786,217 A | 7/1998 | Tubo et al. | |
| 5,788,662 A | 8/1998 | Antanavich et al. | |
| 5,795,571 A | 8/1998 | Cederholm-Williams et al. | |
| 5,795,780 A | 8/1998 | Cederholm-Williams et al. | |
| 5,811,094 A | 9/1998 | Caplan et al. | |
| 5,824,093 A | 10/1998 | Ray et al. | |
| 5,826,776 A | 10/1998 | Schulze et al. | |
| 5,827,217 A | 10/1998 | Silver et al. | |
| 5,830,741 A | 11/1998 | Dwulet et al. | |
| 5,842,477 A | 12/1998 | Naughton et al. | |
| 5,853,746 A | 12/1998 | Hunziker | |
| 5,853,976 A | 12/1998 | Hesse et al. | |
| 5,864,016 A | 1/1999 | Eibl et al. | |
| 5,866,415 A | 2/1999 | Villeneuve | |
| 5,866,630 A | 2/1999 | Mitra et al. | |
| 5,876,208 A | 3/1999 | Mitra et al. | |
| 5,876,451 A | 3/1999 | Yui et al. | |
| 5,876,452 A | 3/1999 | Athanasiou et al. | |
| 5,879,398 A | 3/1999 | Swarts et al. | |
| 5,888,219 A | 3/1999 | Bonutti | |

| Patent | Kind | Date | Inventors |
|---|---|---|---|
| 5,888,491 | A | 3/1999 | Mitra et al. |
| 5,890,898 | A | 4/1999 | Wada et al. |
| 5,891,455 | A | 4/1999 | Sittinger et al. |
| 5,899,936 | A | 5/1999 | Goldstein |
| 5,902,741 | A | 5/1999 | Purchio et al. |
| 5,919,702 | A | 7/1999 | Purchio et al. |
| 5,921,987 | A | 7/1999 | Stone |
| 5,922,027 | A | 7/1999 | Stone |
| 5,922,846 | A | 7/1999 | Cerletti et al. |
| 5,926,685 | A | 7/1999 | Krebs et al. |
| 5,928,945 | A | 7/1999 | Seliktar et al. |
| 5,935,131 | A | 8/1999 | Bonutti |
| 5,944,754 | A | 8/1999 | Vacanti |
| 5,944,755 | A | 8/1999 | Stone |
| 5,948,384 | A | 9/1999 | Filler |
| 5,952,215 | A | 9/1999 | Dwulet et al. |
| 5,962,405 | A | 10/1999 | Seelich |
| 5,964,752 | A | 10/1999 | Stone |
| 5,964,805 | A | 10/1999 | Stone |
| 5,968,556 | A | 10/1999 | Atala et al. |
| 5,985,315 | A | 11/1999 | Patat et al. |
| 5,989,269 | A | 11/1999 | Vibe-Hansen et al. |
| 5,989,888 | A | 11/1999 | Dwulet et al. |
| 6,022,361 | A | 2/2000 | Epstein et al. |
| 6,025,334 | A | 2/2000 | Dupont et al. |
| 6,041,723 | A | 3/2000 | Peterson |
| 6,045,990 | A | 4/2000 | Baust et al. |
| 6,048,966 | A | 4/2000 | Edwardson et al. |
| 6,051,249 | A | 4/2000 | Samuelsen |
| 6,059,198 | A | 5/2000 | Moroi et al. |
| 6,060,053 | A | 5/2000 | Atala |
| 6,077,989 | A | 6/2000 | Kandel et al. |
| 6,080,194 | A | 6/2000 | Pachence et al. |
| 6,080,579 | A | 6/2000 | Hanley, Jr. et al. |
| 6,083,383 | A | 7/2000 | Huang et al. |
| 6,087,553 | A | 7/2000 | Cohen et al. |
| 6,107,085 | A | 8/2000 | Coughlin et al. |
| 6,110,209 | A | 8/2000 | Stone |
| 6,110,210 | A | 8/2000 | Norton et al. |
| 6,110,212 | A | 8/2000 | Gregory |
| 6,110,482 | A | 8/2000 | Khouri et al. |
| 6,120,514 | A | 9/2000 | Vibe-Hansen et al. |
| 6,129,761 | A | 10/2000 | Hubbell |
| 6,132,465 | A | 10/2000 | Ray et al. |
| 6,132,472 | A | 10/2000 | Bonutti |
| 6,140,123 | A | 10/2000 | Demetriou et al. |
| 6,140,452 | A | 10/2000 | Felt et al. |
| 6,143,214 | A | 11/2000 | Barlow |
| 6,150,163 | A | 11/2000 | McPherson et al. |
| 6,152,142 | A | 11/2000 | Tseng |
| 6,162,241 | A | 12/2000 | Coury et al. |
| 6,171,610 | B1 | 1/2001 | Vacanti et al. |
| 6,174,313 | B1 | 1/2001 | Bonutti |
| 6,179,871 | B1 | 1/2001 | Halpern |
| 6,183,737 | B1 | 2/2001 | Zaleske et al. |
| 6,187,329 | B1 | 2/2001 | Agrawal et al. |
| 6,200,330 | B1 | 3/2001 | Benderev et al. |
| 6,203,526 | B1 | 3/2001 | McBeth et al. |
| 6,224,893 | B1 | 5/2001 | Langer et al. |
| 6,235,316 | B1 | 5/2001 | Adkisson |
| 6,242,247 | B1 | 6/2001 | Rieser et al. |
| 6,248,114 | B1 | 6/2001 | Ysebaert |
| 6,264,659 | B1 | 7/2001 | Ross et al. |
| 6,271,320 | B1 | 8/2001 | Keller et al. |
| 6,274,090 | B1 | 8/2001 | Coelho et al. |
| 6,280,993 | B1 | 8/2001 | Yamato et al. |
| 6,294,656 | B1 | 9/2001 | Mittl et al. |
| 6,306,169 | B1 | 10/2001 | Lee et al. |
| 6,306,177 | B1 | 10/2001 | Felt et al. |
| 6,312,668 | B2 | 11/2001 | Mitra et al. |
| 6,322,563 | B1 | 11/2001 | Cummings et al. |
| 6,327,257 | B1 | 12/2001 | Khalifa |
| 6,336,930 | B1 | 1/2002 | Stalcup et al. |
| 6,338,878 | B1 | 1/2002 | Overton et al. |
| 6,358,266 | B1 | 3/2002 | Bonutti |
| 6,361,565 | B1 | 3/2002 | Bonutti |
| 6,368,298 | B1 | 4/2002 | Beretta et al. |
| 6,368,784 | B1 | 4/2002 | Murray |
| 6,370,920 | B1 | 4/2002 | Overton et al. |
| 6,378,527 | B1 | 4/2002 | Hungerford et al. |
| 6,395,327 | B1 | 5/2002 | Shetty |
| 6,417,320 | B1 | 7/2002 | Otto et al. |
| 6,423,063 | B1 | 7/2002 | Bonutti |
| 6,425,704 | B2 | 7/2002 | Voiers et al. |
| 6,436,143 | B1 | 8/2002 | Ross et al. |
| 6,437,018 | B1 | 8/2002 | Gertzman et al. |
| 6,443,988 | B2 | 9/2002 | Felt et al. |
| 6,444,228 | B1 | 9/2002 | Baugh et al. |
| 6,447,514 | B1 | 9/2002 | Stalcup et al. |
| 6,464,713 | B2 | 10/2002 | Bonutti |
| 6,468,289 | B1 | 10/2002 | Bonutti |
| 6,468,527 | B2 | 10/2002 | Austin et al. |
| 6,472,162 | B1 | 10/2002 | Coelho et al. |
| 6,475,764 | B1 | 11/2002 | Burtscher et al. |
| 6,482,235 | B1 | 11/2002 | Lambrecht et al. |
| 6,485,723 | B1 | 11/2002 | Badylak et al. |
| 6,492,163 | B1 | 12/2002 | Yoo et al. |
| 6,497,903 | B1 | 12/2002 | Hennink et al. |
| 6,503,267 | B2 | 1/2003 | Bonutti et al. |
| 6,503,277 | B2 | 1/2003 | Bonutti |
| 6,504,079 | B2 | 1/2003 | Tucker et al. |
| 6,511,958 | B1 | 1/2003 | Atkinson et al. |
| 6,514,514 | B1 | 2/2003 | Atkinson et al. |
| 6,514,522 | B2 | 2/2003 | Domb |
| 6,528,052 | B1 | 3/2003 | Smith et al. |
| 6,533,817 | B1 | 3/2003 | Norton et al. |
| 6,534,084 | B1 | 3/2003 | Vyakarnam et al. |
| 6,534,591 | B2 | 3/2003 | Rhee et al. |
| 6,543,455 | B2 | 4/2003 | Bonutti |
| 6,544,472 | B1 | 4/2003 | Compton et al. |
| 6,551,355 | B1 * | 4/2003 | Lewandrowski et al. .. 623/16.11 |
| 6,559,119 | B1 | 5/2003 | Burgess et al. |
| 6,575,982 | B1 | 6/2003 | Bonutti |
| 6,576,265 | B1 | 6/2003 | Spievack |
| 6,579,538 | B1 | 6/2003 | Spievack |
| 6,582,960 | B1 | 6/2003 | Martin et al. |
| 6,592,531 | B2 | 7/2003 | Bonutti |
| 6,596,180 | B2 | 7/2003 | Baugh et al. |
| 6,599,515 | B1 | 7/2003 | Delmotte |
| 6,607,534 | B2 | 8/2003 | Bonutti |
| 6,610,033 | B1 | 8/2003 | Melanson et al. |
| 6,620,169 | B1 | 9/2003 | Peterson et al. |
| 6,626,859 | B2 | 9/2003 | Von Segesser |
| 6,626,945 | B2 | 9/2003 | Simon et al. |
| 6,626,950 | B2 | 9/2003 | Brown et al. |
| 6,630,000 | B1 | 10/2003 | Bonutti |
| 6,632,246 | B1 | 10/2003 | Simon et al. |
| 6,632,648 | B1 | 10/2003 | Kampinga et al. |
| 6,637,437 | B1 | 10/2003 | Hungerford et al. |
| 6,638,309 | B2 | 10/2003 | Bonutti |
| 6,645,316 | B1 | 11/2003 | Brouwer et al. |
| 6,645,764 | B1 | 11/2003 | Adkisson |
| 6,649,168 | B2 | 11/2003 | Arvinte et al. |
| 6,652,532 | B2 | 11/2003 | Bonutti |
| 6,652,872 | B2 | 11/2003 | Nevo et al. |
| 6,652,883 | B2 | 11/2003 | Goupil et al. |
| 6,653,062 | B1 | 11/2003 | DePablo et al. |
| 6,662,805 | B2 | 12/2003 | Frondoza et al. |
| 6,663,616 | B1 | 12/2003 | Roth et al. |
| 6,676,971 | B2 | 1/2004 | Goupil et al. |
| 6,685,987 | B2 | 2/2004 | Shetty |
| 6,697,143 | B2 | 2/2004 | Freeman |
| 6,705,790 | B2 | 3/2004 | Quintero et al. |
| 6,713,772 | B2 | 3/2004 | Goodman et al. |
| 6,719,803 | B2 | 4/2004 | Bonutti |
| 6,719,901 | B2 | 4/2004 | Dolecek et al. |
| 6,730,299 | B1 | 5/2004 | Tayot et al. |
| 6,733,515 | B1 | 5/2004 | Edwards et al. |
| 6,736,853 | B2 | 5/2004 | Bonutti |
| 6,737,072 | B1 | 5/2004 | Angele et al. |
| 6,740,186 | B2 | 5/2004 | Hawkins et al. |
| 6,743,232 | B2 | 6/2004 | Overaker et al. |
| 6,773,458 | B1 | 8/2004 | Brauker et al. |
| 6,773,713 | B2 | 8/2004 | Bonassar et al. |
| 6,776,938 | B2 | 8/2004 | Bonutti |
| 6,797,006 | B2 | 9/2004 | Hodorek |
| 6,800,663 | B2 | 10/2004 | Asgarzadeh et al. |
| 6,818,008 | B1 | 11/2004 | Cates et al. |

| | | |
|---|---|---|
| 6,830,762 B2 | 12/2004 | Baugh et al. |
| 6,833,408 B2 | 12/2004 | Sehl et al. |
| 6,835,198 B2 | 12/2004 | Bonutti |
| 6,835,277 B2 | 12/2004 | Park |
| 6,840,960 B2 | 1/2005 | Bubb |
| 6,852,330 B2 | 2/2005 | Bowman et al. |
| 6,860,904 B2 | 3/2005 | Bonutti |
| 6,884,428 B2 | 4/2005 | Binette et al. |
| 6,886,568 B2 | 5/2005 | Frondoza et al. |
| 6,893,466 B2 | 5/2005 | Trieu |
| 6,905,517 B2 | 6/2005 | Bonutti |
| 6,919,067 B2 | 7/2005 | Filler et al. |
| 6,919,172 B2 | 7/2005 | DePablo et al. |
| 6,921,633 B2 | 7/2005 | Baust et al. |
| 6,942,880 B1 | 9/2005 | Dolecek |
| 6,949,252 B2 | 9/2005 | Mizuno et al. |
| 6,965,014 B1 | 11/2005 | Delmotte et al. |
| 6,979,307 B2 | 12/2005 | Beretta et al. |
| 6,990,982 B1 | 1/2006 | Bonutti |
| 6,991,652 B2 | 1/2006 | Burg |
| 7,009,039 B2 | 3/2006 | Yayon et al. |
| 7,045,601 B2 | 5/2006 | Metzner et al. |
| 7,067,123 B2 | 6/2006 | Gomes et al. |
| 7,081,125 B2 | 7/2006 | Edwards et al. |
| 7,083,964 B2 | 8/2006 | Kurfurst et al. |
| 7,087,227 B2 | 8/2006 | Adkisson |
| RE39,321 E | 10/2006 | MacPhee et al. |
| 7,134,437 B2 | 11/2006 | Bonutti |
| 7,147,471 B2 | 12/2006 | Frey et al. |
| 7,217,294 B2 | 5/2007 | Kusanagi et al. |
| 7,235,255 B2 | 6/2007 | Austin et al. |
| 7,273,756 B2 | 9/2007 | Adkisson et al. |
| 7,276,235 B2 | 10/2007 | Metzner et al. |
| 7,276,481 B2 | 10/2007 | Golembo et al. |
| 7,299,805 B2 | 11/2007 | Bonutti |
| 7,316,822 B2 | 1/2008 | Binette et al. |
| 7,375,077 B2 | 5/2008 | Mao |
| 7,468,192 B2 | 12/2008 | Mizuno et al. |
| 7,488,348 B2 | 2/2009 | Truncale et al. |
| 7,537,780 B2 | 5/2009 | Mizuno et al. |
| 7,720,533 B2 | 5/2010 | Behravesh et al. |
| 7,824,711 B2 | 11/2010 | Kizer et al. |
| 7,838,040 B2 | 11/2010 | Malinin |
| 7,875,296 B2 | 1/2011 | Binette et al. |
| 7,879,604 B2 | 2/2011 | Seyedin et al. |
| RE42,208 E | 3/2011 | Truncale et al. |
| 7,897,384 B2 | 3/2011 | Binette et al. |
| 7,901,457 B2 | 3/2011 | Truncale et al. |
| 7,901,461 B2 | 3/2011 | Harmon et al. |
| 8,017,394 B2 | 9/2011 | Adkisson, IV et al. |
| 8,025,901 B2 | 9/2011 | Kao et al. |
| 8,137,702 B2 | 3/2012 | Binette et al. |
| 8,163,549 B2 | 4/2012 | Yao et al. |
| 2001/0006634 A1 | 7/2001 | Zaleske et al. |
| 2001/0014473 A1 | 8/2001 | Rieser et al. |
| 2001/0014475 A1 | 8/2001 | Frondoza et al. |
| 2001/0051834 A1 | 12/2001 | Frondoza et al. |
| 2001/0055621 A1 | 12/2001 | Baugh et al. |
| 2002/0004038 A1 | 1/2002 | Baugh et al. |
| 2002/0009805 A1 | 1/2002 | Nevo et al. |
| 2002/0012705 A1 | 1/2002 | Domb |
| 2002/0028192 A1 | 3/2002 | Dimitrijevich et al. |
| 2002/0029055 A1 | 3/2002 | Bonutti |
| 2002/0045940 A1 | 4/2002 | Giannetti et al. |
| 2002/0055755 A1 | 5/2002 | Bonutti |
| 2002/0062151 A1 | 5/2002 | Altman et al. |
| 2002/0064512 A1 | 5/2002 | Petersen et al. |
| 2002/0082623 A1 | 6/2002 | Osther et al. |
| 2002/0095160 A1 | 7/2002 | Bonutti |
| 2002/0099401 A1 | 7/2002 | Bonutti |
| 2002/0099448 A1 | 7/2002 | Hiles et al. |
| 2002/0106625 A1 | 8/2002 | Hung et al. |
| 2002/0123142 A1 | 9/2002 | Hungerford et al. |
| 2002/0128683 A1 | 9/2002 | Epstein |
| 2002/0133235 A1 | 9/2002 | Hungerford et al. |
| 2002/0150550 A1 | 10/2002 | Petersen |
| 2002/0151974 A1 | 10/2002 | Bonassar et al. |
| 2002/0159982 A1 | 10/2002 | Bonassar et al. |
| 2002/0159985 A1 | 10/2002 | Baugh et al. |
| 2002/0183850 A1 | 12/2002 | Felt et al. |
| 2002/0198490 A1 | 12/2002 | Wirt et al. |
| 2002/0198599 A1 | 12/2002 | Haldimann |
| 2003/0009147 A1 | 1/2003 | Bonutti |
| 2003/0009235 A1 | 1/2003 | Manrique et al. |
| 2003/0039695 A1 | 2/2003 | Geistlich et al. |
| 2003/0040113 A1 | 2/2003 | Mizuno et al. |
| 2003/0065389 A1 | 4/2003 | Petersen |
| 2003/0069605 A1 | 4/2003 | Bonutti et al. |
| 2003/0077244 A1 | 4/2003 | Petersen |
| 2003/0099620 A1 | 5/2003 | Zaleske et al. |
| 2003/0114936 A1* | 6/2003 | Sherwood et al. ......... 623/23.58 |
| 2003/0134032 A1 | 7/2003 | Chaouk et al. |
| 2003/0151974 A1 | 8/2003 | Kutty et al. |
| 2003/0153078 A1 | 8/2003 | Libera et al. |
| 2003/0176602 A1 | 9/2003 | Schmidt et al. |
| 2003/0181939 A1 | 9/2003 | Bonutti |
| 2003/0187387 A1 | 10/2003 | Wirt et al. |
| 2003/0195628 A1 | 10/2003 | Bao et al. |
| 2003/0211073 A1 | 11/2003 | Goupil et al. |
| 2003/0223956 A1 | 12/2003 | Goupil et al. |
| 2004/0030404 A1 | 2/2004 | Noll et al. |
| 2004/0030406 A1 | 2/2004 | Ochi et al. |
| 2004/0033212 A1 | 2/2004 | Thomson et al. |
| 2004/0042960 A1 | 3/2004 | Frey et al. |
| 2004/0044408 A1 | 3/2004 | Hungerford et al. |
| 2004/0048796 A1 | 3/2004 | Hariri et al. |
| 2004/0059416 A1 | 3/2004 | Murray et al. |
| 2004/0064192 A1 | 4/2004 | Bubb |
| 2004/0064193 A1 | 4/2004 | Evans et al. |
| 2004/0073308 A1 | 4/2004 | Kuslich et al. |
| 2004/0078073 A1 | 4/2004 | Bonutti |
| 2004/0078077 A1 | 4/2004 | Binette et al. |
| 2004/0078090 A1 | 4/2004 | Binette et al. |
| 2004/0092946 A1 | 5/2004 | Bagga et al. |
| 2004/0097714 A1 | 5/2004 | Maubois et al. |
| 2004/0097829 A1 | 5/2004 | McRury et al. |
| 2004/0117033 A1 | 6/2004 | Frondoza et al. |
| 2004/0127987 A1 | 7/2004 | Evans et al. |
| 2004/0134502 A1 | 7/2004 | Mizuno et al. |
| 2004/0138522 A1 | 7/2004 | Haarstad et al. |
| 2004/0151705 A1 | 8/2004 | Mizuno et al. |
| 2004/0172045 A1 | 9/2004 | Eriksson et al. |
| 2004/0175690 A1 | 9/2004 | Mishra et al. |
| 2004/0176787 A1 | 9/2004 | Mishra et al. |
| 2004/0181240 A1 | 9/2004 | Tseng et al. |
| 2004/0191900 A1 | 9/2004 | Mizuno et al. |
| 2004/0193181 A1 | 9/2004 | Bonutti |
| 2004/0219182 A1 | 11/2004 | Gomes et al. |
| 2004/0228901 A1 | 11/2004 | Trieu et al. |
| 2004/0230303 A1 | 11/2004 | Gomes et al. |
| 2004/0230309 A1 | 11/2004 | DiMauro et al. |
| 2005/0026133 A1 | 2/2005 | Nakatsuji et al. |
| 2005/0038520 A1 | 2/2005 | Binette et al. |
| 2005/0043805 A1 | 2/2005 | Chudik |
| 2005/0043814 A1 | 2/2005 | Kusanagi et al. |
| 2005/0054595 A1 | 3/2005 | Binette et al. |
| 2005/0064042 A1 | 3/2005 | Vunjak-Novakovic et al. |
| 2005/0079159 A1 | 4/2005 | Shastri et al. |
| 2005/0095235 A1 | 5/2005 | Austin et al. |
| 2005/0095666 A1 | 5/2005 | Jhavar et al. |
| 2005/0113736 A1 | 5/2005 | Orr et al. |
| 2005/0113937 A1 | 5/2005 | Binette et al. |
| 2005/0119754 A1 | 6/2005 | Trieu et al. |
| 2005/0124038 A1 | 6/2005 | Aguiar et al. |
| 2005/0125077 A1 | 6/2005 | Harmon et al. |
| 2005/0136046 A1 | 6/2005 | Pines et al. |
| 2005/0137600 A1 | 6/2005 | Jacobs et al. |
| 2005/0139656 A1 | 6/2005 | Arnouse |
| 2005/0152882 A1* | 7/2005 | Kizer et al. ................. 424/93.7 |
| 2005/0152886 A1 | 7/2005 | Baugh et al. |
| 2005/0152961 A1 | 7/2005 | Austin et al. |
| 2005/0171470 A1 | 8/2005 | Kucklick et al. |
| 2005/0175657 A1 | 8/2005 | Hunter et al. |
| 2005/0175704 A1 | 8/2005 | Petersen |
| 2005/0175711 A1 | 8/2005 | Kralovee et al. |
| 2005/0177249 A1 | 8/2005 | Kladakis et al. |
| 2005/0186247 A1 | 8/2005 | Hunter et al. |
| 2005/0186283 A1 | 8/2005 | Geistlich et al. |

| | | |
|---|---|---|
| 2005/0186673 A1 | 8/2005 | Geistlich et al. |
| 2005/0192532 A1 | 9/2005 | Kucklick et al. |
| 2005/0196387 A1 | 9/2005 | Seyedin et al. |
| 2005/0196460 A1 | 9/2005 | Malinin |
| 2005/0203342 A1 | 9/2005 | Kucklick et al. |
| 2005/0209601 A1 | 9/2005 | Bowman et al. |
| 2005/0209602 A1 | 9/2005 | Bowman et al. |
| 2005/0222687 A1 | 10/2005 | Vunjak-Novakovic et al. |
| 2005/0226856 A1 | 10/2005 | Ahlfors |
| 2005/0234298 A1 | 10/2005 | Kucklick et al. |
| 2005/0234485 A1 | 10/2005 | Seegert et al. |
| 2005/0244454 A1 | 11/2005 | Elson et al. |
| 2005/0250697 A1 | 11/2005 | Maubois et al. |
| 2005/0250698 A1 | 11/2005 | Maubois et al. |
| 2005/0251268 A1 | 11/2005 | Truncale |
| 2005/0265980 A1 | 12/2005 | Chen et al. |
| 2005/0267584 A1 * | 12/2005 | Burdulis et al. ............ 623/20.19 |
| 2005/0273129 A1 | 12/2005 | Michels et al. |
| 2005/0287218 A1 | 12/2005 | Chaouk et al. |
| 2005/0288796 A1 | 12/2005 | Awad et al. |
| 2006/0008530 A1 | 1/2006 | Seyedin et al. |
| 2006/0009779 A1 | 1/2006 | Collins et al. |
| 2006/0019389 A1 | 1/2006 | Yayon et al. |
| 2006/0024373 A1 | 2/2006 | Shahar et al. |
| 2006/0024826 A1 | 2/2006 | Bonassar et al. |
| 2006/0029679 A1 | 2/2006 | Dolecek |
| 2006/0041270 A1 | 2/2006 | Lenker et al. |
| 2006/0073588 A1 | 4/2006 | Adkisson et al. |
| 2006/0078872 A1 | 4/2006 | Taguchi et al. |
| 2006/0099706 A1 | 5/2006 | Massey et al. |
| 2006/0111738 A1 | 5/2006 | Wenchell |
| 2006/0111778 A1 | 5/2006 | Michalow |
| 2006/0128016 A1 | 6/2006 | Tokushima et al. |
| 2006/0134093 A1 | 6/2006 | Ronfard |
| 2006/0134094 A2 | 6/2006 | Delmotte et al. |
| 2006/0147547 A1 | 7/2006 | Yayon |
| 2006/0153815 A1 | 7/2006 | Seyda et al. |
| 2006/0183224 A1 | 8/2006 | Aerts et al. |
| 2006/0195188 A1 | 8/2006 | ODriscoll et al. |
| 2006/0210643 A1 | 9/2006 | Truncale et al. |
| 2006/0216822 A1 | 9/2006 | Mizuno et al. |
| 2006/0228391 A1 | 10/2006 | Seyedin et al. |
| 2006/0240064 A9 | 10/2006 | Hunter et al. |
| 2006/0240555 A1 | 10/2006 | Ronfard |
| 2006/0251631 A1 | 11/2006 | Adkisson, IV et al. |
| 2006/0264966 A1 | 11/2006 | Armstrong |
| 2006/0275273 A1 | 12/2006 | Seyedin et al. |
| 2006/0281173 A1 | 12/2006 | Fukuda et al. |
| 2006/0292131 A1 | 12/2006 | Binette et al. |
| 2007/0014867 A1 | 1/2007 | Kusanagi et al. |
| 2007/0031471 A1 | 2/2007 | Peyman |
| 2007/0038299 A1 | 2/2007 | Stone et al. |
| 2007/0041952 A1 | 2/2007 | Guilak et al. |
| 2007/0077236 A1 | 4/2007 | Osther |
| 2007/0087032 A1 | 4/2007 | Chang et al. |
| 2007/0098759 A1 | 5/2007 | Malinin |
| 2007/0106394 A1 | 5/2007 | Chen |
| 2007/0128155 A1 | 6/2007 | Seyedin et al. |
| 2007/0191781 A1 | 8/2007 | Richards et al. |
| 2007/0212389 A1 | 9/2007 | Weiss et al. |
| 2007/0213660 A1 | 9/2007 | Richards et al. |
| 2007/0250164 A1 | 10/2007 | Troxel |
| 2007/0292945 A1 | 12/2007 | Lin et al. |
| 2007/0299517 A1 | 12/2007 | Davisson et al. |
| 2008/0009942 A1 | 1/2008 | Mizuno et al. |
| 2008/0031934 A1 | 2/2008 | MacPhee et al. |
| 2008/0033331 A1 | 2/2008 | MacPhee et al. |
| 2008/0033332 A1 | 2/2008 | MacPhee et al. |
| 2008/0033333 A1 | 2/2008 | MacPhee et al. |
| 2008/0039940 A1 | 2/2008 | Hashimoto et al. |
| 2008/0039954 A1 | 2/2008 | Long et al. |
| 2008/0051624 A1 | 2/2008 | Bonutti |
| 2008/0065210 A1 | 3/2008 | McKay |
| 2008/0071385 A1 | 3/2008 | Binette et al. |
| 2008/0081369 A1 | 4/2008 | Adkisson, IV et al. |
| 2008/0103564 A1 | 5/2008 | Burkinshaw et al. |
| 2008/0113007 A1 | 5/2008 | Kurihara et al. |
| 2008/0153157 A1 | 6/2008 | Yao et al. |
| 2008/0154370 A1 | 6/2008 | Mathies |
| 2008/0199429 A1 | 8/2008 | Hollander et al. |
| 2008/0274157 A1 | 11/2008 | Vunjak-Novakovic et al. |
| 2008/0299214 A1 | 12/2008 | Seyedin et al. |
| 2009/0012629 A1 | 1/2009 | Yao et al. |
| 2009/0069901 A1 | 3/2009 | Truncale et al. |
| 2009/0143867 A1 | 6/2009 | Gage et al. |
| 2009/0149893 A1 | 6/2009 | Semler et al. |
| 2009/0155229 A1 | 6/2009 | Yayon |
| 2009/0181092 A1 | 7/2009 | Thorne et al. |
| 2009/0181093 A1 | 7/2009 | Thorne et al. |
| 2009/0181892 A1 | 7/2009 | Thorne et al. |
| 2009/0214614 A1 | 8/2009 | Everland et al. |
| 2009/0291112 A1 | 11/2009 | Truncale et al. |
| 2009/0319045 A1 | 12/2009 | Truncale et al. |
| 2010/0015202 A1 | 1/2010 | Semler et al. |
| 2010/0086594 A1 | 4/2010 | Amit et al. |
| 2010/0121311 A1 | 5/2010 | Seegert et al. |
| 2010/0168856 A1 | 7/2010 | Long et al. |
| 2010/0209397 A1 | 8/2010 | Maor |
| 2010/0209408 A1 | 8/2010 | Stephen et al. |
| 2010/0274362 A1 | 10/2010 | Yayon et al. |
| 2010/0303765 A1 | 12/2010 | Athanasiou et al. |
| 2010/0322994 A1 | 12/2010 | Kizer et al. |
| 2011/0009963 A1 | 1/2011 | Binnette et al. |
| 2011/0052705 A1 | 3/2011 | Malinin |
| 2011/0070271 A1 | 3/2011 | Truncale et al. |
| 2011/0091517 A1 | 4/2011 | Binette et al. |
| 2011/0097381 A1 | 4/2011 | Binette et al. |
| 2011/0166669 A1 | 7/2011 | Truncale et al. |
| 2011/0177134 A1 | 7/2011 | Harmon et al. |
| 2011/0196508 A1 | 8/2011 | Truncale et al. |
| 2011/0256095 A1 | 10/2011 | Seyedin et al. |
| 2012/0009224 A1 | 1/2012 | Kizer et al. |
| 2012/0009270 A1 | 1/2012 | Kizer et al. |
| 2012/0107384 A1 | 5/2012 | Yao et al. |
| 2012/0156265 A1 | 6/2012 | Binette et al. |
| 2012/0183586 A1 | 7/2012 | Yao et al. |
| 2012/0239146 A1 | 9/2012 | Kizer et al. |

FOREIGN PATENT DOCUMENTS

| | | |
|---|---|---|
| CA | 2261292 A1 | 7/1997 |
| CA | 2261292 C | 7/1997 |
| CA | 2441994 A1 | 3/2002 |
| CA | 2445356 A1 | 10/2003 |
| CA | 2445356 C | 10/2003 |
| CA | 2445558 A1 | 10/2003 |
| CA | 2445558 C | 10/2003 |
| CA | 2449227 A1 | 11/2003 |
| CA | 2449227 C | 11/2003 |
| CA | 2522133 A1 | 4/2004 |
| CA | 2522133 C | 4/2004 |
| CA | 2475905 A1 | 7/2004 |
| CA | 2475905 C | 7/2004 |
| CA | 2480712 A1 | 9/2004 |
| CA | 2487029 A1 | 11/2004 |
| CA | 2487042 A1 | 11/2004 |
| CA | 2496184 A1 | 2/2005 |
| CA | 2563082 A1 | 3/2005 |
| CA | 2570521 A1 | 12/2006 |
| CA | 2631520 A1 | 12/2006 |
| CA | 2708147 A1 | 12/2008 |
| CA | 2717725 A1 | 3/2009 |
| EP | 0006216 A1 | 1/1980 |
| EP | 0133934 A2 | 7/1984 |
| EP | 0341007 A2 | 4/1989 |
| EP | 0493387 B1 | 7/1990 |
| EP | 1142581 A2 | 11/1991 |
| EP | 0610423 B1 | 10/1992 |
| EP | 0654078 B1 | 6/1993 |
| EP | 0592242 A1 | 10/1993 |
| EP | 0592242 B1 | 10/1993 |
| EP | 0641007 A2 | 1/1994 |
| EP | 0669138 A2 | 2/1995 |
| EP | 0906069 B1 | 11/1996 |
| EP | 0877632 B1 | 9/1997 |
| EP | 1003568 B1 | 8/1998 |
| EP | 0867193 A2 | 9/1998 |
| EP | 01010356 A1 | 6/2000 |
| EP | 1303184 B1 | 5/2001 |

| | | | |
|---|---|---|---|
| EP | 1387703 B1 | 5/2001 |
| EP | 1132061 A2 | 9/2001 |
| EP | 1471140 A1 | 1/2003 |
| EP | 1538196 A1 | 8/2003 |
| EP | 1410810 A1 | 10/2003 |
| EP | 1410810 B1 | 10/2003 |
| EP | 1410811 A1 | 10/2003 |
| EP | 1410811 B1 | 10/2003 |
| EP | 1433423 A1 | 10/2003 |
| EP | 1433423 B1 | 10/2003 |
| EP | 1599126 | 3/2004 |
| EP | 1618178 B1 | 4/2004 |
| EP | 1506790 A1 | 8/2004 |
| EP | 1512739 A1 | 9/2004 |
| EP | 1537883 A2 | 12/2004 |
| EP | 1537883 A3 | 12/2004 |
| EP | 1537883 B1 | 12/2004 |
| EP | 1691727 B1 | 12/2004 |
| EP | 1958651 B1 | 12/2004 |
| EP | 2335650 A1 | 12/2004 |
| EP | 2338441 A1 | 12/2004 |
| EP | 2338442 A1 | 12/2004 |
| EP | 2338533 A1 | 12/2004 |
| EP | 1561481 A2 | 2/2005 |
| EP | 1561481 A3 | 2/2005 |
| EP | 1561481 B1 | 2/2005 |
| EP | 1753860 B1 | 2/2005 |
| EP | 1535578 A1 | 6/2005 |
| EP | 1535633 A1 | 6/2005 |
| EP | 1788077 A1 | 11/2006 |
| EP | 0920490 | 2/2008 |
| EP | 2101681 B1 | 8/2011 |
| EP | 2335650 B1 | 10/2012 |
| GB | 2105198 A | 3/1983 |
| GB | 2175507 A | 5/1985 |
| GB | 2404607 A | 9/2005 |
| JP | 59135054 A | 8/1984 |
| JP | 10036534 A | 2/1998 |
| JP | 2002233567 A | 8/2002 |
| JP | 2004136096 A | 5/2004 |
| JP | 2006230749 A | 9/2006 |
| JP | 2003102755 A | 4/2008 |
| WO | 8002501 A1 | 11/1980 |
| WO | 8505274 A1 | 12/1985 |
| WO | 9000060 A1 | 1/1990 |
| WO | 9101711 | 2/1991 |
| WO | 9209697 | 6/1992 |
| WO | 9603112 | 2/1996 |
| WO | 9603160 A1 | 2/1996 |
| WO | 9639170 | 12/1996 |
| WO | 9711090 A1 | 3/1997 |
| WO | WO-9726847 A1 | 7/1997 |
| WO | 9804681 | 2/1998 |
| WO | 9804681 A2 | 2/1998 |
| WO | 9844874 | 10/1998 |
| WO | 9907417 | 2/1999 |
| WO | 9951164 A1 | 10/1999 |
| WO | WO-0006216 A1 | 2/2000 |
| WO | 0029484 A1 | 5/2000 |
| WO | WO-0048837 A1 | 8/2000 |
| WO | 0056251 | 9/2000 |
| WO | WO-0062832 A1 | 10/2000 |
| WO | WO-0074741 A2 | 12/2000 |
| WO | WO-0074741 A3 | 12/2000 |
| WO | 0102030 A2 | 1/2001 |
| WO | 0105443 | 1/2001 |
| WO | WO-0110356 A2 | 2/2001 |
| WO | WO-0123014 A1 | 4/2001 |
| WO | 0167961 | 9/2001 |
| WO | 0168811 A2 | 9/2001 |
| WO | 0168811 A3 | 9/2001 |
| WO | 0185225 A2 | 11/2001 |
| WO | 0185225 A3 | 11/2001 |
| WO | 0197872 | 12/2001 |
| WO | 0224244 A2 | 3/2002 |
| WO | 02067856 A2 | 9/2002 |
| WO | 02076285 A2 | 10/2002 |
| WO | 02080991 A2 | 10/2002 |
| WO | 02089868 | 11/2002 |
| WO | 03077794 A2 | 9/2003 |
| WO | 03093433 A2 | 11/2003 |
| WO | 03093433 A3 | 11/2003 |
| WO | 03100417 | 12/2003 |
| WO | 2004028547 | 4/2004 |
| WO | 2004028584 | 4/2004 |
| WO | 2004028584 A1 | 4/2004 |
| WO | 2004078032 A2 | 9/2004 |
| WO | 2004078032 A3 | 9/2004 |
| WO | 2004078955 | 9/2004 |
| WO | WO-2004078035 A2 | 9/2004 |
| WO | 2004096983 A2 | 11/2004 |
| WO | 2004105576 A2 | 12/2004 |
| WO | 2004110512 A2 | 12/2004 |
| WO | 2004110512 A3 | 12/2004 |
| WO | WO-2005011765 A1 | 2/2005 |
| WO | 2005018491 A2 | 3/2005 |
| WO | 2005044326 | 5/2005 |
| WO | 2005092208 A1 | 5/2005 |
| WO | 2005058207 A1 | 6/2005 |
| WO | 2005060987 | 7/2005 |
| WO | 2005060987 A1 | 7/2005 |
| WO | 2005061018 A1 | 7/2005 |
| WO | 2005065079 | 7/2005 |
| WO | 2005081870 A2 | 9/2005 |
| WO | 2005081870 A3 | 9/2005 |
| WO | 2005092405 A1 | 10/2005 |
| WO | 2005110278 A2 | 11/2005 |
| WO | 2005113751 | 12/2005 |
| WO | 2006002253 A2 | 1/2006 |
| WO | WO-2006002253 A3 | 1/2006 |
| WO | 2006017176 | 2/2006 |
| WO | 2006033698 A2 | 3/2006 |
| WO | 2006033698 A3 | 3/2006 |
| WO | 2006039484 A2 | 4/2006 |
| WO | 2006039484 A3 | 4/2006 |
| WO | 2006068972 A2 | 6/2006 |
| WO | 2006090372 A2 | 8/2006 |
| WO | 2006090372 A3 | 8/2006 |
| WO | 2006113642 A1 | 10/2006 |
| WO | 2006121612 | 11/2006 |
| WO | 2007025290 A2 | 3/2007 |
| WO | 2007025290 A3 | 3/2007 |
| WO | 2007054939 A2 | 5/2007 |
| WO | 2007067637 | 6/2007 |
| WO | 2007067637 A2 | 6/2007 |
| WO | 2007089942 | 8/2007 |
| WO | 2007089948 A2 | 8/2007 |
| WO | 2007089948 A3 | 8/2007 |
| WO | 2007102149 A2 | 9/2007 |
| WO | 2007115336 A2 | 10/2007 |
| WO | 2007143726 A2 | 12/2007 |
| WO | 2008019127 | 2/2008 |
| WO | 2008019128 | 2/2008 |
| WO | 2008019129 | 2/2008 |
| WO | 2008021127 A2 | 2/2008 |
| WO | 2008079194 | 7/2008 |
| WO | 2008079194 A1 | 7/2008 |
| WO | WO-2008079613 A1 | 7/2008 |
| WO | 2008106254 A2 | 9/2008 |
| WO | 2008128075 A1 | 10/2008 |
| WO | 2009039469 A1 | 3/2009 |
| WO | 2009076164 A2 | 6/2009 |
| WO | 2009111069 A1 | 9/2009 |
| WO | 2010078040 A1 | 7/2010 |

OTHER PUBLICATIONS

Black, J, Biological Performance of Tantalum, Clinical Materials, 1994, pp. 167-173, vol. 16.

Bobyn, J.D. et al, Tissue Response to Porous Tantalum Acetabular Cups, J. Arthroplasty, 1999, pp. 347-354, vol. 14, No. 3.

Bobyn, J.D. et al, Effect of pore size on the peel strength of attachment of fibrous tissue to porous-surfaced implants, J. Biomed. Mater. Res., 1982, pp. 571-584, vol. 16.

Bobyn, J.D. et al, Characteristics of bone ingrowth and interface mechanics of a new porous tantalum biomaterial, JBJS (Br), 1999, pp. 907-914, vol. 81-B, No. 5.

Christel, P. et al, Osteochondral Grafting using the Mosaicplasty Technique, www.maitrise-orthop.com/corpusmaitri/orthopaedic/mo76_mosaicplasty/index.shtml, 20 pages.

Feder, J. et al, Tissue Engineering in Musculoskeletal Clinical Practice: The Promise of Chondral Repair Using Neocartilage, Am. Acad. Orthop. Surg., 2004, pp. 219-226, Chapter 22.

Hacking, S.A. et al, Fibrous tissue ingrowth and attachment to porous tantalum, J. Biomed. Mater. Res., 2000, pp. 631-638, vol. 52, No. 4.

Jurgensen, K. et al, A New Biological Glue for Cartilage-Cartilage Interfaces: Tissue Transglutaminase, JBJS (Am), 1997, pp. 185-193, vol. 79.

Kato, Y. et al, Sulfated Proteoglycan Synthesis by Confluent Cultures of Rabbit Costal Chondrocytes Grown in the Presence of Fibroblast Growth Factor, J. Cell Biology, 1985, pp. 477-485, vol. 100.

Marcacci, M. et al, Multiple Osteochondral Arthroscopic Grafting (Mosaicplasty) for Cartilage Defects of the Knee: Prospective Study Results at 2-Year Follow-up, J. Arthroscopic & Related Surgery, 2005, pp. 462-470, vol. 21, No. 4.

Minas, T. et al, Current Concepts in the Treatment of Articular Cartilage Defects, Orthopedics, 1997, pp. 525-538, vol. 20.

Stockwell, R.A., The cell density of human articular and costal cartilage, J. Anat, 1967, pp. 753-763, vol. 101, No. 4.

Thilly, W.G. and Levine, D.W., Microcarrier Culture: A Homogeneous Environment for Studies of Cellular Biochemistry, Methods in Enzymology, 1979, pp. 184-194, vol. LVIII, ISBN 0-12-181958-2, Academic Press, Inc., New York, New York, United States.

Thilly, W.G. et al, Microcarriers and the problem of high density cell culture, From Gene to Protein: Translation in Biotechnology, 1982, pp. 75-103, vol. 19, Academic Press, Inc., New York, New York, United States.

Trattnig, S. et al, Matrix-based autologous chondrocyte implantation for cartilage repair: noninvasive monitoring by high-resolution magnetic resonance imaging, Magnetic Resonance Imaging, 2005, pp. 779-787, vol. 23.

Trattnig, S. et al, Quantitative T2 Mapping of Matrix-Associated Autologous Chondrocyte Transplantation at 3 Tesla An in vivo Cross-Sectional Study, Investigative Radiology, 2007, pp. 442-448, vol. 42, No. 6.

Trattnig, S. et al, Differentiating normal hyaline cartilage from post-surgical repair tissue using fast gradient echo imaging in delayed gadolinium-enhanced MRI (dGEMRIC) at 3 Tesla, Eur Radiol, 2008, pp. 1251-1259, vol. 18.

Tuan, R.S., A second-generation autologous chondrocytes implantation approach to the treatment of focal articular cartilage defects, Arthritis Research & Therapy, 2007, pp. 109-112, vol. 9.

Vacanti, C.A. et al, Synthetic Polymers Seeded with Chondrocytes Provide a Template for New Cartilage Formation, Plastic and Reconstructive Surgery, 1991, pp. 753-759, vol. 88, No. 5.

Vanderploeg, E.J. et al, Articular chondrocytes derived from distinct tissue zones differentially respond to in vitro oscillatory tensile loading, Osteoarthritis and Cartilage, 2008, pp. 1228-1236, vol. 16.

Venkat, R.V. et al, Study of Hydrodynamics in Microcarrier Culture Spinner Vessels: A Particle Tracking Velocimetry Approach, Biotechnology and Bioengineering, 1996, pp. 456-466, vol. 49.

Vishwakarma, G.K, et al, Isolation & cryo-preservation of human foetal articular chondrocytes, Indian J. Med Res, 1993, pp. 309-313, vol. 98.

Von Schroeder, H.P. et al, The use of polylactic acid matrix and periosteal grafts for the reconstruction of rabbit knee articular defects, J. Biomedical Materials Research, 1991, pp. 329-339, vol. 25.

Oldshue, J.Y. et al, Comparison of Mass Transfer Characteristics of Radial and Axial Flow Impellers, Mixing Proceedings of the 6th European Conference, Pavia, Italy, 1988, pp. 345-350.

Wei, X. et al, The Effect of Sodium Selenite on Chondrocytes in Monolayer Culture, Arthritis & Rheumatism, 1986, pp. 660-664, vol. 29, No. 5.

Willers, C. et al, Articular cartilage repair: procedures versus products, Expert Rev Med Devices, 2007, pp. 373-392, vol. 4, No. 3.

Yoshihashi, Y., Tissue Reconstitution by Isolated Articular Chondrocytes in vitro, J. Japanese Orthopaedic Surgical Society, 1983, pp. 629-641, vol. 58.

Zalzal, G. H. et al, Cartilage Grafts-present status, Head & Neck Surgery, 1986, pp. 363-374, vol. 8.

Ze'Ev, A.B. et al, Protein synthesis requires cell-surface contact while nuclear events respond to cell shape in anchorage-dependent fibroblasts, Cell, 1980, pp. 365-372, vol. 21.

Zheng, M.H. et al, Matrix-induced autologous chondrocyte implantation (MACI): Biological and Histological Assessment, Tissue Engineering, 2007, pp. 737-746, vol. 13, No. 4.

Zimber, M.P. et al, TGF-β Promotes the Growth of Bovine Chondrocytes in Monolayer Culture and the Formation of Cartilage Tissue on Three-Dimensional Scaffolds, Tissue Engineering, 1995, pp. 289-300, vol. 1, No. 3.

English translation of Abstract for CA2285382, published Oct. 15, 1998, one page.

English translation of Abstract of AU7100398, published Oct. 30, 1998, one page.

English translation of Abstract of JP2001519700, published Oct. 23, 2001, one page.

English translation of Abstract of JP 2006230749, published Feb. 25, 2005, one page.

Bartlett, W. et al, Autologous chondrocyte implantation versus matrix-induced autologous chondrocyte implantation for osteochondral defects of the knee, A Prospective, Randomised Study, JBJS, 2005, pp. 640-645, vol. 87-B.

Peretti, G.M. et al, Meniscal repair using engineered tissue, J. Orthop Res, 2001, pp. 278-285, vol. 19, No. 2.

Spangenberg, K.M. et al, Histomorphometric Analysis of a Cell-Based Model of Cartilage Repair, Tissue Engineering, 2002, pp. 839-846, vol. 8, No. 5.

Guilak, F. et al, Functional tissue engineering: the role of biomechanics in articular cartilage repair, Clin Orthop Relat Res, 2001, pp. S295-S2305, vol. 391S.

"Pulverize", Merriam-Webster Online Dictionary, Retrieved Jul. 13, 2011 from URL: http://www.merriam-webster.com/dictionary/pulverize, 2 pages.

"Combine", Merriam-Webster Online Dictionary, Retrieved Jul. 13, 2011 from URL: http://www.merriam-webster.com/dictionary/combine, 2 pages.

"Morsel", Merriam-Webster Online Dictionary, Retrieved Jul. 13, 2011 from URL: http://www.merriam-webster.com/dictionary/morsel, 2 pages.

Final Office Action regarding U.S. Appl. No. 10/874,402, issued Feb. 22, 2011, 10 pages.

Non-Final Office Action regarding U.S. Appl. No. 10/874,402, issued Apr. 10, 2008, 8 pages.

Final Office Action regarding U.S. Appl. No. 10/874,402, issued Apr. 17, 2009, 16 pages.

Final Office Action regarding U.S. Appl. No. 10/874,402, issued Apr. 19, 2010, 13 pages.

Non-Final Office Action regarding U.S. Appl. No. 10/874,402, issued Sep. 22, 2010, 10 pages.

Non-Final Office Action regarding U.S. Appl. No. 10/874,402, issued Oct. 27, 2009, 15 pages.

Non-Final Office Action regarding U.S. Appl. No. 11/413,419, issued Jun. 26, 2008, 11 pages.

Final Office Action regarding U.S. Appl. No. 11/413,419, issued Aug. 25, 2009, 13 pages.

Adkisson, H.D. et al, In Vitro Generation of Scaffold Independent Neocartilage, Clinical Orthopaedics and Related Research, 2001, pp. S280-S294, vol. 391S.

Adkisson, H.D. et al, The Potential of Human Allogeneic Juvenile Chondrocytes for Restoration of Articular Cartilage, the American Journal of Sports Medicine, 2010, pp. 1324-1333, vol. 38, No. 7.

Akens, M.K. et al, In Vitro Studies of a Photo-oxidized Bovine Articular Cartilage, J. Vet. Med. A., 2002, pp. 39-45, vol. 49.

Alfredson, H. and Lorentzon, R., Superior results with continuous passive motion compared to active motion after periosteal transplantation: A retrospective study of human patella cartilage defect treatment, Knee Surg. Sports Traumatol Athrosc, 1999, pp. 232-238, vol. 7.

Aston, J. E. and Bentley, G., Repair of articular surfaces by allografts of articular and growth-plate cartilage, Society of Bone and Joint Surgery, 1986, pp. 29-35, vol. 68-B, No. 1.

Augenstein, D.C. et al, Effect of Shear on the Death of Two Strains of Mammalian Tissue Cells, Biotechnology and Bioengineering, 1971, pp. 409-418, vol. XIII.

Aulthouse, A.L. et al, Expression of the human chondrocyte phenotype in vitro, In Vitro Cellular and Developmental Biology, 1989, pp. 659-668, vol. 25, No. 7.

Azizkhan, J.C. and Klagsbrun, M., Chondrocytes contain a growth factor that is localized in the nucleus and is associated with chromatin, PNAS, 1980, pp. 2762-2766, vol. 77, No. 5.

Bacsich, P. and Wyburn, G.M., XXXVIII—The Significance of the Mucoprotein Content on the Survival of Homografts of Cartilage and Cornea, P.R.S.E., 1947, pp. 321-329, vol. LXII, Part III.

Bartlett, W. et al, Autologous chondrocyte implantation at the knee using a bilayer collagen membrane with bone graft, A Preliminary Report, J. Bone and Joint Surgery, 2005, pp. 330-332, vol. 87-B.

Bassleer, C. et al, Human Chondrocytes in tridimensional culture, In Vitro Cellular and Developmental Biology, 1986, pp. 113-119, vol. 22, No. 3, Part I.

Behrens, P. et al, Matrix-associated autologous chondrocyte transplantation/implantation (MACT/MACI)-5-year follow up, The Knee, 2006, pp. 194-202, vol. 13.

Bentley, G. and Greer, R., Homotransplantation of Isolated Epiphyseal and Articular Cartilage Chondrocytes into Joint Surfaces of Rabbits, Nature, 1971, pp. 385-388, vol. 230.

Binette, F. et al, Terminally redifferentiated human articular chondrocytes express hyaline cartilage markers without hypertrophy, 43rd Annual Meeting, Orthopaedic Research Society, 1997, pp. 520.

Boumediene, K. et al, Modulation of rabbit articular chondrocyte (RAC) proliferation by TGF-$\beta$ isoforms, Cell Prolif, 1995, pp. 221-234, vol. 28.

Brighton, C.T. et al, Articular Cartilage Preservation and Storage, I. Application of Tissue Culture Techniques to the Storage of Viable Articular Cartilage, Arthritis and Rheumatism, 1979, pp. 1093-1101, vol. 22, No. 10.

Buckwalter, J.A., Articular Cartilage Injuries, Clinical Orthopaedics and Related Research, 2002, pp. 21-37, No. 402.

Bujia, J. et al, Synthesis of Human Cartilage Using Organotypic Cell Culture, ORL, 1993, pp. 347-351, vol. 55.

Bujia, J. et al, Effect of Growth Factors on Cell Proliferation by Human Nasal Septal Chondrocytes Cultured in Monolayer, Acta Otolaryngol, 1994, pp. 539-543, vol. 114.

Chawla, K. et al, Short-term retention of labeled chondrocyte subpopulations in stratified tissue-engineered cartilaginous constructs implanted in vivo in mini-pigs, Tissue Engineering, 2007, pp. 1525-1538, vol. 13, No. 7.

Chen, F.S. et al, Repair of articular cartilage defects: Part II. Treatment options, The American Journal of Orthopedics, 1999, pp. 88-96.

Cherry, R.S. and Papoutsakis, E.T., Hydrodynamic effects on cells in agitated tissue culture reactors, Bioprocess Engineering, 1986, pp. 29-41, vol. 1.

Cherry, R.S. and Papoutsakis, E.T., Physical mechanisms of cell damage in microcarrier cell culture bioreactors, Biotechnology and Bioengineering, 1988, pp. 1001-1014, vol. 32.

Cherry, R.S. and Papoutsakis, E.T., Understanding and Controlling Fluid-Mechanical Injury of Animal Cells in Bioreactors, Animal Cell Biotechnology, vol. 4, 1990, pp. 72-121, ISBN 0-12-657554-1, Academic Press, Inc., San Diego, California, United States.

Cherubino, P. et al, Autologous chondrocyte implantation using a bilayer collagen membrane: A preliminary report, J. Orthopaedic Surgery, 2003, pp. 10-15, vol. 11, No. 1.

Choi, Y.C. et al, Effect of Platelet Lysate on Growth and Sulfated Glycosaminoglycan Synthesis in Articular Chondrocyte Cultures, Arthritis and Rheumatism, 1980, pp. 220-224, vol. 22, No. 2.

Cooke, M.E. et al, Manuscript-Structured three-dimensional co-culture of mesenchymal stem cells with chondrocytes promotes chondrogenic differentiation without hypertrophy, pp. 1-19.

Coutts, R.D. et al, Section III Basic Science and Pathology Rib periochondrial autografts in full-thickness articular cartilage defects in rabbits, Clinical Orthopaedics and Related Research, 1989, pp. 263-273, No. 275.

Craigmyle, M.B.L., Studies of cartilage autografts and homografts in the rabbit, British Journal of Plastic Surgery, 1955, pp. 93-100.

Croughan, M. S. et al, Hydrodynamic effects on animal cells grown in microcarrier cultures, Biotechnology and Bioengineering, 1987, pp. 130-141, vol. XXIX.

Delbruck, A. et al, In vitro culture of human chondrocytes from adult subjects, Connective Tissue Research, 1986, pp. 155-172, vol. 15.

Dewey, C.F. et al, The dynamic response of vascular endothelial cells to fluid shear stress, J. Biomechanical Engineering, 1981, pp. 177-185, vol. 103.

Dogterom, A.A. et al, Matrix depletion of young and old human articular cartilage by cultured autologous synovium fragments: a chondrocyte-independent effect, Rheumatol Int, 1985, pp. 169-173, vol. 5.

Dowthwaite, G.P. et al, The surface of articular cartilage contains a progenitor cell population, J. of Cell Science, 2004, pp. 889-897, vol. 117.

Drobnic, M. et al, Comparison of four techniques for the fixation of a collagen scaffold in the human cadaveric knee, OsteoArthritis and Cartilage, 2006, pp. 337-344, vol. 14.

Elima, K. and Vuorio, E., Expression of mRNAs for collagens and other matrix components in dedifferentiating and redifferentialting human chondrocytes in culture, FEBS letters, 1989, pp. 195-198, vol. 258, No. 2.

Evans, R.C. and Quinn, T.M., Solute diffusivity correlates with mechanical properties and matrix density of compressed articular cartilage, Archives of Biochemistry and Biophysics, 2005, pp. 1-10, vol. 442.

Farmer, S.R. et al, Altered Translatability of Messenger RNA from Suspended Anchorage-Dependent Fibroblasts: Reversal upon Cell Attachment to a Surface, Cell, 1978, pp. 627-637, vol. 15.

Feder, J. and Tolbert, W.R., The Large-Scale Cultivation of Mammalian Cells, Scientific American, 1983, pp. 36-43, vol. 248, No. 1.

Folkman, J. and Moscona, A., Role of cell shape in growth control, Nature, 1978, pp. 345-349, vol. 273.

Frangos, J.A. et al, Flow effects on prostacyclin production by cultured human endothelial cells, Science, 1985, pp. 1477-1479, vol. 227.

Freed, L.E. et al, Neocartilage formation in vitro and in vivo using cells cultured on synthetic biodegradable polymers, J. of Biomedical Materials Research, 1993, pp. 11-23, vol. 27.

Freed, L.E. et al, Cultivation of Cell-Polymer Cartilage Implants in Bioreactors, J. Cellular Biochemistry, 1993, pp. 257-264, vol. 51.

Freed, L.E. et al, Composition of Cell-Polymer Cartilage Implants, Biotechnology and Bioengineering, 1994, pp. 605-614, vol. 43.

Freed, L.E. and Vunjak-Novakovic, G., Tissue Engineering of Cartilage, Tissue Engineering, published 1995, pp. 1788-1806, Chapter 120, CRC Press, Inc., Boca Raton, Florida United States.

Freed, L.E. and Vunjak-Novakovic, G., Cultivation of Cell-Polymer Tissue Constructs in Simulated Microgravity, Biotechnology and Bioengineering, 1995, pp. 306-313, vol. 46.

Freed, L.E. et al, Tissue engineering of cartilage in space, PNAS, 1997, pp. 13885-13890, vol. 94.

Fry, D.L, Acute Vascular Endothelial Changes Associated with Increased Blood Velocity Gradients, Circulation Research, 1968, pp. 165-197, vol. 22.

Fub, M. et al, Characteristics of human chondrocytes, osteoblasts and fibroblasts seeded onto a type I/III collagen sponge under different culture conditions, A light, scanning and transmission electron microscopy study, Annals of Anatomy, 2000, pp. 303-310, vol. 182.

Galera, P. et al, Effect of Transforming Growth Factor-$\beta$1 (TGF-$\beta$1) on Matrix Synthesis by Monolayer Cultures of Rabbit Articular Chondrocytes during the Dedifferentiation Process, Experimental Cell Research, 1992, pp. 379-392, vol. 200.

Gelse, K. et al, Paracrine Effect of Transplanted Rib Chondrocyte Spheroids Supports Formation of Secondary Cartilage Repair Tissue, J. Orthopaedic Research, 2009, pp. 1216-1225, vol. 27.

Gibson, T. et al, The Long-term survival of cartilage homografts in man, British J. Plastic Surgery, 1958, pp. 177-187, vol. 11.

Gille, J. et al, Migration pattern, morphology and viability of cells suspended in or sealed with fibrin glue: A histomorphologic study, Tissue and Cell, 2005, pp. 339-348, vol. 37.

Girotto, D. et al, Tissue-specific gene expression in chondrocytes grown on three-dimensional hyaluronic acid scaffolds, Biomaterials, 2003, pp. 3265-3275, vol. 24.

Gooch, K.J. et al, Effects of Mixing Intensity on Tissue-Engineered Cartilage, Biotechnol Bioeng, 2001, pp. 402-407, vol. 72.

De Haart, M. et al, Optimization of chondrocyte expansion in culture, Effect of TGFβ-2, bFGF and L-ascorbic Acid on bovine articular chondrocytes, Acta Orthop Scand, 1999, pp. 55-61, vol. 70, No. 1.

Han, E. et al, Shaped, Stratified, Scaffold-free Grafts for Articular Cartilage Defects, Clin Orthop Relat Res, 2008, pp. 1912-1920, vol. 466.

Harrison, E.T. et al, Osteogenin promotes reexpression of cartilage phenotype by dedifferentiated articular chondrocytes in serum-free meduim, Experimental Cell Research, 1991, pp. 340-345, vol. 192.

Harrison, E.T. et al, Transforming growth factor-beta: Its effect on phenotype reexpression by dedifferentiated chondrocytes in the presence and absence of osteogenin, In Vitro Cell, Dev. Biol, 1992, pp. 445-448, vol. 28A.

He, Q. et al, Repair of flexor tendon defects of rabbit with tissue engineering method, Chin J Traumatol (English edition), 2002, pp. 200-208, vol. 5, No. 4.

Hiraki, Y. et al, Effect of transforming growth factor β on cell proliferation and glycosaminoglycan synthesis by rabbit growth-plate chondrocytes in culture, Biochimica et Biophysica Acta, 1988, pp. 91-99, vol. 969.

Hollander, A.P. et al, Maturation of tissue engineered cartilage implanted in injured and osteoarthritic human knees, Tissue Engineering, 2006, pp. 1787-1798, vol. 12, No. 7.

Hollinger, J.O. and Leong, K., Poly(α-hydroxy acids): carriers for bone morphogenetic proteins, Biomaterials, 1996, pp. 187-194, vol. 17, No. 2.

Homminga, G. N. et al, Perichondral grafting for cartilage lesions of the knee, J. Bone Joint Surg (Br), 1990, pp. 1003-1007, vol. 72-B, No. 6.

Horton, W.E. et al, Transforming growth factor-beta and fibroblast growth factor act synergistically to inhibit collagen II synthesis through a mechanism involving regulatory DNA sequences, J. Cellular Physiology, 1989, pp. 8-15, vol. 141.

Hu, W.S., Bioreactors for animal cell cultivation, Recent Advances in Biotechnology, 1992, pp. 243-261, ISBN 0-7923-1632-0, Kluwer Academic Publishers, Dordrecht, Netherlands.

Iwasa, J. et al, Clinical application of scaffolds for cartilage tissue engineering, Knee Surg Sports Traumatol Arthorsc, 2008, pp. 561-577, vol. 17, No. 6.

Jin, C.Z. et al, Human amniotic membrane as a delivery matrix for articular cartilage repair, Tissue Engineering, 2007, pp. 693-703, vol. 13, No. 4.

Jones, C.W. et al, Matrix-induced autologous chondrocyte implantation in sheep: objective assessments including confocal arthroscopy, J. Orthopaedic Research, 2008, pp. 292-303, vol. 26.

Kandel, R.A. et al, Fetal bovine serum inhibits chondrocyte collagenase production: interleukin 1 reverses the effect, Biochimica et Biophysics Acta, 1990, pp. 130-134, vol. 1053.

Kavalkovich, K.W. et al, Chondrogenic differentiation of human mesenchymal stem cells within an alginate layer culture system, In vitro Cell Dev Biol Animal, 2002, pp. 457-466, vol. 38.

Kimura, T. et al, Basic Science and Pathology, Chondrocytes embedded in collagen gels maintain cartilage phenotype during long-term cultures, Clinical Orthopaedic and Related Research, 1984, pp. 231-239, No. 186.

Klagsbrun, M. et al, The stimulation of DNA synthesis and cell division in chondrocytes and 3T3 cells by a growth factor isolated from cartilage, Experimental Cell Research, 1977, pp. 99-108, vol. 105.

Klagsbrun, M. and Smtih, S., Purification of a cartilage-derived growth factor, J. Biological Chem, 1980, pp. 10859-10866, vol. 255, No. 22.

Klein, T.J. et al, Tissue engineering of stratified articular cartilage from chondrocyte subpopulations, OsteoArthritis and Cartilage, 2003, pp. 595-602, vol. 11.

Klein, T.J. et al, Tailoring secretion of proteoglycan 4 (PRG4) in tissue-engineered cartilage, Tissue Engineering, 2006, pp. 1429-1439, vol. 12, No. 6.

Kon, E. et al, Arthroscopic second generation autologous chondrocyte implantation at 48 months follow up, Osteoarthritis and Cartilage, 2007, pp. B44 45, vol. 15, Suppl. B.

Kon, E. et al, Arthroscopic Second-generation Autologous Chondrocyte Implantation Compared with Microfracture of Chondral Lesions of the Knee, Am J. of Sports Medicine, 2009, pp. 33-41, vol. 37, No. 1.

Kon, E. et al, Second generation issues in cartilage repair, Sports Med Arthrosc Rev, 2008, pp. 221-229, vol. 16, No. 4.

Krueger, J.W. et al, An in vitro study of flow response by cells, J. Biomechanics, 1971, pp. 31-36, vol. 4.

Kuettner, K.E. et al, Synthesis of Cartilage Matrix by Mammalian Chondrocytes In Vitro I. Isolation, Culture Characteristics, and Morphology, J. Cell Biology, 1982, pp. 743-750, vol. 93.

Kujawa, M.J. et al, Hyaluronic acid bonded to cell culture surfaces inhibits the program of myogenesis, Developmental Biology, 1986, pp. 10-16, vol. 113.

Kujawa, M.J. et al, Substrate-bonded hyaluronic acid exhibits a size-dependent stimulation of chondrogenic differentiation of stage 24 limb mesenchymal cells in culture, Developmental Biology, 1986, pp. 519-528, vol. 114.

Kujawa, M.J. and Caplan, A.I., Hyaluronic acid bonded to cell-culture surfaces stimulates chondrogenesis in stage 24 limb mesenchyme cell cultures, Developmental Biology, 1986, pp. 504-518, vol. 114.

Lee, J.D. et al, Primary cultured chondrocytes of different origins respond differently to bFGF and TGF-β, Life Sciences, 1997, pp. 293-299, vol. 61, No. 3.

Leopold, G., Experimental Studies into the Etiology of Tumors, Achiv f. path. Anat., 1881, pp. 283-324, vol. LXXXV, No. 2.

Libera, J. et al, Cartilage Engineering, Fundamentals of Tissue Engineering and Regenerative Medicine, Chapter 18, pp. 233-242, ISBN: 978-3-540-77754-0, le-lex publishing Services, oHG, Leipzip, Germany.

Lin, Z. et al, Gene Expression Profiles of Human Chondrocytes during Passaged Monolayer Cultivation, J. Orthopaedic Research, 2008, pp. 1230-1237, vol. 26.

Liu, L.S. et al, an osteoconductive collagen/hyaluronate matrix for bone regeneration, Biomaterials, 1999, pp. 1097-1108, vol. 20.

Lui, X. et al, In vivo ectopic chondrogenesis of BMSCs directed by mature chondrocytes, Biomaterials, 2010, pp. 9406-9414, vol. 31.

Loeb, L., Autotransplantation and homoiotransplantation of cartilage in the guinea-pig, Am J. Pathology, 1926a, pp. 111-122, vol. 2.

Lucas, P.A. et al, Ectopic induction of cartilage and bone by water-soluble proteins from bovine bone using a collagenous delivery vehicle, J. Biomed Mater Res: Applied Biomaterials, 1989, pp. 23-39, vol. 23, No. A1.

Luyten, F.P. And Reddi, A.H., Articular cartilage repair: potential role of growth and differentiation factors, Biological Regulation of the Chondrocytes, pp. 227-236, Chapter 9, ISBN: 0-8493-6733-6, CRC Press, Inc., Boca Raton, Florida, United States.

Mackay, A. M. et al, Chondrogenic Differentiation of Cultured Human Mesenchymal Stem Cells from Marrow, Tissue Engineering, 1998, pp. 415-430, vol. 4, No. 4.

Malemud, C. J. and Sokoloff, L., The effect of chondrocyte growth factor on membrane transport by articular chondrocytes in monolayer culture, Connective Tissue Research, 1978, pp. 1-9, vol. 6.

Mandl, E.W. et al, Serum-free medium supplemented with high-concentration FGF2 for cell expansion culture of human ear chondrocytes promotes redifferentiation capacity, Tissue Engineering, 2002, pp. 573-582, vol. 8, No. 4.

Mandl, E.W. et al, Multiplication of human chondrocytes with low seeding densities accelerates cell yield without losing redifferentiation capacity, Tissue Engineering, 2004, pp. 109-120, vol. 10, No. 1/2.

Maracacci, M. et al, Articular Cartilage Engineering with Hyalograft C, 3-year clinical results, Clinical Orthopaedics and Related Research, 2005, pp. 96-105, No. 435.

Marlovits, S. et al, Early postoperative adherence of matrix-induced autologous chondrocyte implantation for the treatment of full-thickness cartilage defects of the femoral condyle, Knee Surg Sports Traumatol Arthrosc, 2005, pp. 451-457, vol. 13.

Marlovits, S. et al, Changes in the ratio of type-I and type-II collagen expression during monolayer culture of human chondrocytes, JBJS, 2004, pp. 286-295, vol. 86-B.

Mathiowitz, E. et al, Biologically erodable microspheres as potential oral drug delivery systems, Letters to Nature, 1997, pp. 410-414, vol. 386.

Mcdermott, A.G.P. et al, Fresh Small-Fragment Osteochondral Allografts Long-term Follow up Study on First 100 cases, Clinical Orthopaedics and Related Research, 1985, pp. 96-102, No. 197.

McKibbin, B., Immature Joint Cartilage and the Homograft Reaction, JBJS, 1971, pp. 123-135, vol. 53B, No. 1.

McNickle, A.G. et al, Overview of Existing Cartilage Repair Technology, Sports Med Arthrosc Rev, 2008, pp. 196-201, vol. 16, No. 4.

McQueen, A. et al, Flow effects on the viability and lysis of suspended mammalian cells, Biotechnology Letters, 1987, pp. 831-836, vol. 9, No. 12.

Merchuk, J.C., Shear Effects on Suspended Cells, Advances in Biochemical Engineering Biotechnology, 1988, pp. 1988-1995, vol. 44, Springer-Verlag, Berlin Heidelberg, Germany.

Merchuk, J.C., Why use air-lift bioreactors?, TIBTECH, 1990, pp. 66-71, vol. 8.

Mienaltowski, M.J. et al, Differential gene expression associated with postnatal equine articular cartilage maturation, BMC Musculoskeletal Disorders, 2008, pp. 149-162, vol. 9.

Mow, V.C. et al, Experimental Studies on Repair of Large Osteochondral Defects at a High Weight Bearing Area of the Knee Joint: A Tissue Engineering Study, Transactions of the ASME, 1991, pp. 198-207, vol. 113.

Nixon, A.J. et al, Isolation, propagation, and cryopreservation of equine articular chondrocytes, Am J Vet Res, 1992, pp. 2364-2370, vol. 53, No. 12.

Nixon, A.J. et al, Temporal matrix synthesis and histologic features of a chondrocyte-laden porous collagen cartilage analogue, AM J Vet Res, 1993, pp. 349-356, vol. 54, No. 2.

Nixon, A.J. and Fortier, L.A., New Horizons in Articular Cartilage Repair, AAEP Proceedings, 2001, pp. 217-226, vol. 47.

Obradovic, B. et al, Integration of engineered cartilage, J. Orthopaedic Research, 2001, pp. 1089-1097, vol. 19.

O'Driscoll, S. W. and Salter, R.B., The Repair of Major Osteochondral Defects in Joint Surfaces by Neochondrogenesis with Autogenous Osteoperiosteal Grafts Stimulated by Continuous Passive Motion an experimental investigation in the rabbit, J. Orthopaedic Research, 2001, pp. 1089-1097, vol. 19.

Papoutsakis, E.T., Fluid-mechanical damage of animal cells in bioreactors, TIBTECH, 1991, pp. 427-437, vol. 9.

Pavesio, A. et al, Hyaluronan-based scaffolds (Hyalograft C) in the treatment of knee cartilage defects: preliminary clinical findings, Tissue engineering of cartilage and bone, 2003, pp. 203-217, Wiley, Chichester, West Sussex, England.

Peretti, G.M. et al, Bonding of Cartilage Matrices with Cultured Chondrocytes: An Experimental Model, JBJS, 1998, pp. 89-95, vol. 16.

Peretti, G.M. et al, Cell-based bonding of articular cartilage: An extended study, J Biomed Mater Res A, 2003, pp. 517-524, vol. 64, No. 3.

Pieter, A. et al, Effect of purified growth factors on rabbit articular chondrocytes in monolayer culture, Arthritis and Rheumatism, 1982, pp. 1217-1227, vol. 25, No. 10.

Reginato, A.M. et al, Formation of nodular structures resembling mature articular cartilage in long-term primary cultures of human fetal epiphyseal chondrocytes on a hydrogel substrate, Arthritis and Rheumatism, 1994, pp. 1338-1349, vol. 37, No. 9.

Robinson, D. et al, Regenerating Hyaline Cartilage in Articular Defects of Old Chickens Using Implants of Embryonal Chick Chondrocytes Embedded in a New Natural Delivery Substance, Calcif Tissue Int, 1990, pp. 246-253, vol. 46.

Ronga, M. et al, Arthroscopic autologous chondrocyte implantation for the treatment of a chondral defect in the tibial plateau of the knee, J. Arthroscopic and Related Surgery, 2004, pp. 79-84, vol. 20, No. 1.

Ronga, M. et al, Tissue engineering techniques for the treatment of a complex knee injury, J. Arthroscopic and Related Surgery, 2006, pp. 576.e1-576.e3, vol. 22, No. 5.

Rosier, R.N. et al, Transforming growth factor beta: an autocrine regulator of chondrocytes, Connective Tissue Research, 1989, pp. 295-301, vol. 20.

Rosselot, G. et al, Development of a serum-free system to study the effect of growth hormone and insulinlike growth factor-I on cultured postembryonic growth plate chondrocytes, In Vitro Cell Dev Biol, 1992, pp. 235-244, vol. 28A.

Russlies, M. et al, A cell-seeded biocomposite for cartilage repair, Ann Anat, 2002, pp. 317-323, vol. 184.

Saini, S. and Wick, T.M., Concentric cylinder bioreactor for production of tissue engineered cartilage: Effect of sedding density and hydrodynamic loading on construct development, Biotechnol Prog, 2003, pp. 510-521, vol. 19.

Salter, R. B., The biological concept of continuous passive motion of synovial joints: The first 18 years of basic research and its clinical application, CPM of Synovial Joints, 1990, pp. 335-353, Chapter 23, Raven Press Ltd, New York, United States.

Schmidt, T.A. et al, Synthesis of proteoglycan 4 by chondrocyte subpopulations in cartilage explants, monolayer cultures, and resurfaced cartilage cultures, Arthritis and Rheumatism, 2004, pp. 2849-2857, vol. 50, No. 9.

Schwan, B.L., Human Amniotic Membrane Transplantation for the Treatment of Ocular Surface Disease, Human Amniotic Membrane Transplantation, 2002, pp. 1-7.

Schwarz, R.P. et al, Cell Culture for Three-Dimensional Modeling in Rotating-Wall Vessels: An Application of Simulated Microgravity, J. Tiss. Cult. Meth., 1992, pp. 51-58, vol. 14.

Shahgaldi, B.F. et al, Repair of Cartilage Lesions Using Biological Implants, JBJS, 1991, pp. 57-64, vol. 73-B.

Smtih, R.L. et al, Effects of Fluid-Induced Shear on Articular Chondrocyte Morphology and Metabolism In Vitro, JBJS, 1995, pp. 824-831, vol. 13.

Sokoloff, L. et al, Sulfate Incorporation by Articular Chondrocytes in Monolayer Culture, Arthritis and Rheumatism, 1970, pp. 118-124, vol. 13, No. 2.

Sokoloff, L. et al, In vitro culture of articular chondrocytes, Federation Proc, 1973, pp. 1499-1502, vol. 32.

Song, C.X. et al, Formulation and characterization of biodegradable nanoparticles for intravascular local drug delivery, J. Controlled Release, 1997, pp. 197-212, vol. 43.

Specchia, N. et al, Fetal chondral homorgrafts in the repair of articular cartilage defects, Bulletin Hospital for Joint Disease, 1996, pp. 230-235, vol. 54, No. 4.

Stathopoulos, N.A. and Hellums, J.D., Shear Stress Effects on Human Embryonic Kidney Cells In Vitro, Biotechnology and Bioengineering, 1985, pp. 1021-1026, vol. XXVII.

Stewart, M.C. et al, Phenotypic stability of articular chondrocytes in vitro: the effects of culture models, bone morphogenetic protein 2, and Serum Supplementation, Journal of Bone and Mineral Research, 2000, pp. 166-174, vol. 15, No. 1.

Stiles, C.D. et al, Dual control of cell growth by somatomedins and platelet-derived growth factor, PNAS, 1979, pp. 1279-1283, vol. 76, No. 3.

Langer, F. and Gross, A.E., Immunogenicity of Allograft Articular Cartilage, JBJS, 1974, pp. 297-304, vol. 56-A, No. 2.

Langer, F. et al, The Immunogenicity of Fresh and Frozen Allogeneic Bone, JBJS, 1975, pp. 216-220, vol. 57-A, No. 2.

Lavrishcheva, G.I., Filling Bone Cavities with Minced Cartilage, Ortopediia travmatologiia I protezirovanie, 1955, pp. 80, vol. 1.

Lee, J.W., Preplanned correction of enophthalmos using diced cartilage grafts, British J. Plastic Surg, 2000, pp. 17-23, vol. 53.

Lemperg, R., et al, Transplantation of diced rib cartilage to the hip joint. Experimental study on adult dogs, Acta Soc Med Ups, 1965, pp. 197-212, vol. 70, No. 3.

Lennert, K.H. and Haas, H.G., Fibrin Adhesive in the Surgical Treatment of the Pseudoarthrosis of the Scaphoid Bone—Methods and Results, Unfallchirurgie, 1988, pp. 158-160, vol. 14, No. 3.

Leopold, G., XIV. Experimental Studies into the Etiology of Tumors, Archiv f. path. Anat., 1881, pp. 283-324, vol. LXXXV, No. 2.

Limberg, A.A., Supporting and Contour Plastic Repair by Needle Administration of Minced Carthage, Vestnik khirurgii imeni I.I. Grekova, 1957, pp. 68-73, vol. 78, No. 4.

Limberg, A.A., The use of diced cartilage by injection with a needle. Part 1. Clinical investigations, Plast Reconstr Surg Transplant Bull., 1961, pp. 523-536, vol. 28.

Limberg, A.A., The use of diced cartilage by injection with a needle. Part 2. Morphologic Changes in the Diced Human Cartilage After Auto- and Homoplasty, Plast Reconstr Surg Transplant Bull., 1961, pp. 649-655, vol. 28.

Loeb, L, Autotransplantation and Homoiotransplantation of Cartilage in the Guinea-Pig, Am. J. Pathology, 1926, pp. 111-122, vol. II.

Lu, Y. et al, Minced Cartilage without Cell Culture Serves as an Effective Intraoperative Cell Source for Cartilage Repair, J Orthop Res., 2006, pp. 1261-1270, vol. 24, No. 6.

Lucht, U. et al, Fibrin sealant in bone transplantation. No effects on blood flow and bone formation in dogs, Acta Orthop Scand., 1986, pp. 19-24, Vol. 57, No. 1.

Mahomed, M.N. et al, The long-term success of fresh, small fragment osteochondral allografts used for intraarticular post-traumatic defects in the knee joint, Orthopedics, 1992, pp. 1191-1199, vol. 15, No. 10.

Maletius, W. and Lundberg, M., Refixation of large chondral fragments on the weight-bearing area of the knee joint: a report of two cases, Arthroscopy., 1994, pp. 630-633, vol. 10, No. 6.

Mankin, H.J., Localization of Tritiated Thymidine in Articular Cartilage of Rabbits: II. Repair in Immature Cartilage, JBJS, 1962, pp. 688-698, vol. 44.

Mankin, H.J., Localization of Tritiated Thymidine in Articular Cartilage of Rabbits: III. Mature Articular Cartilage, JBJS, 1963, pp. 529-540, vol. 45.

Mankin, H.J., Current Concepts Review, The Response of Articular Cartilage to Mechanical Injury, JBJS, 1982, pp. 460-466, vol. 64, No. 3.

Marcacci, M. et al, Articular cartilage engineering with Hyalograft C: 3-year clinical results, Clin Orthop Relat Res., 2005, pp. 96-105, No. 435.

Marcacci, M. et al, Use of autologous grafts for reconstruction of osteochondral defects of the knee, Orthopedics, 1999, pp. 595-600, vol. 22, No. 6.

Marchac, D. and Sandor, G., Face lifts and sprayed fibrin glue: an outcome analysis of 200 patients, Br J Plast Surg., 1994, pp. 306-309, vol. 47, No. 5.

Marchac, D. et al, Fibrin glue fixation in forehead endoscopy: evaluation of our experience with 206 cases, Plast Reconstr Surg., 1997, pp. 713-714, vol. 100, No. 3.

Matras, H., Fibrin Seal: The State of the Art, J. Oral Maxilofac Surg, 1985, pp. 605-611, vol. 43.

Matsusue, Y. et al, Biodegradable Pin Fixation of Osteochondral Fragments of the Knee, Clin Ortho Rel Res, 1996, pp. 166-173, No. 322.

McDermott, A.G.P. et al, Fresh Small-Fragment Osteochondral Allografts, Clin Orthop Relat Res., 1985, pp. 96-102, No. 197.

McKibbin, B, Immature Joint Cartilage and the Homograft Reaction, JBJS, 1971, pp. 123-135, vol. 53B, No. 1.

Meachim, G. and Roberts, C., Repair of the joint surface from subarticular tissue in the rabbit knee, J Anat., 1971, pp. 317-327, vol. 109, Part 2.

Meyers, M.H. and Herron, M., A Fibrin Adhesive Seal for the Repair of Osteochondral Fracture Fragments, Clin Ortho Rel Res, 1984, pp. 258-263, No. 182.

Mitchell, N. and Shepard, N., The resurfacing of adult rabbit articular cartilage by multiple perforations through the subchondral bone, JBJS, 1976, pp. 230-233, vol. 58, No. 2.

Mithofer, K. et al, Functional outcome of knee articular cartilage repair in adolescent athletes, Am J Sports Med., 2005, pp. 1147-1153, vol. 33, No. 8.

Miura, Y et al, Brief exposure to high-dose transforming growth factor-beta1 enhances periosteal chondrogenesis in vitro: a preliminary report, JBJS, 2002, pp. 793-799, vol. 84-A, No. 5.

Murray, M.M. and Spector, M, The migration of cells from the ruptured human anterior cruciate ligament into collagen-glycosaminoglycan regeneration templates in vitro, Biomaterials, 2001, pp. 2393-2402, vol. 22.

Nageotte, J., The Organization of Matter in its Connections with Life. Studies of General Anatomy and Experimental Morphology on teh Connective Tissue and the Nerve, L'Organisation De La Matiere, 1922, pp. 95-98.

Niekisch, V.R., English Summary only of Possible methods of using fibrin-glue protection in maxillo facial surgery, Zahn Mund Kieferheilkd Zentralbl, 1980, pp. 555-561, vol. 68, No. 6.

Nixon, A.J., et al, Isolation, propagation, and cryopreservation of equine articular chondrocytes, AM J Vet Res, 1992, pp. 2364-2370, vol. 53, No. 12.

Nixon, A.J., and Fortier, L.A, New Horizons in Articular Cartilage Repair, AAEP Proceedings, 2001, pp. 217-226, vol. 47.

O'Driscoll, S.W. et al, The chondrogenic potential of free autogenous periosteal grafts for biological resurfacing of major full-thickness defects in joint surfaces under the influence of continuous passive motion. An experimental investigation in the rabbit, J Bone Joint Surg Am, 1986, pp. 1017-1035, vol. 68, No. 7.

O'Driscoll, S.W. and Salter, R.B., The Repair of Major Osteochondral Defects in Joint Surfaces by Neochondrogenesis with Autogenous Osteoperiosteal Grafts Stimulated by Continuous Passive Motion, Clin Ortho Rel Res, 1986, pp. 131-140, No. 208.

Oegema, T.R. and Thompson, R.C. Jr, Characterization of a hyaluronic acid-dermatan sulfate proteoglycan complex from dedifferentiated human chondrocyte cultures, J Biol Chem., 1981, pp. 1015-1022, vol. 256, No. 2.

Ohlsen, L. and Widenfalk, B., The Early Development of Articular Cartilage After Perichondrial Grafting, Scand J. Plast Reconstr Surg, 1983, pp. 163-177, vol. 17.

Outerbridge, H.K. et al, The Use of a Lateral Patellar Autologous Graft for the Repair of a Large Osteochondral Defect in the Knee, J Bone Joint Surg Am., 1995, pp. 65-72, vol. 77, No. 1.

Paar, O. et al,Cartilage Adhesion at the Knee Joint, Clinical Follow up Examination, Akt. Traumatol, 1984, pp. 15-19, vol. 14.

Paccola, C.A. et al, Fresh Immature Articular Cartilage Allografts—A Study on the Integration of Chondral and Osteochondral Grafts Both in Normal and in Papain-Treated Knee Joints of Rabbits, Arch Orthop Traumat Surg., 1979, pp. 253-259, vol. 93.

Park, J.J. et al, Comparison of the Bonding Power of Various Autologous Fibrin Tissue Adhesives, Am J Otology, 1997, pp. 655-659, vol. 18, No. 5.

Park, M.S., Tympanoplasty using autologous crushed cartilage, Rev Laryngol Otol Rhinol, 1995, pp. 365-368, vol. 116, No. 5.

Pascone, M. and Dioguardi, D., Fibrin Sealant in Plastic Surgery of the Head, Plastic Surgery Nerve Repair Burns, Fibring Sealing in Surgical and Nonsurgical Fields, 1995, pp. 11-15, vol. 3, Springer-Verlag, Berlin Heidelberg.

Passl, R. et al, Problems of Pure Homologous Articular Cartilage Transplantation, Verh Anat Ges, 1976, pp. 675-678, vol. 70.

Punzet, G. et al, Morphological and Therapeutic Aspects of Osteochondrosis dissecans and Aseptic Bone Necroses, Acta Medica Austriaca, 1978, pp. 17-18, Suppl. No. 11.

Passl, R. et al, Fibrin Gluing of Cartilage Surfaces—Experimental Studies and Clinical Results, Med. u. Sport, 1979, pp. 23-28, vol. 19 (1/2).

Passl, R. et al, Homologous Cartilage Transplants in Animal Experiments, 4th Orthopedics Symposium, Heidelberg, 1981, pp. 102-105, Horst Cotta and Arnim Braun (eds), Georg Thieme Verlag Stuttgart, New York.

Schaffer, D.J. et al, English abstract only of foreign patent No. WO00/74741 A2, international filing date, Jun. 8, 2000, one page.

Schaffer, D.J. et al, English abstract only of foreign patent No. WO00/74741 A3, international filing date, Jun. 8, 2000, one page.

Cherubine, P. et al, English abstract only of Autologous chondrocyte implantation using a bilayer collagen membrane: a preliminary report, J. Orthop Surg (Hong)Kong), 3002, pp. 10-5, vol. 11, No. 1.

Yamamoto, K, et al, English abstract only of Japanese publication No. 2006230749A, publication date Sep. 7, 2006, one page.

Verwerd, C.D.A. et al, Wound Healing of Autologous Implants in the Nasal Septal Cartilage, ORL, 1991, pp. 310-314, vol. 53.

Wilflingseder, P., Cancellous Bone Grafts, S Afr Med J., 1957, pp. 1267-1271, vol. 31, No. 50.

Wilfingseder, P., Treatment of Mandibular Facial Dysostosis, S Afr Med J., 1957, pp. 1296-1298, vol. 31, No. 51.

Pirsig, W., English Abstract only of Regeneration of septal cartilage in children after septoplasty. A histological study, Acta Otolaryngol, 1975, pp. 451-459, vol. 79, No. 5-6.

Passl, R. et al, Homologous articular cartilage transplantation in animal experiments. Preliminary studies on sheep (author's transl), Arch Orthop Unfallchir., 1976, pp. 243-256, vol. 86, No. 2.

Hunter, W., VI. Of the Structure and Difeafes of Articulating Cartilages, Academiae Grypeswaldensis Bibliotheca, 1775, pp. 514-521, vol. 1.

Wikipedia print out of website—http://en.wikipedia.org/wiki/Alpha-2-Macroglobulin, 8 pages.

Kallio, K.E., Arthroplastia Cutanea, Discussion by T. Heirtom, ACTA Orhtopaedica Scandinavica, 1957, pp. 327-328, vol. 26.

Peer, L.A., Transplanation of Tissues—Cartilage, Bone, Fascia, Tendon, and Muscle, The Williams & Wilkins Company, 1955, pp. 69-137 and 392-393, vol. 1, Baltimore, Maryland, USA.

Mannhelm, A., Abstract—Free Autoplastic Cartilage Transplantation, J. Am Med Assoc., 1926, pp. 2132, vol. 87, No. 25.

Nehrer, S. and Minas, T., Treatment of Articular Cartilage Defects, Investigative Radiology, 2000, pp. 639-646, vol. 35, No. 10.

Prudden, T.M., Experimental studies on the transplantation of cartilage, Am. J. M. Sc., 1881, pp. 360-370, vol. 82.

Shands, A.R., Jr., The regeneration of hyaline cartilage in joints. An experimental study, Arch. Surg., 1931, pp. 137-178, vol. 22.

Cheung, H.S. and Haak, M.H., Growth of osteoblasts on porous calcium phosphate ceramic: an in vitro model for biocompatibility study, Biomaterials, 1989, pp. 63-67, vol. 10.

Sittinger, M. et al, Engineering of cartilage tissue using bioresorbable polymer carriers in perfusion culture, Biomaterials, 1994, pp. 451-456, vol. 15, No. 6.

Polettini, B., English abstract only Experimental Grafts of Cartilage and Bone, J.A.M.A., 1923, p. 360, vol. 80.

Braun, A and Heine, W.D., Abstract of The Use of Fibrin Adhesive In Fixation of Osteochondral Fragments, Year unknown, Canadian Orthopaedic Research Society, pp. 215-216.

Rohrbach, JM et al, Abstract only of Biological corneal replacement an alternative to keratoplasty and keratoprosthesis? A pilot study with heterologous hyaline cartilage in the rabbit model, 1995, Klin Monatsbl. Augenheilkd., pp. 191-196, vol. 207, No. 3.

Fontana, A et al, Abstract only of Cartilage chips synthesized with fibrin glue in rhinoplasty, Aestetic Plast Surg, 1991, pp. 237-240, vol. 15, No. 3.

Mainil-Varlet, P et al, Abstract only of Articular cartilage repair using a tissue engineered cartilage like implant: an animal study, Osteoarthritis Cartilage, 2001, pp. s:6-15, vol. 9.

Erol, Oo, the Turkish delight: a pliable graft for rhinoplasty, Plast Reconstr Surg, 2000, pp. 2229-2241, vol. 105, No. 6.

DeGroot, J. et al, Age related decrease in Proteoglycan synthesis of human articular chondrocytes, 1999, Arthritis & Rheumatism, pp. 1003-1009, vol. 42, No. 5.

Feder, J. et al, The promise of chondral repair using neocartilage, 2004, Tissue engineering in musculoskeletal clinical practice, 1st Edition, American Academy of Orthopaedic Surgeons, pp. 219-226, Chapter 22, Section 3.

Morales, T.I., Review: Chondrocyte moves: clever strategies?, Osteoarthritis and Cartilage, 2007, pp. 861-871, vol. 15.

Namba, R.S. et al, Spontaneous repair of superficial defects in articular cartilage in a fetal lamb model, 1998, JBJS, pp. 4-10, vol. 80, No. 1.

Williamson, A.K., et al, Compressive properties and function composition relationships of developing bovine articular cartilage, J. Orthopaedic Research, 2001, pp. 1113-1121, vol. 19.

Specchia, N. et al, Fetal chondral homografts in the repair of articular cartilage defects, Bulletin Hospital for Joint Diseases, 1996, pp. 230-235, vol. 54, No. 4.

Brown, K.R. et al, English Abstract of Japanese publication No. 2003-102755, 1 page.

Lapchinsky, A.G., et al., English abstract only of Apparatus for grinding cartilage in plastic surgery, 1960, primenenija Moskva, pp. 209-213, No. 4.

Imbert, L. et al, English translated Abstract only of Research on cartilage grafts hetero-plastic, 1916, Rev. de chir., pp. 111-128, vol. 52.

Iwamoto, Y. et al, English abstract of WO2005/011765, published Feb. 10, 2005, 1 page.

Ochi, M. et al, English abstract of Japanese publication No. 2002-233567, 1 page.

Sengupta, S. and Lumpur, K, The fate of transplants of articular cartilage in the rabbit, 1974, JBJS, pp. 167-177, vol. 56B, No. 1.

Didier R., English translated Abstract only of the production of cartilage and bone grafts in living and dead rabbits, 1928, Compt. rend. Soc de biol, pp. 443-445, vol. 98.

Egkher, E., Indications and Limits of Fibrin Adhesive Applied to Traumatological Patients, Traumatology and Orthopaedics, 1986, pp. 144-151, vol. 7, Springer-Verlag, Berlin Heidelberg.

Erikson, U. et al, English abstract only, A roentgenological method for the determination of renal blood flow. A preliminary report, Acta Soc Med Ups, 1965, pp. 213-216, vol. 70, No. 3.

Erol, O.O., The Turkish Delight: A Pliable Graft for Rhinoplasty, Plast. Reconstr. Surg., 2000, pp. 2229-2241, vol. 105.

Evans, C.H., et al, Experimental Arthritis Induced by Intraarticular Injection of Allogenic Cartilageinous Particles into Rabbit Knees, Arthritis and Rheumatism, 1984, pp. 200-207, vol. 27, No. 2.

Farrior, R.T., Implant Materials in Restoration of Facial Contour, Laryngoscope, 1966, pp. 934-954, vol. 76, No. 5.

Feldman, M.D., et al, Compatibility of Autologous Fibrin Adhesive With Implant Materials, Arch Otolaryngol Head Neck Surg, 1988, pp. 182-185, vol. 114.

Fontana, A., et al, Cartilage Chips Synthesized with Fibrin Glue in Rhinoplasty, Aesth Plast Surg, 1991, pp. 237-240, vol. 15.

Furukawa, T. et al, Biochemical Studies on Repair Cartilage Resurfacing Experimental Defects in the Rabbit Knee, J Bone Joint Surg Am, 1980, pp. 79-89, vol. 62, No. 1.

Gaudernak, T., et al, Clinical Experiences Using Fibrin Sealant in the Treatment of Osteochondral Fractures, Fibrin Sealant in Operative Medicine-Traumatology and Orthopaedics, 1986, pp. 91-102, vol. 7, Springer-Verlag, Berlin Heidelberg.

Gerngross, H. et al, Experimental Studies on the Influence of Fibrin Adhesive, Factor XIII, and Calcitonin on the Incorporation and Remodeling of Autologous Bone Grafts, Arch Orthop Trauma Surg, 1986, pp. 23, 31, vol. 106.

Gersdorff, M.C.H., and Robillard, T.A., "How I Do It"—Otology and Neurotology. A Specific Issue and Its Solution. A New Procedure for Bone Reconstruction in OTO-Microsurgery: A Mixture of Bone Dust and Fibrinogen Adhesive, Laryngoscope, 1985, pp. 1278-1280, vol. 95.

Ghadially, J.A. and Ghadially, F.N., Evidence of Cartilage Flow in Deep Defects in Articular Cartilage, Virchows Arch B. Cell Path, 1975, pp. 193-204, vol. 18.

Ghadially, J.A. et al, Long-Term Results of Deep Defects in Articular Cartilage, Virchows Arch B. Cell Path, 1977, pp. 125-136, vol. 25.

Ghazavi, M.T. et al, Fresh Osteochondral Allografts for Post-Traumatic Osteochondral Defects of the Knee, JBJS, 1997, pp. 1008-1013, vol. 79-B.

Gibson, T. et al, The Long-Term Survival of Cartilage Homografts In Man, British Journal of Plastic Surgery, 1958, pp. 177-187, vol. 11.

Gooding, C.R. et al, Abstract only of A prospective, randomised study comparing two techniques of autologous chondrocyte implantation for osteochondral defects in the knee: Periosteum covered versus type I/III collagen covered, Knee, 2006, pp. 203-210, vol. 13, No. 3.

Greco, F. et al, Experimental Investigation into Reparative Osteogenesis With Fibrin Adhesive, Arch Orthop Trauma Surg, 1988, pp. 99-104, vol. 107.

Hamra, S.T., Crushed Cartilage Grafts over Alar Dome Reduction in Open Rhinoplasty, Plast Reconstr Surg., 1993, pp. 352-356, vol. 92, No. 2.

Hangody, L. et al, English Abstract only, Autogenous Osteochondralf Craft Technique for Replacing Knee Cartilage Defects in Dogs, Autogenous Osteochondral Mosaicplasty, Orthop Int, 1997, pp. 175-181, vol. 5, No. 3.

Hangody, L. and Fules, P., Autologous Osteochondral Mosaicplasty for the Treatment of Full-Thickness Defects of Weght-Bearing Joints: Ten Years of Experimental and clinical Experience, JBJS, 2003, pp. 25-32, vol. 85.

Hangody, L. et al, Mosaicplasty for the Treatment of Articular Defects of the Knee and Ankle, Clin Orthopaedics and Rel Res, 2001, pp. S328-S336, No. 391S.

Harbin, M. and Moritz, A.R., Autogenous Free Cartilage Transplanted into Joints, Archives of Surgery, 1930, pp. 885-896, vol. 20, No. 6.

He, Q. et al, Repair of flexor tendon defects of rabbit with tissue engineering method, Chinese Journal of Traumatology, 2002, pp. 200-208, vol. 5, No. 4.

Helidonis, E. et al, Laser Shaping of Composite Cartilage Grafts, Am. J. Otolaryngology, 1993, pp. 410-412, vol. 14, No. 6.

Homminga, G.N. et al, Perichondral Grafting for Cartilage Lesions of the Knee, British Editorial Society of Bone and Joint Surgery, 1990, pp. 1003-1007, vol. 72B.

Homminga, G.N., Repair of Chrondral Lesions of the Knee with a Perichondrial Graft, Fibrin Sealant in Operative Medicine-Orthopedic Surgery Maxillofacial Surgery, 1986, pp. 61-69, vol. 4, Springer-Verlag, Berlin Heidelberg.

Hoover, N. W. et al, Skin Arthroplasty of the Hip, An Experimental Study in Dogs, JBJS, 1961, pp. 1155-1166, vol. 43-A, No. 8.

Horas, U. et al, Autologous Chondrocyte Implantation and Osteochondral Cylinder Transplantation in Cartilage Repair of the Knee Joint: A Prospective, Comparative Trial, JBJS, 2003, pp. 185-192, vol. 85.

Horton, W.A. et al, Characterization of a type II collagen gene (COL2A1) mutation identified in cultured chondrocytes from human hypochondrogenesis, PNAS, 1992, pp. 4583-4587, vol. 89.

Hunziker, E.B., Articular cartilage repair: basic science and clinical progress. A review of the current status and prospects, Osteoarthritis and Cartilage, 2001, pp. 432-463, vol. 10.

Hurtig, M.B. et al, Effects of Lesion Size and Location on Equine Articular Cartilage Repair, Can J. Vet Res, 1988, pp. 137-146, vol. 52.

Hurtig, M.B., Use of autogenous cartilage particles to create a model of naturally occurring degenerative joint disease in the horse, Equine Vet J Suppl, 1988, pp. 19-22, No. 6.

Imhoff, A.B., et al, English Abstract only of Autologous Osteochondral transplantation on various joints, Orthopade, 1999, pp. 33-44, vol. 28, No. 1.

Ishida, T., English Abstract only of The Use of a Fibrin Adhesive for a Cartilage Graft Basic and Clinical Studies, Japanese J. of Plastic and Reconstructive Surgery, 1990, pp. 215-230, vol. 33, No. 1.

Ishizaki, Y. et al, Autocrine Signals Enable Chondrocytes to Survive in Culture, J. Cell Biol. 1994, pp. 1069-1077, vol. 126, No. 4.

Ito, Y. et al, Localization of chondrocyte precursors in periosteum, Osteoarthritis and Cartilage, 2001, pp. 215-223, vol. 9.

Ittner, G. et al, English Abstract only of Treatment of flake fracture of the talus, Z. Orthop Ihre Grenzgeb, 1989, pp. 183-186, vol. 127, No. 2.

Jakob, R.P. et al, Autologous Osteochondral Grafting in the Knee: Indication, Results and Reflections, Clinical Orthopaedics and Rel Res, 2002, pp. 170.184, No. 401.

Jin, C.Z. et al, Human Amniotic Membrane as a Delivery Matrix for Articular Cartilage Repair, Tissue Engineering, 2007, pp. 693-702, vol. 13, No. 4.

Johnson, L.L., Arthroscopic Abrasion Arthroplasty Historical and Pathologic Perspective: Present Status, Arthroscopy: The Journal of Arthroscopic and Related Surgery, 1986, pp. 54-69, vol. 2, No. 1.

Kanzaki, J. et al, Use of Fibrin Glue in Intracranial Procedures Following Acoustic Neuroma Surgery: Application in Facial Nerve Reconstruction and Prevention of Cerebrospinal Fluid Rhinorrhea, Fibrin Sealing in Surgical and Nonsurgical Fields-Neurosurgery Ophthalmic Surgery Ent, 1994, pp. 162-168, vol. 5, Springer-Verlag, Berlin Heidelberg.

Kaplonyi, G. et al, The use of fibrin adhesive in the repair of chondral and osteochondral injuries, Injury, 1988, pp. 267-272, vol. 19.

Kawamura, M. and Urist, M.R., Human Fibrin Is a Physiologic Delivery System for Bone Morphogenetic Protein, Clin Ortho Rel Res, 1988, pp. 302-310, No. 235.

Keller, J. et al, Fixation of osteochondral fractures, Acta Orthop Scand, 1985, pp. 323-326, vol. 56.

Kettunen, K.O., Skin Arthroplasty In The Light Of Animal Experiments With Special Reference To Functional Metaplasia of Connective Tissue, Acta Ortho Scand, 1958, pp. 9-69, Suppl. XXIX.

Kirilak, Y. et al, Fibrin sealant promotes migration and proliferation of human articular chondrocytes: possible involvement of thrombin and protease-activated receptors, Int. J. Mol. Med, 2006, pp. 551-558, vol. 17, No. 4.

Knutsen, G. et al, Autologous Chondrocyte Implantation Compared with Microfracture in the Knee. A Randomized Trial, JBJS, 2004, pp. 455-464, vol. 86.

Kon, E. et al, Second Generation Issues in Cartilage Repair, Sports Med Arthrosc Rev., 2008, pp. 221-229, vol. 16.

Korhonen, R.K. et al, Importance of the superficial tissue layer for the indentation stiffness of articular cartilage, Medical Eng. Phys, 2002, pp. 99-108, vol. 24.

Lane, J.M. et al, Joint Resurfacing in the Rabbit Using an Autologous Osteochondral Graft, JBJS, 1977, pp. 218-222, vol. 59-A, No. 2.

Wagner, P.D. and Westen, E., et al, Improved blood buffering in high-altitude natives?, J Appl Physiol, 2002, pp. 2214-2215, vol. 93.

Wakitani, S., et al, Repair of Rabbit Articular Surfaces With Allograft Chondrocytes Embedded in Collagen Gel, JSJS, 1989, pp. 74-80, vol. 71-B.

Wei, X., et al, The Effect of Sodium Selenite on Chondrocytes in Monolayer Culture, Arthritis and Rheumatism, 1986, pp. 660-664, vol. 29, No. 5.

Welsh, F., The alar cartilage morseler: a new instrument, Br. J. Plastic Surgery, 1983, pp. 483-484, vol. 36.

Wilfilingseder, P., Cranioplasties by means of diced cartilage and split rib grafts, Min Chir, 1983, pp. 837-843, vol. 38, No. 12.

Wischhofer, E., et al, English abstract only of The Behaviour of Autologous Spongiosa Transplants from the Dial Crest With and Without Fibrinadhesive in the Canine Femoral Epiphysis, Unfallheilkunde, 1982, ppl. 250-252, vol. 85.

Xu, J.W. et al, Injectable Tissue-Engineered Cartilage with Different Chondrocyte Sources, Plast. Reconstr. Surg., 2004, pp. 1361-1371, vol. 113.

Yamamoto, E. et al, Use of Micro-Sliced Homograft Cartilage Plates in Tympanoplasty, Acta Otolaryngol, 1985, pp. 123-129, vol. 419.

Yamashita, F. et al, The Transplantation of an Autogeneic Osteochondral Fragment for Osteochondritis Dissecans of the Knee, Clin Ortho Rel Res, 1985, pp. 43-50, vol. 201.

Yilmaz, S. et al, Viability of Diced, Crushed Cartilage Grafts and the Effects of Surgicel (Oxidized Regenerated Cellulose) on Cartilage Grafts, Plast. Reconstru. Surg. 2001, pp. 1054-1060, vol. 108.

Young, F., Autogenous Cartilage Grafts, An Experimental Study, Surgery, 1941, pp. 7-20, vol. 10.

Young, F., The use of autogenous rib cartilage grafts to repair surface defects in dog joints, Surgery, 1940, pp. 254-263, vol. 7.

Zahn, F., On the Fate of Tissues Implanted in the Organism, Int. Med. Congr. in Geneva, Biology Section—Meeting of Sep. 11, 1877, pp. 1-4.

Zalzal, G.H. et al, Cartilage Grafts-Present Status, Head and Neck Surgery, 1986, pp. 363-374, vol. 8.

Zilch, V.H. and Talke, M., Gluing Small Osteochondral Fragments with Fibrin Glue in Hand Surgery. Clinical Experiences, Handchirurgie, 1980, pp. 77-81, vol. 12.

Zilch, V.H., Animal Experiments Investigating the Fixation of Small Osteochondral Fragments by Means of Fibrin Glue, Handchirurgie, 1980, pp. 71-75, vol. 12.

Zilch, H. and Friedebold, G., English summary only of Fixing of Osteochondral Fragments with Fibrinogen Clue. Clinical Experiences, Akt. Traumatol., 1981, pp. 136, vol. 11.

Zilch, H. and Talke, M., English summary only of Fibrin sealant in cases of little osteochondral fragments of the upper limb, Ann. Chir. Main, 1987, pp. 173-176, vol. 6, No. 2.

Zilch, H. and Talke, M., English summary only of Fixation of Small Osteochondral Fragments with the Fibrinogen Adhesive, Clinical Report, Ann. Chir. Main, 1980, pp. 77-81, vol. 12.

Adkisson, H.D., IV et al, In Vitro Generation of Scaffold Independent Neocartilage, Clin Ortho Rel Res, 2001, pp. S280-S294, No. 391S.

Caruso, E. et al, Repopulation of Laser-Perforated Chondroepiphyseal Matrix with Xenogeneic Chondrocytes: An Experimental Model, JBJS, 1996, pp. 102-107, vol. 14.

Cheng, N.C. et al, Chondogenic Differentiation of Adipose-Derived Adult Stem Cells by a Porous Scaffold Derived from Native Articular Cartilage Extracellular Matrix, Tissue Engineering, Part A, 2009, pp. 231-241, vol. 15, No. 2.

Davis, J.S., Some of the Problems of Plastic Surgery, Ann Surg., 1917, pp. 88-94, vol. 66, No. 1.

Davis, W.B. and Gibson, T., Absorption of Autogenous Cartilage Grafts In Man, British Journal of Plastic Surgery, 1957, pp. 177-185, vol. 9.

Gelse, K. et al, Paracrine Effect of Transplanted Rib Chondrocyte Spheroids Supports Formation of Secondary Cartilage Repair Tissue, J. Ortho Res, 2009, pp. 1216-1225, vol. 27.

Hendrickson, D.A. et al, Chondrocyte-Fibrin Matrix Transplants for Resurfacing Extensive Articular Cartilage Defects, J. Ortho Res, 1994, pp. 485-497, vol. 12 No. 4.

Homminga, G.N. et al, Chondrocyte behavior in fibrin glue in vitro, Acta Orthop Scand, 1993, pp. 441-445, vol. 64, No. 4.

Howard, R.D., et al, Long-term fate and effects of exercise on sternal cartilage autografts used for repair of large osteochondral defects in horses, Am J Vet Res, 1994, pp. 1158-1167, vol. 55, No. 8.

Hutchinson, J., Observations on bone transplants in the anterior chamber of the eye, Glasgow Med J., 1949, pp. 357-363, vol. 30, No. 10.

Jeffries, D.J.R., and Evans, P.H.R., Cartilage regeneration following septal surgery in young rabbits, J. Laryngology and Otology, 1984, pp. 577-583, vol. 98.

Gu, J.D., et al, True Denisity of Normal and Enzymatically Treated Bovine Articular Cartilage, Trans Orthop Res Soc., 1999, pp. 642, vol. 24.

Kim, M.K. et al, Autologous chondrocyte implantation in the knee using fibrin, Knee Surg. Sports Traumatol. Arthrosc., 2010, pp. 528-534, vol. 18.

Libera, J., et al, Cartilage Engineering, Fundamentals of Tissue Engineering and Regenerative Medicine, 2009, pp. 233-242, Chapter 18, Springer-Verlag, Berlin Heidelberg.

Liu, X., et al, In vivo ectopic chondrogenesis of BMSCs directed by mature chondrocytes, Biomaterials, 2010, pp. 9406-9414, vol. 31.

Longacre, J.J. et al, Further observations of the behavior of autogenous split-rib grafts in reconstruction of extensive defects of the cranium and face, Plas Reconstr Surg, 1957, pp. 281-296, vol. 20, No. 4.

Marmotti, A., et al, One-Step osteochondral repair with cartilage fragments in a composite scaffold, Knee Surg Sports Traumatol Arthrosc., Feb 21, 2012, [Epub ahead of print], 12 pages.

McKibbin B. and Holdsworth, F.W., The dual nature of epiphysial cartilage, J Bone Joint Surg Br., 1967, pp. 351-361, vol. 49, No. 2.

Medawar, P.B., Immunity to homologous grafted skin; the fate of skin homografts transplanted to the brain, to subcutaneous tissue, and to the anterior chamber of the eye, Br J Exp Pathol., 1948, pp. 58-69, vol. 29, No. 1.

Munirah, S. et al, Articular cartilage restoration in load-bearing osteochondral defects by implantation of autologous chondrocyte-fibrin constructs: an experimental study in sheep, J Bone Joint Surg Br., 2007, pp. 1099-1109, vol. 89, No. 8.

Nehrer, S. et al, Three-year clinical outcome after chondrocyte transplantation using a hyaluronan matrix for cartilage repair, Eur J Radiol., 2006, pp. 3-8, vol. 57, No. 1.

Obradovic, B., et al, Integration of engineered cartilage, J Orthop Res., 2001, pp. 1089-1097, vol. 19, No. 6.

Verwoerd, C.D.A. et al, Stress and woundhealing of the cartilaginous nasal septum, Acta Otolaryngol., 1989, pp. 441-445, vol. 107, No. 5-6.

Pierce, A. et al, Surgicel: macrophage processing of the fibrous component, Int J Oral Maxillofac Surg., 1987, pp. 338-345, vol. 16, No. 3.

Roemhildt, M.L. et al, Material properties of articular cartilage in the rabbit tibial plateau, J. Biomech, 2006, pp. 2331-2337, vol. 39, No. 12.

Schubert, T. et al, Long-term effects of chondrospheres on cartilage lesions in an autologous chondrocyte implantation model as investigated in the SCID mouse model, International Journal of Molecular Medicine, 2009, pp. 455-460, vol. 23.

Selktar, D., Lecture Bulletin Nature's Healing Matrix, Technion Focus, May 2006, 1 page.

Silverman, R.P., et al, Adhesion of Tissue-Engineered Cartilage to Native Cartilage, Plast. Reconstr Surg, 2000, pp. 1393-1398, vol. 105.

Sin, Y.M. et al, Studies on the mechanism of cartilage degradation, J Pathol., 1984, pp. 23-30, vol. 142, No. 1.

Van Susante, J.L.C. et al, Resurfacing potential of heterologous chondrocytes suspended in fibrin glue in large full-thickness defects of femoral articular cartilage: an experimental study in the goat, Biomaterials, 1999, pp. 1167-1175, vol. 20, No. 13.

Dupertuis, S.M., Growth of Young Human Autogenous Cartilage Grafts, Plast Reconstr Surg, 1946, pp. 486-493, vol. 5, No. 6.

Albrecht, F. et al, Closure of Osteochondral Lesions Using Chondral Fragments and Fibrin Adhesive, Arch Orthop Trauma Surg, 1983, pp. 213-217, vol. 101.

Albrecht, F., English Abstract of German article Closure of joint cartilage defects using cartilage fragments and fibrin glue, Fortschr Med., 1983, pp. 1650-1652, vol. 101, No. 37.

Dupertuis, S.M., Actual Growth of Young Cartilage Transplants in Rabbits, Archives of Surgery, 1941, pp. 32-63, vol. 43.

Eberlin, J.L. et al, Osteocartilagenous Reconstruction, Plastic Surgery Nerve Repair Burns, Fibrin Sealing in Surgical and Nonsurgical Fields, 1995, pp. 20-24, vol. 3 Springer-Verlag, Berlin, Heidelberg.

De Kleine, E.H., The Chondrojet, A Simplified Method for Handling of Diced Cartilage, Plast Reconstr Surg, 1946, pp. 95-102, vol. 3, No. 1.

Aston, J.E. and Bentley G., Repair of Articular Surfaces By Allografts of Articular and Growth-Plate Cartilage, J Bone Joint Surg Br., 1986, pp. 29-35, vol. 68, No. 1.

Bacsich, P. and Wyburn, G.M., XXXVIII. The Significance of the Mucoprotein Content on the Survival of Homografts of Cartilage and Cornea, 1947, P.R.S.E., pp. 321-327, vol. LXII, B, Part III.

Bayliss, M.T. and Roughley, P.J., The properties of proteoglycan prepared from human articular cartilage by using associative caesium chloride gradients of high and low starting densities, Biochem. J., 1985, pp. 111-117, vol. 232.

Bently, G. and Greer, R.B. III, Homotransplantation of Isolated Epiphyseal and Articular Cartilage Chondrocytes into Joint Surfaces of Rabbits, Nature, 1971, pp. 385-388, vol. 230.

Berlet, G.C. et al, Treatment of Unstable Osteochondritis Dissecans Lesions of the Knee Using Autogenous Osteochondral Grafts (Mosaicplasty), J. Arthroscopic and Related Surgery, 1999, pp. 312-316, vol. 15, No. 3.

Decher, H., Reduction of Radical Cavities by Means of Homologous Cartilage Chips, Larying. Rhinol. Otol., 1985, pp. 423-426, vol. 64.

Bodo, G. et al, Arthroscopic Autologous Osteochondral Mosaicplasty for the Treatment of Subchondral Cystic Lesion in the Medial Femoral Condyle in a Horse, Acta Veterinaria Hungarica, 2000, pp. 343-354, vol. 48, Vo. 3.

Craigmyle, M.B.L., Cellular Survival in Long-Term Cartilage Grafts in the Rabbit, Transplantation Bulletin, 1958, pp. 123, vol. 5, No. 1.

Craigmyle, M.B.L., An Autoradiographic and Histochemical Study of Long-Term Cartilage Grafts in the Rabbit, J. of Anatomy, 1954, pp. 467-473, vol. 92, Part 3.

Coster, D.J. and Galbraith, J.E.K., Diced cartilage grafts to correct enophthalmos, British J. Ophthalmology, 1980, pp. 135-136, vol. 64.

Cooke, M.E. et al, Manuscript entitled Structured three-dimensional co-culture of mesenchymal stem cells with chondrocyts promotes chondrogenic differentiation without hypertrophy, pp. 1-19.

Chesterman, P.J. et al, Homotransplantation of Articular Cartilage and Isolated Chondrocytes, An Experimental Study in Rabbits, JBJS, 1968, pp. 184-197.

Breadon, G.E., et al, Autografts of Uncrushed and Crushed Bone and Cartilage, Bone and Cartilage Autografts, 1979, pp. 75-80, vol. 105.

Brighton, C.T., et al, Articular Cartilage Preservation and Storage I. Application of Tissue Culture Techniques to the Storage of Viable Articular Cartilage, Arthritis Rheum., 1979, pp. 1093-1101, vol. 22, No. 10.

Brittberg, M. et al, Treatment of Deep Cartilage Defects in the Knee With Autologous Chondrocyte Transplantation, The New England Journal of Medicine, 1994, pp. 889-895, vol. 331, No. 14.

Brittberg, M. Autologous Chondrocyte Transplantation, Clinical Orthopaedics and Related Research, 1999, pp. S147-S155, No. 367S.

Brittberg, M. et al, Treatment of Deep Cartilage Defects in the Knee with Autologous Chondrocyte Transplantation, N Engl J Med., 1994, pp. 889-895, vol. 331, No. 14.

Brodkin, H.A. and Peer, L.A., Diced Cartilage for Chest Wall Defects, 1954, pp. 97-102, vol. 28, No. 1.

Brown, B.L. et al, Transplantation of Fresh Allografts (Homografts) of Crushed and Uncrushed Cartilage and Bone: A 1-Year Analysis in Rabbits, The Laryngoscope, 1980, pp. 1521-1532, vol. 90.

Bruns, J. et al, Long-Term Follow up Results after Gluing Osteochondral Fragments in Patients with Osteochondrosis Dissecans Langenbecks Arch Chir, 1993, pp. 160-166, vol. 378.

Bruns, J. et al, Autologous rib perichondrial grafts in experimentally induced osteochondral lesions in the sheep-knee joint: morphological results, Virchows Archiv A. Pathol Anat, 1992, pp. 1-8, vol. 421.

Bruns, J. and Henne-Bruns, D., Autologous Perichondrial Transplantation for the Repair of Experimentally Induced Cartilage Defects in the Sheep Knee—Two Glueing Techniques, Orthopedic Surgery Maxillofacial Surgery, Fibrin Sealing in Surgical and Nonsurgical fields, Oct. 27, 1994, pp. 50-60, Springer, Berlin, Heidelberg.

Buckwalter, J.A., Articular Cartilage Injuries, Clinical Orthopaedics and Related Research, 2002, pp. 21-37, vol. 402.

Bujia, J. et al, Culture and Cryopreservation of Chondrocytes from Human Cartilage Relevance for Cartilage Allografting in Otolaryngology, ORL, 1992, pp. 80-84, vol. 54.

Bujia, J., Determination of the Viability of Crushed Cartilage Grafts: Clinical Implications for Wound Healing in Nasal Surgery, Ann Plast Surg, 1994, pp. 261-265, vol. 32.

Cherubino, P. et al, Autologous chondrocyte implantation using a bilayer collagen membrane: A preliminary report, J. Ortho Surg, 2003, pp. 10-15, vol. 11, No. 1.

Calandruccio, R. A. and Gilmer, W.S., Proliferation, Regeneration, and Repair of Articular Cartilage of Immature Animals, JBJS, 1962, pp. 431-455, vol. 44A, No. 3.

Chen, F.S. et al, Repair of Articular Cartilage Defects: Part II. Treatment Options, Am. J. Ortho, 1999, pp. 88-96.

Passl, R. and Plenk, H. Jr, Histological observations after replantation of articular cartilage, Unfallchirurgie, 1986, pp. 194-199, vol. 12, No. 4.

Passl, R. and Plenk, H. Jr, Fibrin Sealing of Cartilage Surfaces, Beitr. Orthop. Traumatol, 1989, pp. 503-507, vol. 36, No. 10.

Pech, A., et al, Tissuecol in Septorhinoplasties, Ann. Oto-Laryng., 1988, pp. 629-634, vol. 105.

Peer, L.A., Extended Use of Diced Cartilage Grafts, Meeting of the American Association of Plastic Surgeons, Apr. 21, 23, 1954, pp. 178-185.

Peer, LA., The Fate of Living and Dead Cartilage Transplanted in Humans, Surg, Gynec, and Obst., 1939, pp. 603-610, vol. 68.

Peer, L.A., Fate of Autogenous Septal Cartilage After Transplantation in Human Tissues, Archv of Otolaryngology, 1941, pp. 696-709, vol. 34, No. 4.

Peer, LA., The Neglected Septal Cartilage Graft (With Experimental Observations on the Growth of Human Cartilage Grafts), Arch Otolaryngol Head Neck Surg.,1945, pp. 384-396, vol. 42, No. 5.

Peretti, G.M. et al, Bonding of Cartilage Matrices with Cultured Chondrocytes: An Experimental Model, J. Orthopaedic Res, 1998, pp. 89-95, vol. 16.

Peretti, G.M. et al, Biomechanical Analysis of a Chondrocyte-Based Repair Model of Articular Cartilage, Tissue Engineering, 1999, pp. 317-326, vol. 5, No. 4.

Peretti, G.M. et al, Cell-Based Tissue-Engineered Allogeneic Implant for Cartilage Repair, Tissue Engineering, 2000, pp. 567-576, vol. 6, No. 5.

Peretti, G.M. et al, Cell-Based bonding of articular cartilage: An extended Study, J. Biomed Mater Res, 2003, pp. 517-524, vol. 64A.

Peretti, G.M. et al, In vitro bonding of pre-seeded chondrocytes, Sport Sci Health, 2007, pp. 29-33, vol. 2.

Phemister, D.B. and Miller, E.M., The Method of New Joint Formation in Arthroplasty, Surgery, Gynecology and Ostetrics, 1918, pp. 406-447, vol. 26.

Pierce, G.W. and O'Connor, G.B., XXXVI. Reconstruction Surgery of the Nose, Ann. Otol. Rhin. And Laryng., 1938, pp. 437-452, vol. 47.

Piragine, F. et al, Use of Bovine Heterologous Cartilage and Fibrin Sealant in Middle Ear Reconstructive Surgery, Neurosurgery Ophthalmic Surgery ENT, Fibrin Sealing in Surgical and Nonsurgical Fields, 1994, pp. 193-198, vol. 5, Springer-Verlag, New York, USA.

Pitman, M.I. et al, the Use of Adhesives in Chondrocyte Transplantation Surgery: In-Vivo Studies, Bull Hosp Jt Dis Orthop Inst., 1989, pp. 213-220, vol. 49, No. 2.

Plaga, B.R. et al, Fixation of osteochondral fractures in rabbit knees. A comparison of Kirschner wires, fibrin sealant, and polydioxanone pins, J Bone Joint Surg Br., 1992, pp. 292-296, vol. 74, No. 2.

Plenk, H. Jr and Passl, R., Trans- and Replantation of Articular Cartilage Using the Fibrinogen Adhesive System, Gastpar, H. (ed.): Biology of the articular cartilage in health and disease, 1980, pp. 439-447, Schattauer, Stuttgart- New York, USA.

Plenk, H. Jr and Passl, R., Articular Cartilage Transplants in Experiments and Clinical Practice, ACA, Acta Chirurgica Austriaca 21st Seminar of the Austrian Association of Surgical Research, Nov. 13 to 15, 1997, pp. 1-4, vol. 29, Suppl. No. 137.

Pridie, K.H., A method of resurfacing osteoarthritic knee joints, JBJS, 1959, pp. 618-619, vol. 41B, No. 3.

Prin, A. et al, Effect of purified growth factors on rabbit articular chondrocytes in Monolayer Culture, I. DNA Synthesis, Arthritis & Rheumatism, 1982, pp. 1217-1227, vol. 25, No. 10.

Prudden, T., Article IV., Experimental Studies on the Transplantation, American Journal of the Medical Sciences: Oct. 1881, pp. 360-370, vol. 82, No. 164.

Vachon, A., et al, Neochondrogenesis in free intra-articular, periosteal, and perichondrial autografts in horses, Am J Vet Res, 1989, pp. 1787-1794, vol. 50, No. 10.

Redl, H. et al, Methods of Fibrin Seal Application, Thorac. Cardiovasc. Surgeon, 1982, pp. 223-227, vol. 30.

Roberts, S. et al, Autologous chondrocyte implantation for cartilage repair: monitoring its success by magnetic resonance imaging and histology, Arthritis Res and Therapy, 2003, pp. R60-R73, vol. 5.

Robinson, D. et al, Regenerating hyaline cartilage in articular defects of old chickens using implants of embryonal chick chondrocytes embedded in a new natural delivery substance, Calcif Tissue Int., 1990, pp. 246-253, vol. 46, No. 4.

Ruano-Ravina, A. and Diaz, M.J., Autologous chondrocyte implantation: a systematic review, Osteoarthritis and Cartilage, 2006, pp. 47-51, vol. 14.

Rudderman, R.H., et al, The Fate of Fresh and Preserved, Noncrushed and Crushed Autogenous Cartilage in the Rabbit Model, Ann Plast Surg, 1994, pp. 250-254, vol. 32.

Rupp, G. et al, Fibrin Adhesion of Transposed Autologous Cartilage Bone Grafts to Repair Knee-Joint Defects, Langenbeck's Archives of Surgery, 1978, pp. 676-677, vol. 347, No. 1.

Saidi, K. et al, Articular Knee Transplant in the Rabbit: Experimental Study and Clinical Projections, Union Medicale du Canada, 1971, pp. 88-99, vol. 100, No. 1.

Salter, R.B., et al, The Biological Effect of Continuous Passive Motion on the Healing of Full-Thickness Defects in ARticular Cartilage, JBJS, 1980, pp. 1232-1251, vol. 62-A, No. 8.

Sampath, T.K., et al, In vitro transformation of mesenchymal cells derived from embryonic muscle into cartilage in response to extracellular matrix components of bone, Proc Natl Acad Sci U S A, 1984, pp. 3419-3423, vol. 81, No. 11.

Schlag, G. and Redl, H., Fibrin Sealant in Orthopedic Surgery, Clin Ortho Rel Res, 1988, pp. 269-285, vol. 227.

Schlag, G. and Redl, H., Fibrin adhesive system in bone healing, Acta Orthop Scand., 1983, pp. 655-658, vol. 54, No. 4.

Schobel, H., Compound Prosthesis and Cartilage Layer: Two New Applications of Fibrin Sealing in Reconstructive Middle Ear Surgery, Neurosurgery Ophthalmic Surgery ENT, Fibrin Sealing in Surgical and Nonsurgical Fields, 1994, pp. 186-192, vol. 5, Springer-Verlag, New York, USA Schreiber, R.E. et al, A Method for Tissue Engineering of Cartilage by Cell Seeding on Bioresorbable Scaffolds, Ann N Y Acad Sci., 1999, pp. 398-404, vol. 875.

Schwam, B.L., Human Amniotic Membrane Transplantation for the Treatment of Ocular Surface Disease, Northeast Florida Medicine Journal, http://www.dcmsonline.org/jax-medicine/2002journals/augsept2002/amniotic.htm, 2002, print date Mar. 3, 2009, pp. 1-7.

Schwartz, E.R., et al, Sulfate Metabolism in Human Chondrocyte Cultures, J. Clin Investigation, 1974, pp. 1056-1063, vol. 54.

Schwarz, N., et al, The Influence of Fibrin Sealant on Demineralized Bone Matrix-Dependent Osteoinduction, Clin Ortho Rel Re, 1989, pp. 282-287, No. 238.

Shoemaker, S. et al, Effects of fibrin sealant on incorporation of autograft and xenograft tendons within bone tunnels. A preliminary study, JAm J Sports Med., 1989, pp. 318-324, vol. 17, No. 3.

Silverman, R.P., et al, Injectable Tissue-Engineered Cartilage Using a Fibrin Glue Polymer, American Society of Plastic Surgeons, 1999, pp. 1809-1818, vol. 103, No. 7.

Simms, G.F., et al, Diced Homologous Cartilage in Hernioplasty, Jour. Med. Soc. J.J., 1952, pp. 406-407, vol. 49, No. 9.

Sosna, A. and Vavra, J., Use of Fibrin Glue in Orthopedics, Acta Chir. Orthop. Traum., 1984, pp. 8-91, vol. 51, No. 2.

Specchia, N. et al, Fetal chondral homografts in the repair of articular cartilage defects, Blletin Hospital for Joint Diseases, 1996, pp. 230-235, vol. 54, No. 4.

Stoksted, P. and Ladefoged, C., Crushed cartilage in nasal reconstruction, J. Laryngology and Otology, 1986, pp. 897-906, vol. 100.

Tanaka, H. et al, A Study on Experimental Homocartilage Transplantation, Arch Orthop Traumat Surg, 1980, pp. 165-169, vol. 96.

Tanaka, H. and Shinno, N., Histochemical Studies on Regeneration of Articular Cartilage, Tokushima J Exp Med., 1971, pp. 63-73, vol. 18.

Temenoff, J.S. and Mikos, A.G., Review: Tissue engineering for regeneration of articular cartilage, Biomaterials, 2000, pp. 431-440, vol. 21, No. 5.

Tuan, R.S., A second-generation autologous chondrocyte implantation approach to the treatment of focal articular cartilage defects, Arthritis Res Ther., 2007, pp. 109 (1-4), vol. 9, No. 5.

Peretti, G.M. et al, A Biomechanical Analysis of an Engineered Cell-Scaffold Implant for Cartilage Repair, 2001, Ann Plast Surg, pp. 533-537, Vol. 46.

"U.S. Appl. No. 10/374,772, 1.132 Declaration of Julia Hwang filed Jan. 5, 2009", 3 pgs.

"U.S. Appl. No. 10/374,772, Response filed Jan. 6, 2009 to Non-Final Office Action mailed Sep. 2, 2008", 5 pgs.

"U.S. Appl. No. 11/010,799, Examiner Interview Summary mailed Apr. 5, 2010", 4 pgs.

"U.S. Appl. No. 11/010,779, Examiner Interview Summart mailed Dec. 7, 2009", 3 pgs.

"U.S. Appl. No. 11/010,779, Non Final Office Action mailed Feb. 17, 2010", 4 pgs.

"U.S. Appl. No. 11/010,779, Non Final Office Action mailed Apr. 15, 2009", 8 pgs.

"U.S. Appl. No. 11/010,779, Notice of Allowance mailed Jul. 8, 2010", 4 pgs.

"U.S. Appl. No. 11/010,779, Response filed Feb. 12, 2009 to Restriction Requirement mailed Jan. 12, 2009", 3 pgs.

"U.S. Appl. No. 11/010,779, Response filed Apr. 19, 2010 to Non Final Office Action mailed Feb. 17, 2010", 13 pgs.

"U.S. Appl. No. 11/010,779, Response filed Jul. 15, 2009 to Non Final Office Action mailed Apr. 15, 2009", 16 pgs.

"U.S. Appl. No. 11/010,779, Response filed Dec. 3, 2009 to Non Final Office Action mailed Apr. 15, 2009", 13 pgs.

"U.S. Appl. No. 11/010,779, Restriciton Requirement mailed Jan. 12, 2009", 16 pgs.

"U.S. Appl. No. 11/613,250, Advisory Action mailed Jul. 9, 2008", 13 pgs.

"U.S. Appl. No. 11/613,250, Final Office Action mailed Apr. 15, 2008", 9 pgs.

"U.S. Appl. No. 11/613,250, Non Office Action mailed Mar. 28, 2011", 9 pgs.

"U.S. Appl. No. 11/613,250, Non Final Office Action mailed May 28, 2009", 12 pgs.

"U.S. Appl. No. 11/613,250, Non Final Office Action mailed Sep. 20, 2007", 17 pgs.

"U.S. Appl. No. 11/613,250, Non Final Office Action mailed Sep. 21, 2010", 15 pgs.

"U.S. Appl. No. 11/613,250, Non Final Office Action mailed Oct. 16, 2008", 11 pgs.

"U.S. Appl. No. 11/613,250, Non Final Office Action mailed Dec. 23, 2009", 15 pgs.

"U.S. Appl. No. 11/613,250, Notice of Allowance mailed Dec. 23, 2011", 9 pgs.

"U.S. Appl. No. 11/613,250, Response filed Jan. 16, 2009 to Non Final Office Action mailed Oct. 16, 2008", 9 pgs.

"U.S. Appl. No. 11/613,250, Response filed Jan. 19, 2011 to Non Final Office Action mailed Sep. 21, 2010", 13 pgs.

"U.S. Appl. No. 11/613,250, Response filed Mar. 23, 2010 to Non Final Office Action mailed Dec. 23, 2009", 9 pgs.

"U.S. Appl. No. 11/613,250, Response filed Jun. 16, 2008 to Final Office Action mailed Apr. 15, 2008", 19 pgs.

"U.S. Appl. No. 11/613,250, Response filed Aug. 28, 2009 to Non Final Office Action mailed May 28, 2009", 12 pgs.

"U.S. Appl. No. 11/613,250, Response filed Sep. 28, 2011 to Non Final Office Action mailed Mar. 28, 2011", 9 pgs.

"U.S. Appl. No. 11/613,250, Reponse filed Dec. 20, 2007 to Non Final Office Action mailed Sep. 20, 2007", 19 pgs.

"U.S. Appl. No. 11/613,319, Advisory Action mailed Jan. 19, 2010", 3 pgs.

"U.S. Appl. No. 11/613,319, Final Office Action mailed Jun. 18, 2012", 11 pgs.

"U.S. Appl. No. 11/613,319, Final Office Action mailed Oct. 26, 2009", 7 pgs.

"U.S. Appl. No. 11/613,319, Information Disclosure Statement mailed Mar. 20, 2007", 9 pgs.

"U.S. Appl. No. 11/613,319, Information Disclosure Statement mailed Jun. 30, 2008", 6 pgs.

"U.S. Appl. No. 11/613,319, Information Disclosure Statement mailed Sep. 3, 2010", 5 pgs.

"U.S. Appl. No. 11/613,319, Information Disclosure Statement mailed Dec. 20, 2007", 6 pgs.

"U.S. Appl. No. 11/613,319, Non Final Office Action mailed Mar. 13, 2009", 7 pgs.

"U.S. Appl. No. 11/613,319, Non Final Office Action mailed Dec. 29, 2011", 9 pgs.

"U.S. Appl. No. 11/613,319, Response filed Jan. 26, 2009 to Restriction Requirement mailed Dec. 26, 2008", 7 pgs.

"U.S. Appl. No. 11/613,319, Response filed Jan. 26, 2010 to Advisory Action mailed Jan. 19, 2010", 9 pgs.

"U.S. Appl. No. 11/613,319, Reponse filed Mar. 29, 2012 to Non Final Office Action mailed Dec. 29, 2011", 15 pgs.

"U.S. Appl. No. 11/613,319, Reponse filed Jun. 11, 2009 to Non Final Office Action mailed Mar. 13, 2009", 8 pgs.

"U.S. Appl. No. 11/613,319, Response filed Sep. 17, 2012 to Final Office Action mailed Jun. 18, 2012", 19 pgs.

"U.S. Appl. No. 11/613,319, Response filed Dec. 7, 2009 to Final Office Action mailed Oct. 26, 2009", 8 pgs.

"U.S. Appl. No. 11/613,319, Restriction Requirement mailed Dec. 26, 2008", 6 pgs.

"U.S. Appl. No. 11/613,456, Advisory Action mailed Aug. 11, 2009", 3 pgs.

"U.S. Appl. No. 11/613,456, Final Office Action mailed Jun. 4, 2009", 7 pgs.

"U.S. Appl. No. 11/613,456, Non Final Office Action mailed Jan. 23, 2009", 6 pgs.

"U.S. Appl. No. 11/613,456, Non Final Office Action mailed Sep. 11, 2009", 5 pgs.

"U.S. Appl. No. 11/613,456, Notice of Allowance mailed Jan. 19, 2010", 5 pgs.

"U.S. Appl. No. 11/613,456, Response filed Apr. 3, 2009 to Non Final Office Action mailed Jan. 23, 2009", 8 pgs.

"U.S. Appl. No. 11/613,456, Response filed Aug. 4, 2009 to Final Office Action mailed Jun. 4, 2009", 9 pgs.

"U.S. Appl. No. 11/613,456, Response filed Nov. 6, 2008 to Restriction Requirement mailed Oct. 7, 2008", 7 pgs.

"U.S. Appl. No. 11/613,456, Response filed Dec. 7, 2009 to Non Final Office Action mailed Sep. 11, 2009", 9 pgs.

"U.S. Appl. No. 11/613,456, Restriction Requirement mailed Oct. 7, 2008", 6 pgs.
"U.S. Appl. No. 12/101,553, Response filed Aug. 15, 2011 to Restriction Requirement mailed Jul. 13, 2011", 11 pgs.
"U.S. Appl. No. 12/101,553, Final Office Action mailed Sep. 14, 2012", 9 pgs.
"U.S. Appl. No. 12/101,553, Final Office Action mailed Dec. 28, 2012", 9 pgs.
"U.S. Appl. No. 12/101,553, Non Final Office Action mailed Nov. 9, 2011", 8 pgs.
"U.S. Appl. No. 12/101,553, Response filed May 9, 2012 to Non Final Office Action mailed Nov. 9, 2011", 14 pgs.
"U.S. Appl. No. 12/101,553, Restriction Requirement mailed Jul. 13, 2011", 17 pgs.
"U.S. Appl. No. 12/751,230, Non Final Office Action mailed Sep. 1, 2010", 9 pgs.
"U.S. Appl. No. 12/751,230, Preliminary Amendment filed Mar. 31, 2010", 7 pgs.
"U.S. Appl. No. 12/751,230, Response filed Jul. 30, 2010 to Restriction Requirement mailed Jul. 21, 2010", 5 pgs.
"U.S. Appl. No. 12/751,230, Restriction Requirement mailed Jul. 21, 2010", 53 pgs.
"U.S. Appl. No. 12/861,404, Non Final Office Action mailed May 16, 2012", 6 pgs.
"U.S. Appl. No. 12/861,404, Preliminary Amendment filed Aug. 23, 2010", 6 pgs.
"U.S. Appl. No. 12/976,689, Non Final Office Action mailed May 17, 2012", 7 pgs.
"U.S. Appl. No. 12/976,711, Examiner Interview Summary mailed Nov. 15, 2012", 3 pgs.
"U.S. Appl. No. 12/976,711, Non Final Office Action mailed Dec. 12, 2012", 9 pgs.
"U.S. Appl. No. 12/976,711, Response filed Aug. 29, 2012 to Restriction Requirement mailed May 29, 2012", 4 pgs.
"U.S. Appl. No. 12/976,711, Response filed Dec. 3, 2012 to Restriction Requirement mailed Oct. 4, 2012", 6 pgs.
"U.S. Appl. No. 12/976,711, Restriciton Requirement mailed May 29, 2012", 6 pgs.
"U.S. Appl. No. 12/976,711, Restriction Requirement mailed Oct. 4, 2012", 6 pgs.
"U.S. Appl. No. 13/327,238, Non Final Office Action mailed Jan. 2, 2013", 8 pgs.
"U.S. Appl. No. 13/327,238, Preliminary Amendment filed Jun. 1, 2012", 6 pgs.
"U.S. Appl. No. 13/327,238, Response filed Dec. 7, 2012 to Restriction Requirement mailed Sep. 7, 2012", 6 pgs.
"U.S. Appl. No. 13/327,238, Restriction Requirement mailed Sep. 7, 2012", 11 pgs.
"U.S. Appl. No. 13/327,265, Final Office Action mailed Jan. 31, 2013", 8 pgs.
"U.S. Appl. No. 13/327,265, Non Final Offie Action mailed Apr. 2, 2012", 10 pgs.
"U.S. Appl. No. 13/327,265, Response filed Sep. 4, 2012 to Non Final Office Action mailed Apr. 2, 2012", 7 pgs.
"U.S. Appl. No. 13/327,265, Non Final Office Action mailed Feb. 7, 2013", 9 pgs.
"U.S. Appl. No. 13/327,265, Preliminary Amendment filed Jun. 1, 2012", 7 pgs.
"U.S. Appl. No. 13/428,873, Response filed Oct. 17, 2012 to Non Final Office Action mailed Jul. 18, 2012", 9 pgs.
"U.S. Appl. No. 13/428,873, Final Office Action mailed Dec. 12, 2012", 6 pgs.
"U.S. Appl. No. 13/428,873, Non Final Office Action mailed Jul. 18, 2012", 9 pgs.
"U.S. Appl. No. 13/428,873, Preliminary Amendment filed Mar. 23, 2012", 6 pgs.
"Application Serial No. 2008240191, First Examination Report mailed Sep. 21, 2012".
"Australian Application Serial No. 2006282754, Office Action mailed Nov. 8, 2011", 3 pgs.
"European Application Serial No. 04813849.9, Extended European Search Report mailed Apr. 8, 2008", 3 pgs.
"European Application Serial No. 04813849.9, Office Action mailed Feb. 16, 2009", 5 pgs.
"European Application Serial No. 04813849.9, Response filed Aug. 20, 2009 to Office Action mailed Feb. 16, 2009", 18 pgs.
"European Application Serial No. 07862720.5, Notice of Allowance mailed Feb. 25, 2011", 6 pgs.
"European Application Serial No. 07862720.5, Office Action mailed Feb. 26, 2010", 3 pgs.
"European Application Serial No. 07862720.5, Response filed Sep. 1, 2010 to Office Action mailed Feb. 26, 2010", 10 pgs.
"European Application Serial No. 11154746.9, Response filed Dec. 14, 2012 to Office Action mailed Nov. 15, 2012", 4 pgs.
"European Application Serial No. 11154746.9, Search Report mailed May 23, 2011", 4 pgs.
"European Application Serial No. 11154747.7, Response filed Dec. 14, 2012 to Office Action mailed Nov. 21, 2012", 4 pgs.
"European Application Serial No. 11154747.7, Search Report mailed May 23, 2011", 4 pgs.
"European Application Serial No. 11154748.5, Search Report mailed May 24, 2011", 4 pgs.
"International Application Serial No. PCT/US2008/60078, International Search Report mailed Sep. 3, 2008", 1 pg.
"International Application Serial No. PCT/US2004/041591, Written Opinion mailed Jun. 12, 2006", 4 pgs.
"International Application Serial No. PCT/US2006/33687, International Preliminary Report on Patentability mailed Feb. 26, 2008", 7 pgs.
"International Application Serial No. PCT/US2006/33687, Written Opinion mailed Aug. 8, 2007", 6 pgs.
"International Application Serial No. PCT/US2007/025252, International Preliminary Report on Patentability mailed Jun. 23, 2009", 8 pgs.
"International Application Serial No. PCT/US2007/025252, International Search Report mailed Aug. 18, 2008", 3 pgs.
"International Application Serial No. PCT/US2007/025252, International Search Report mailed Apr. 18, 2008", 3 pgs.
"International Application Serial No. PCT/US2007/025252, Written Opinion mailed Apr. 18, 2008", 7 pgs.
"International Application Serial No. PCT/US2007/086468, International Preliminary Report on Patentability mailed Jun. 23, 2009", 10 pgs.
"International Application Serial No. PCT/US2007/086468, International Search Report Jun. 5, 2008", 4 pgs.
"International Application Serial No. PCT/US2007/086468, Written Opinion mailed Jun. 20, 2009", 9 pgs.
"Japanese Application Serial No. 2008-528250, Office Action mailed Jun. 22, 2012", 5 pgs.
"Japanese Application Serial No. 2008-528250, Response filed Nov. 22, 2012 to Office Action mailed Jun. 22, 2012", 9 pgs.
Alston, et al., "New Method to prepare autlogous fibron glue on demand", Translational Research vol. 149, (2007), 187-195.
Chang, et al., "Cartilage-Derived Morphogenetic Proteins", J. Biol. Chem., 269, (1994), 28227-28234.
Convery, F.R., et al., "The Repair of Large Osteochondral Defects", An Experimental Study in Horses, Clin. Orthrop. 82., (1972), 253-262.
Craigmyle, M B, "Studies of Cartilage autografts and homografts in the rabbit", British Journal of Plastic Surgery 8 , (1955), 93-100.
Didier, R, et al., "Production de cartilage et d'os, au sein de greffes vivantes et mortes, chez le lapin", Comptes Rendus Hebdomadaires, (1928), 5 pp.
Gibble, et al., "Fibrin glue: the perfect operative sealant", Transfusion, 1990, vol. 30, No. 8., 741-747.
Huang, et al., "Tissue Engineering", vol. 8, No. 3, (2002), 469-481.
Hunziker, E.B., et al., "Quantitative structural organization of normal adult human articular cartilage", Osteoarthritis and Cartlilage 10, (2002), 564-572.
Kim, et al., "OsteoArthritis and Cartilage", vol. 11, (2003), 653-664.
Langer , F, et al., "Immunogenicity of Allograft Articular Cartiliage", JBJS, vol. 46-A, No. 2, (1974), 297-304.
Langer, F, et al., "The Immunogenicity of Fresh and Frozen Allogenic Bone", JBJS, vol. 57-A, No. 2, (1975), 216-220.

Lapchinsky, A G, et al., "Instrument for Shredding Cartilage in Plastic Surgeries", New Surgical Machines and Instruments and their usage, No. 4, Moscow, (1960), 209-213.

Mannheim, A, "Free Autoploastic Cartilage transplantation—Uber freie autoplastische Knorpeltransplantation", Arch. F klin Chir, (1926), 668-672.

Marvin, H M, "The Value of the Xanthine Diuretics in Congestive Heart Failure", The Journal of the American Medical Association, vol. 87, No. 25, Abstract only, (Dec. 18, 1926), 2131-2132.

Peer, Lyndon, "Diced Cartilage Grafts—New Method for Repair of Skull Defects, Mastoid Fistula and Other Deformities", Archives of Otolaryngology, vol. 38, No. 2, (1943), 156-165.

Polettini, Bruno, "Su neoformazioni carilaginee ed ossee determinate da innesti di frammenti di cartilaginee e d'osso fissati", (1922), 179-192.

Verwoerd, C.D.A., et al., "Wound Healing of Aurologous Implants in the Nasal Septal Cartilage", Department of Otorhinolaryngology and Pathology, ORL vol. 53, (1991), 310-314.

Wikipedia, "Alpha-2-Macroglobulin", 8 pp.

* cited by examiner

IMPLANTS AND METHODS FOR REPAIR, REPLACEMENT AND TREATMENT OF DISEASE

CROSS-REFERENCE TO RELATED APPLICATIONS

This application is a U.S. National of PCT/US2006/33687 filed Aug. 28, 2006 which claims priority from U.S. Provisional Application Ser. No. 60/712,004 filed on Aug. 26, 2005, which is incorporated herein by reference in its entirety.

BACKGROUND

Joint disease, defect, and injury are leading causes of pain and disability in the adult population. The morbidity associated with joint disease, defect, and injury and their spectrum of associated disorders are responsible for significant health care, economic and social costs. Current treatments for repairing or ameliorating a joint disease, defect, or injury, for example an osteochondral injury in which articular cartilage and underlying bone are damaged, can be expensive, inefficacious, painful, or lengthy. Alternative treatments are, therefore, needed.

SUMMARY

In view of these and related unmet needs, the present teachings disclose implants which can be used in the treatment, repair and/or partial or full replacement of a chondral or osteochondral defect, such as a chondral or osteochondral disease, defect, injury or lesion. The present teachings also provide methods of forming the implants, as well as methods of treating a chondral or osteochondral defect or injury in a patient in need of treatment, using implants as disclosed herein.

In various embodiments, an implant of the present teachings comprises cartilage and a subchondral base comprising trabecular metal, which can be a subchondral base comprising at least one trabecular metal component. In certain alternative embodiments, an implant comprises chondrocytes and a subchondral base comprising trabecular metal, which can be a subchondral base comprising at least one trabecular metal component. A trabecular metal used in an implant comprises at least one metal, which can be, in various aspects, tantalum, niobium, stainless steel, a chromium-cobalt alloy or titanium. In some aspects, a chromium-cobalt alloy can be a chromium-cobalt molybdenum alloy. Furthermore, a trabecular metal comprises a plurality of pores. A plurality of pores can have, in some aspects, a median diameter of from about 3 microns to about 800 microns. In addition, in certain aspects a subchondral base can further comprise at least one porous surface layer which comprises a plurality of pores of median diameter from about 3 microns to about 800 microns. In these aspects, the trabecular metal can have a "graded" porosity, i.e., the median diameter of the plurality of pores of a surface layer can be different from that of the plurality of pores comprising the core of the trabecular metal. Accordingly, in various configurations, a porous surface layer can comprise a plurality of pores of median pore diameter of from about 100 microns to about 800 microns, or, in alternative configurations, a porous surface layer can comprise a plurality of pores of median pore diameter of from about 3 microns to about 20 microns.

In some configurations of an implant, a subchondral base can comprises at least two surfaces. In these configurations, one surface can comprise trabecular metal having a plurality of pores, wherein the pores have a median pore diameter of from about 100 microns to about 800 microns, while a second surface can be a cartilage-adherent surface. In some aspects of these configurations, a cartilage-adherent surface (i.e., a surface adhesive to cartilage and/or chondrocytes) can comprise a plurality of pores having a median pore diameter of from about 3 microns to about 20 microns. Alternatively, a cartilage-adherent surface can comprise a cartilage adhesive, or a cartilage-adherent surface can comprise both a plurality of pores having a median pore diameter of from about 3 microns to about 20 microns as well as a cartilage adhesive. In various aspects of these configurations, a cartilage adhesive can comprise tissue trans-glutaminase, hyaluronic acid, collagen type I, collagen type II, a chemically cross-linked collagen, fibrin, albumin, gelatin, elastin, silk, demineralized bone matrix, polyethylene oxide, polyethylene glycol, polyvinyl alcohol, polypropylene fumarate or a combination thereof (Jurgensen et al., J. Bone and Joint Surg. 79A: 185-193, 1997; U.S. Pat. No. 6,893,466 to Trieu; U.S. Pat. No. 6,835,277 to Goldberg et al.) or a hydrogel. Furthermore, a cartilage adhesive can also be adhesive towards chondrocytes. In various aspects, a vertebrate-derived component of a cartilage adhesive, such as tissue trans-glutaminase, hyaluronic acid, collagen type I, collagen type II, fibrin, albumin, gelatin, or elastin, or demineralized bone matrix, can be autologous, allogeneic, or xenogeneic to a mammalian recipient of an implant, such as a human patient in need of treatment. Furthermore, a protein or polypeptide component of a cartilage adhesive such as tissue trans-glutaminase, hyaluronic acid, collagen type I, collagen type II, fibrin, albumin, gelatin, or elastin, can be obtained from a naturally-occurring source such as an animal or human donor, or can be produced using molecular biological methods well known to skilled artisans, such as expression of a gene or cDNA encoding the protein in transformed or transfected cells (see, e.g., Sambrook, J., et al., Molecular Cloning: A Laboratory Manual, 3rd ed. Cold Spring Harbor Laboratory Press, Cold Spring Harbor, N.Y., 2001).

In some configurations, a region of a subchondral base comprising pores having a median pore diameter of about 100 microns to about 800 microns can provide a surface which can promote bone attachment and ingrowth, while a region comprising a cartilage-adherent surface can provide a surface which can promote chondrocyte and/or cartilage attachment and growth. In various configurations, a cartilage-adherent surface can be a region of a subchondral base comprising a plurality of pores having a median pore diameter of about 3 microns to about 20 microns, a cartilage adhesive, or a combination of a plurality of pores and a cartilage adhesive, and can comprise trabecular metal or a different material, such as a polymer. In certain configurations, an implant can further comprise a non-trabecular metal material which provides a surface for chondrocyte or cartilage attachment, such as, in non-limiting example, a chondrocyte-adherent ceramic or plastic. In addition, in some configurations, a trabecular metal component of an implant can have a geometry that promotes retention of chondrocytes, such as barbs, ridges or hooks.

In various aspects, the trabecular metal of an implant can comprise metal having a sintered, porous texture such as sintered, porous titanium or porous tantalum. Furthermore, the trabecular metal can be sintered and/or cancellous-structured. In addition, in some configurations, a porous surface layer can include a biocompatible porous metal sheet, such as a porous titanium sheet. In addition, in some configurations, a porous surface layer can include an absorbable biocompatible material such as polylactic/polyglycolic acid (PLA/PGA).

In various configurations of the present teachings, cartilage comprised by an implant can be juvenile cartilage, a cartilage formed in vitro such as neocartilage described in Adkisson, H. D. et al., Clin. Orthop. 391S: S280-S294, 2001; and U.S. Pat. Nos. 6,235,316 and 6,645,316 to Adkisson, minced cartilage, minced juvenile cartilage and/or devitalized cartilage. In various aspects, the cartilage can comprise chondrocytes. Chondrocytes comprising an implant can be, in various aspects, chondrocytes grown either in contact with a trabecular metal, separately from the trabecular metal, or in a combination of growth apart from the trabecular metal then in contact with the trabecular metal. The contact between the chondrocytes and the at least one trabecular metal can be established either in vivo or in vitro, and subsequent growth can occur in vivo, in vitro, or in a combination thereof. Chondrocytes in contact with trabecular metal can be, in some configurations, chondrocytes adherent to the trabecular metal. Chondrocytes used in various configurations of the implants, including chondrocytes comprised by cartilage, can be chondrocytes allogeneic to, autologous to, and/or xenogeneic to a mammalian recipient such as a human patient. A donor of the chondrocytes can be, in various configurations, a cadaver no older than about fourteen years of age at time of death. Accordingly, as used herein, the terms "juvenile chondrocytes" refers to chondrocytes obtained from a human donor less than about fourteen years of age at time of donation. Similarly, the term "juvenile cartilage" as used herein refers to cartilage formed from such chondrocytes. In some embodiments, chondrocytes comprising an implant can be chondrocytes differentiated from chondrocyte precursor cells such as mesenchymal stem cells, for example as described in U.S. Pat. No. 5,811,094 to Caplan et al.

In various aspects of the present teachings, an implant can comprise cartilage affixed to a subchondral base comprising trabecular metal. A subchondral base of these aspects can comprise a biocompatible metal sheet. A biocompatible metal sheet can be a biocompatible porous metal sheet or a biocompatible non-porous metal sheet An attachment between cartilage and a subchondral base of an implant can include, in non-limiting example, one or more sutures, one or more biocompatible adhesives, one or more biocompatible absorbable fasteners, a chemical cross-link, a polymer formed from subunits polymerized at a cartilage/trabecular metal juncture, and/or one or more laser welds. In these aspects, a biocompatible adhesive can include at least one biocompatible macromolecular adhesive such as a fibrin-based adhesive, a collagen-based adhesive or a combination thereof, and a biocompatible absorbable fastener can be, without limitation, a staple, a dart, a pin or a tack, and can comprise a biocompatible material such as, without limitation, polylactic/polyglycolic acid (PLA/PGA).

In various configurations, an implant of the present teachings can be substantially cylindrical in shape, or can be substantially a pyramidal wedge or substantially a frustoconical "mushroom" in shape (see, e.g., U.S. Pat. No. 6,743,232 to Overaker et al.) Alternatively, an implant can have a shape more closely approximating an anatomical shape, such as that of a joint or a bone/joint combination, such as a shape of a human condyle, a human hemi-condyle, a human acetabular cup or a human femoral head.

Embodiments of the present teachings also include methods of forming an implant comprising cartilage and a subchondral base comprising trabecular metal. Various configurations of these methods comprise growing a population of chondrocytes in vitro, and contacting the population of chondrocytes with a subchondral base comprising trabecular metal. In these embodiments, contacting a population of chondrocytes with a trabecular metal can include coupling or attaching the chondrocytes to the trabecular metal. In some aspects, growing a population of chondrocytes in vitro can comprise growing the chondrocytes in a matrix. In these aspects, the matrix can later be attached to a subchondral base comprising trabecular metal. In various aspects, the chondrocytes can be juvenile chondrocytes, and the trabecular metal can comprise a porous surface as described herein for an implant. In some configurations, chondrocytes can be grown in a scaffold-free environment. The chondrocyte population can also be grown in contact with a subchondral base comprising trabecular metal. In these methods, contact between the chondrocytes and the subchondral base can be initiated prior to chondrocyte growth, during chondrocyte growth, or after chondrocyte growth. The chondrocyte growth can occur in vivo or in vitro. Accordingly, the contacting between a trabecular metal and the chondrocytes can occur subsequent to the growing, and/or simultaneously with the growing. As a result, the juvenile chondrocytes can grow in contact with the trabecular metal, or without contacting the trabecular metal.

In some configurations, methods of forming an implant can comprise growing chondrocytes in the presence of a trabecular metal component such that the chondrocytes adhere to a surface of the component. In some alternative configurations, methods of forming an implant can comprise coupling a cartilage tissue component to a surface of a trabecular metal component.

In certain configurations, methods of forming an implant include attaching cartilage to a subchondral base. The attaching can comprise applying one or more sutures, a biocompatible adhesive, and/or an absorbable fastener to the cartilage and/or the subchondral base. A biocompatible adhesive can be, in non-limiting example, a macromolecule such as a fibrin, a collagen, or a combination thereof. An absorbable fastener can be, in non-limiting example, a staple, a dart or a tack. The attaching can be accomplished by methods well known to skilled artisans.

In some configurations, a method of these embodiments can include applying a biocompatible adhesive, such as a fibrin, to a subchondral base comprising trabecular metal, prior to contacting the base with a population of chondrocytes such as juvenile chondrocytes. In some alternative configurations, a method of these embodiments can include applying a biocompatible adhesive, such as a fibrin glue, to a population of chondrocytes prior to contacting the subchondral base with the chondrocytes. In these configurations, the fibrin can be fibrin autologous to a mammalian recipient of the implant, fibrin allogeneic to a mammalian recipient of the implant, fibrin xenogeneic to a mammalian recipient of the implant, synthetic fibrin, or a combination of two or more of these types of fibrin. Furthermore, trabecular metal comprised by a subchondral base can comprise a porous surface as described for implants herein. In addition, in some aspects, a method of these embodiments can further comprise applying to a surface of a subchondral base a biocompatible absorbable polymer, such as polylactic/polyglycolic acid (PLA/PGA). The surface can be, in some aspects, a porous surface of the subchondral base.

Methods of forming an implant comprising cartilage and a subchondral base can include, in various configurations, growing a population of juvenile chondrocytes in vitro in a scaffold-free environment, and contacting the population of juvenile chondrocytes with a trabecular metal subsequent to the growing.

Some embodiments of the present teachings include methods of treating joint disease, defect or injury in a patient in need thereof. These methods can include introducing, into a patient in need, an implant of the present teachings. Introduction of an implant can comprise insertion or attachment of the implant into bone tissue of a recipient. Accordingly, in some configurations, a method can comprise introducing an implant comprising both cartilage and a subchondral base comprising trabecular metal as described herein into a patient at a site of joint disease, defect or injury. In some alternative configurations, a method can comprise introducing a subchondral base comprising trabecular metal into a patient, and attaching to base a component comprising cartilage or chondrocytes, including juvenile chondrocytes. In certain configurations, the subchondral base can be configured to receive chondrocytes such as juvenile chondrocytes comprised by neocartilage. In some aspects of these configurations, the former component can further comprise a surface which promotes chondrocyte attachment, such as a porous surface having a plurality of pores of median diameter of about 3 microns to about 20 microns, a biocompatible macromolecule, or a combination thereof. In some configurations, the present teachings disclose methods comprising introducing into a patient a subchondral base comprising trabecular metal. In these configurations, the subchondral base can be configured for receiving chondrocytes. These methods further comprise adding, adjacent to subchondral base, chondrocytes such as juvenile chondrocytes which have been grown in vitro, thereby forming an implant of the present teachings. The chondrocytes in certain aspects can comprise juvenile chondrocytes grown in vitro but not organized into cartilage tissue, or can be juvenile chondrocytes comprised by neocartilage, and the subchondral base which is configured for receiving chondrocytes can comprise a porous surface region having a plurality of pores of median diameter of about 3 microns to about 20 microns, a biocompatible macromolecule, or a combination thereof. The subchondral base can further comprise a region having a plurality of pores of median diameter of about 100 microns to about 800 microns.

In some configurations of these embodiments, a method can further include introducing a non-trabecular metal positioning structure to a recipient patient. Such a positioning structure can aid in the positioning or physical stability of an implant in the patient. In various configurations, a positioning structure can comprise a biocompatible metal or a biocompatible polymer. In configurations of these embodiments, a trabecular metal portion of an implant can be configured to attach to the positioning structure, and/or the positioning structure can be configured to attach to the subchondral base. In certain aspects, the positioning structure can be configured for engaging the bone, and can be, in non-limiting example, a screw, a cylinder, a plat, a rod, or a washer. In addition, in various aspects, a positioning structure can also comprise trabecular metal, and/or can comprise a material other than trabecular metal, such as, in non-limiting example, a biocompatible polymer, or a metal that is non-trabecular.

In some configurations, an implant described herein can be used in the manufacture of a medicament for treatment of joint disease, repair, or injury.

Embodiments of the present teachings also encompass a kit comprising components of a disclosed implant. In these embodiments, a kit can include at least chondrocytes or cartilage, and a trabecular metal component of an implant. In some aspects of a kit, the chondrocytes or cartilage and the trabecular metal component can be packaged in separate containers, while in other aspects, a kit can comprise an implant comprising both cartilage or chondrocytes and a trabecular metal component of an implant. In some aspects, additional kit components can include culture medium for growing or maintaining chondrocytes or cartilage in vitro. In some configurations, a kit can further include instructions and/or reagents which can be used to assemble an implant, and/or tools and equipment which can aid in the assembly of an implant and/or installation of an implant into a recipient, such as, in non-limiting example, fasteners such as suturing thread, a staple, a dart, or a tack, such as a surgical grade staple, dart or tack,

DETAILED DESCRIPTION

Figure 1A:
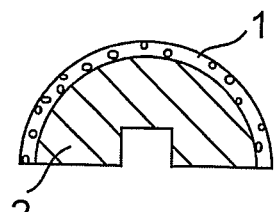
FIG. 1 illustrates replacement of a femoral head in a patient suffering from a femoral head fracture with an implant.

The present teachings disclose implants which can be used in the treatment of joint disease, defect or injury, including chondral or osteochondral disease, as well as methods of forming the implants. In some alternative embodiments, the present teachings disclose methods of treating a patient in need of treatment with the implants.

In various configurations, an implant of the present teachings comprises a combination of cartilage and a subchondral base comprising trabecular metal. "Cartilage," as used herein, encompasses articular cartilage, hyaline cartilage, neocartilage (Adkisson, H. D. et al., Clin. Orthop. 391S: S280-S294, 2001; and U.S. Pat. Nos. 6,235,316 and 6,645,316), devitalized cartilage, auricular cartilage, cartilage comprising genetically modified chondrocytes, cartilage from an autogenous source, cartilage from an allogenic source, cartilage from a xenogeneic source, juvenile cartilage, or a combination thereof. In some configurations, cartilage can also comprise chondrocytes differentiated from precursor cells such as mesenchymal stem cells. "Trabecular metal," as used herein, encompasses biocompatible, porous metal compositions, such as a porous tantalum biomaterial. Descriptions of trabecular metal, as well as various methods of making trabecular metal of various pore sizes and using trabecular metal in applications such as prosthetic devices are described in references such as Bobyn et al., J. Biomed. Mater. Res. 16: 571-581, 1982; Bobyn et al., J. Bone Joint Surg. Br. 81-B: 907-14, 1999; Bobyn et al., J. Arthroplasty 14: 347-354, 1999; Black, Clinical Materials 16: 167-173 (1994); Hacking et al., J. Biomed. Mater. Res. 52: 631-638, 2000; U.S. Pat. No. 4,863,475 to Andersen et al.; U.S. Pat. No. 4,479,271 to Bolesky et al.; U.S. Pat. No. 4,863,474 to Brown et al.; U.S. Pat. Nos. 5,535,810 and 6,544,472 to Compton et al.; U.S. Pat. No. 5,219,363 to Crowninshield et al.; U.S. Pat. Nos. 5,236,457, 5,387,243 and 5,571,187 to Devanathan; U.S. Pat.

Nos. 5,504,300, 5,672,284 and 5,723,011 to Devanathan et al.; U.S. Pat. No. 4,997,444 to Farling; U.S. Pat. No. 4,660,755 to Farling et al.; U.S. Pat. No. 6,740,186 to Hawkins et al.; U.S. Pat. Nos. 4,997,445 and 6,797,006 to Hodorek; U.S. Pat. No. 5,080,674 to Jacobs et al.; U.S. Pat. Nos. 5,734,959 and 5,926,685 to Krebs et al.; U.S. Pat. No. 4,566,138 to Lewis et al.; U.S. Pat. No. 6,417,320 to Otto et al.; U.S. Pat. No. 5,443,512 to Parr et al.; U.S. Pat. Nos. 6,685,987 and 6,395,327 to Shetty; U.S. Pat. Nos. 5,198,308, 5,323,954 and 5,443,510 to Shetty et al.; U.S. Pat. No. 5,496,375 to Sisk et al.; U.S. Pat. Nos. 6,336,930 and 6,447,514 to Stalcup et al.; U.S. Pat. No. 5,879,398 to Swarts et al.; U.S. Pat. No. 5,456,828 to Tersi et al.; U.S. Pat. No. 5,639,280 to Warner et al.; and U.S. Pat. Nos. 5,018,285 and 5,013,324 to Zolman et al.

In various configurations, an implant of the present teachings comprises a combination of chondrocytes and a subchondral base comprising trabecular metal. The chondrocytes can be, in some aspects, chondrocytes included in hyaline cartilage such as, without limitation, neocartilage. In other aspects, the chondrocytes can be chondrocytes with the potential to generate hyaline cartilage, but not organized into histologically recognizable cartilage. In some aspects of these configurations, a chondrocyte donor can be a cadaver. Hence, the chondrocytes can be cadaver chondrocytes. These chondrocytes can be grown in vitro using cell culture techniques known to skilled artisans, for example as described in U.S. patent application Ser. No. 10/956,971 of Milliman and Adkisson. As used herein, the term "cadaver chondrocytes" refers to viable chondrocytes originally comprised by a human cadaver, as well as clonal descendants of such chondrocytes, such as chondrocytes grown in vitro. Cadaver chondrocytes for use in the various aspects of the present teachings can be obtained from tissues comprising chondrocytes from a cadaver, such as cartilage tissue. Such tissues can be dissected from a cadaver using standard dissection methods well known to skilled artisans. The cartilage tissue utilized in the present teachings can comprise hyaline cartilage, or chondrocytes with the potential to generate hyaline cartilage, such as, for example, articular joint cartilage, tracheal cartilage, laryngeal cartilage, costal cartilage, epiphyseal plate cartilage, and combinations thereof. In various aspects, the cartilage tissue or chondrocytes can be knee joint cartilage or chondrocytes, hip joint cartilage or chondrocytes, or cartilage or chondrocytes from any other articular joint. Viable chondrocytes can be obtained from cartilaginous tissues in a donor cadaver any time after donor death of the donor, for example, for up to about two weeks after death of the donor. Accordingly, in some configurations, the time interval from the time of death of a donor (as determined, for example, by a physician or a coroner) to the time of dissection of cartilage tissue from the donor can be any time from immediately following a pronouncement of death, to about two weeks following death, such as, without limitation, about one hour, greater than 24 hours, about two days, about three days, about four days, about five days, about six days, about seven days, about eight days, about nine days, about ten days, about eleven days, about twelve days, about thirteen days, about fourteen days after death, or longer. In addition, a donor cadaver can be of any chronological age at time of death. For example, a donor cadaver can be, at time of death, about fourteen years old or younger. A donor cadaver need not be a familial member of a recipient, or be otherwise matched immunologically. Without being limited by theory, it is believed that chondrocytes are an "immunologically privileged" cell type, so that chondrocytes transplanted to an allogeneic recipient are not subject to rejection by the recipient's immune system.

In the present teachings, cartilage tissue can be removed from a cadaver using any surgical or dissecting techniques and tools known to skilled artisans. Following cartilage removal from a cadaver, the cartilage tissue can be minced, dissociated into single cells or small groups of cells, and/or placed into tissue or cell culture and expanded using standard techniques and apparatuses well known to skilled artisans. Such techniques and apparatuses are described in the references such as, for example, Feder, J. et al. in: Tissue Engineering in Musculoskeletal Clinical Practice. American Academy of Orthopaedic Surgeons, 2004; Adkisson, H. D. et al., Clin. Orthop. 391S:S280-S294, 2001; and U.S. Pat. Nos. 6,235,316 and 6,645,316 to Adkisson.

Cadaver chondrocytes used in the various embodiments of the present teachings are all cadaver chondrocytes which express type II collagen. In addition, in some aspects, cadaver chondrocytes can comprise chondrocytes expressing other molecular markers such as a high molecular weight sulfated proteoglycan, such as, for example, chondroitin sulfate (Kato, Y., and Gospodarowicz, D., J. Cell Biol. 100: 477-485. 1985). Presence of such markers can be determined using materials and methods well known to skilled artisans, such as, for example, antibody detection and histological staining.

In some configurations, cadaver cartilage tissue can be extracted from a cadaver. The cartilage tissue can then be dissociated into individual cells (or small clusters of cells), grown in vitro, and can then be combined with a subchondral base comprising trabecular metal, thereby forming an implant of the present teachings. Accordingly, in some aspects, the chondrocytes can be included in neocartilage. In vitro expansion of chondrocytes, and formation of neocartilage, can be accomplished using cell culture techniques and apparatuses well known to skilled artisans, such as culture methods for neocartilage described in U.S. Pat. Nos. 6,235,316 and 6,645,316 to Adkisson, and other general laboratory manuals on cell culture such as Sambrook, J. et al., Molecular Cloning: a Laboratory Manual (Third Edition), Cold Spring Harbor Laboratory Press, Cold Spring Harbor, N.Y., 2001; and Spector, D. L., et al., Culture and Biochemical Analysis of Cells, Cold Spring Harbor Laboratory Press, Cold Spring Harbor, N.Y. 1998.

In some configurations, a cell culture can include trabecular metal within a cell culture chamber. In these configurations, chondrocytes can grow in direct contact with a subchondral base of the present teachings, such as a subchondral base comprising trabecular metal as presented herein. Furthermore, the subchondral base can further comprise a cartilage-adherent surface. In various configurations, chondrocytes and/or cartilage can adhere to such a surface. In various aspects, chondrocytes adhered to such surfaces can proliferate and/or form cartilage such as neocartilage. Accordingly, as used herein, a "cartilage-adherent surface" is a surface of a biocompatible material to which cartilage can adhere. Similarly, as used herein, a "chondrocyte-adherent surface" is a surface of a biocompatible material to which chondrocytes can adhere. Non-limiting examples of cartilage- and chondrocyte adherent surfaces include a porous surface such as a trabecular metal surface comprising pores of median diameter from about 3 microns to about 20 microns, a plastic or ceramic surface comprising a cartilage adhesive or a chondrocyte adhesive, or a porous surface comprising pores of median diameter from about 3 microns to about 20 microns and a cartilage adhesive or chondrocyte adhesive. As used herein, the terms "cartilage adhesive" and "chondrocyte adhesive" refer to molecular species or mixtures of species which promote adhesion of cartilage or chondrocytes to a surface, by acting as a glue and/or by promoting adhesion-forming activity of cells. In various embodiments, a cartilage or chondrocyte adhesive can be used as a glue at the interface between cartilage or chondrocytes and a cartilage- or chondrocyte-adherent surface.

In certain configurations, cartilage tissue can be harvested from a donor such as a cadaver and placed as explants in a cell culture chamber including a growth medium as disclosed in the above-cited references. In some aspects, a cell culture chamber can further include a subchondral base (which can comprise trabecular metal) and a chondrocyte-adherent surface. In these aspects, chondrocytes can migrate out from the explant and populate the chondrocyte-adherent surface. A subchondral base populated with chondrocytes can be used directly as an implant in a recipient, or can be cultured under conditions which promote chondrocyte or cartilage maintenance or growth, or neocartilage formation as disclosed, for example, in U.S. Pat. Nos. 6,235,316 and 6,645,316 to Adkisson or U.S. Pat. No. 5,041,138 to Vacanti et al.

In certain alternative configurations, a cartilage explant can be affixed directly to a subchondral base and a cartilage-adhesive surface to form an implant, using methods and materials disclosed herein, such as, for example, sutures, adhesives, and fasteners.

In various aspects, chondrocytes adhered to a cartilage-adherent surface can grow and/or form cartilage tissue such as neocartilage. In certain alternative aspects, a surface can comprise a cartilage adhesive such as a fibrin adhesive as described herein. In yet other aspects, a surface can comprise a both a plurality of pores having a median diameter of about 3 microns to about 20 microns and a cartilage adhesive. The surface can comprise, in non-limiting example, trabecular metal, plastic such as cell culture plastic or an absorbable biocompatible material such as polylactic/polyglycolic acid (PLA/PGA). In addition, in various aspects, chondrocytes such as juvenile chondrocytes can be grown separately from a subchondral base.

In some embodiments of the present teachings, a method of treating a patient can comprise transferring an implant into a recipient patient. In other embodiments, a subchondral base component of an implant can be implanted into a recipient patient, for example by surgically attaching the subchondral base to a bone, followed by addition of chondrocytes and/or cartilage adjacent to the subchondral base. In some configurations, a method can further comprise attaching a positioning structure to a patient, then attaching an implant to the positioning structure. As used herein, the term "positioning structure" refers to a structure configured for supporting, positioning and/or maintaining the position of an implant of the present teachings or a portion thereof in a recipient such as a human patient. In non-limiting example, a positioning structure can be a screw or a cylinder which attaches to an aperture introduced into a patient's bone. A positioning structure of these configurations can comprise a biocompatible material such as, for example, a biocompatible polymer or a biocompatible metal.

In certain configurations, a positioning structure can be configured for engaging the bone. In these configurations, a positioning structure can be introduced to a bone of a subject. A subchondral base can then be attached to the positioning structure. Chondrocytes or cartilage, such as, in non-limiting example, devitalized cartilage or neocartilage, can then be attached to the subchondral base. Alternatively, in some configurations, a positioning structure can be introduced into a patient, for example by attaching to a bone an implant comprising both chondrocytes and/or cartilage and a subchondral base comprising trabecular metal can then be attached to the positioning structure.

Trabecular metal comprised by the implants of the present teaching can comprise any form of trabecular metal that is compatible with viable cells or tissues. In various aspects, trabecular metal used in an implant can be trabecular metal described in publications such as U.S. Pat. No. 5,282,861 to Kaplan, U.S. Pat. No. 5,456,723 to Steinemann et al., U.S. Pat. No. 6,087,553 to Cohen, or U.S. Pat. No. 6,840,960 to Bubb. In non-limiting examples, the trabecular metal can comprise tantalum, which can be substantially pure tantalum, niobium, titanium, which can be substantially pure titanium, stainless steel, a chromium-cobalt alloy, or a combination thereof. In some aspects, a chromium-cobalt alloy can be a chromium-cobalt-molybdenum alloy. In certain configurations, the trabecular metal can be porous throughout its structure, or substantially porous near the surface, and can comprise, in non-limiting example, a porous surface layer and a core, which can be porous or non-porous. Accordingly, in some configurations, a trabecular metal can include a core comprising a biocompatible material, such as, in non-limiting example, tantalum, niobium, titanium, a chrome-cobalt alloy or a ceramic, and a porous surface which can be, in non-limiting example, a porous titanium sheet or a cancellous-structured titanium layer.

In some configurations, an implant comprising a subchondral base comprising trabecular metal of the present teachings can further comprise one or more bioactive molecules, such as, in non-limiting example, a transforming growth factor-β family member protein such as a bone morphogenetic protein (BMP), basic fibroblast growth factor (bFGF), or other chondroinductive or osteoinductive molecules. Accordingly, in some aspects, a chondral-adhesive portion of an implant can comprise one or more chondroinductive molecules, while a subchondral base can comprise one or more osteoinductive molecules.

In some aspects of the present teachings, a surface for attachment of chondrocytes can comprise a plurality of pores. The pores can have a median pore diameter from about 3 microns to about 20 microns. The pores can be substantially homogeneous in diameter, or can be substantially heterogeneous in diameter. In some alternative aspects, the surface can comprise at least one biological macromolecule. A biological macromolecule can be, in some configurations, a macromolecule such as hyaluronic acid, collagen type I, collagen type II or fibrin. In various aspects, fibrin comprised by a surface layer can include fibrin that is autologous to a mammalian recipient of the juvenile chondrocytes, fibrin allogeneic to a mammalian recipient of the juvenile chondrocytes, fibrin xenogeneic to a mammalian recipient of the juvenile chondrocytes, synthetic fibrin, or a combination of two or more of these types of fibrin. In yet other aspects, a surface for attachment of chondrocytes can comprise both a plurality of pores and at least one biological macromolecule or biocompatible polymer. Such surfaces can be prepared using techniques known to skilled artisans, such as, for example, techniques disclosed in U.S. Pat. No. 6,740,186 to Hawkins. In some aspects, trabecular metal can be coated with or coupled to a biocompatible porous absorbable polymer, such as, for example, PLA/PGA to form a biocompatible surface layer to which chondrocytes can attach. Such a surface layer can promote juvenile chondrocyte growth in vivo or in vitro. In other aspects, trabecular metal can be coated with an osteoconductive or chondroconductive material such as, in non-limiting example, hydroxyapatite or hydroxyapatite-tricalcium phosphate.

In certain configurations, trabecular metal can be attached to biocompatible porous absorbable polymer such as PLA/PGA to form a reservoir or "cup" into which chondrocytes, cartilage and/or a biocompatible adhesive can be placed. In this connection, U.S. Pat. No. 4,997,445 to Hodorek discloses examples of methods for attaching a polyethylene polymer to a metal base which can be adapted to form the base of an implant of the present teachings.

In various aspects of the present teachings, trabecular metal comprising a porous surface can be made by any process known to skilled artisans, such as, in non-limiting example, etching methods or sputtering methods. In various aspects of the present teachings, a porous surface layer of a subchondral base used in an implant can comprise metal having a sintered, porous texture such as, for example, sintered, porous, cancellous-structured titanium. In addition, in some configurations, a porous surface layer can include a biocompatible porous metal sheet, such as a porous titanium sheet or a stainless steel sheet. Accordingly, in some configurations, an implant can comprise a trabecular metal which comprises a core material, which may or may not be porous, and a porous covering or sheet. In non-limiting example, the core material can be a chrome-cobalt alloy, such as, without limitation, a chrome-cobalt-molybdenum alloy, tantalum, niobium or titanium.

In various aspects, a subchondral base comprising trabecular metal can further comprise at least one biological macromolecule, a biocompatible polymer, a biocompatible ceramic, and/or an osteoconductive or chondroconductive material such as hydroxyapatite or hydroxyapatite-tricalcium phosphate. A biological macromolecule of these aspects can be, without limitation, hyaluronic acid, a transforming growth factor-β family member protein such as a bone morphogenetic protein (BMP), basic fibroblast growth factor (bFGF), or other chondroinductive or osteoinductive molecule. Without being limited by theory, it is believed that a biological macromolecule or biocompatible polymer can promote attachment of chondrocytes or cartilage to a trabecular metal surface by acting as a carrier and/or an adhesive. It is further believed that a biological macromolecule or biocompatible polymer, such as bioabsorbable polymer such as PLA/PGA can promote chondrocyte expansion when used as a coating of a surface such as a trabecular metal surface.

In various configurations of the present teachings, juvenile cartilage comprised by an implant can comprise cartilage formed in vitro, such as neocartilage described in Adkisson, H. D. et al., Clin. Orthop. 391S: S280-S294, 2001; and U.S. Pat. Nos. 6,235,316 and 6,645,316 to Adkisson. Chondrocytes comprising the cartilage can be grown either in contact with a subchondral base, separately from the subchondral base, or in a combination of growth apart from the base then in contact with the base. The contact between the chondrocytes and the subchondral base can be established either in vivo or in vitro, and subsequent growth can occur in vivo, in vitro, or a combination thereof. In non-limiting example, a culture chamber can be established comprising both chondrocytes and trabecular metal, under culture conditions that support formation of neocartilage. The neocartilage can then form directly on the surface of the at least one trabecular metal. The chondrocytes comprising the juvenile cartilage can be chondrocytes allogeneic to a mammalian recipient such as a human patient, or autologous to a recipient.

In certain aspects of the present teachings, an implant can include cartilage such as neocartilage comprising juvenile chondrocytes grown in contact with a subchondral base, either in vitro or in vivo, and can furthermore include neocartilage from juvenile cartilage attached to the subchondral base. As used herein, "chondrocyte growth" includes expansion of a population of chondrocytes or chondrocyte precursor cells such as mesenchymal stem cells, differentiation of chondrocyte precursor cells into chondrocytes, and/or accumulation and buildup of cartilaginous extracellular matrix during cartilage tissue formation. The attachment can include an attachment between the neocartilage and the base, and can aid in the establishment and/or retention of the shape of an implant. Accordingly, in some aspects, an implant can include at least one suture, which can attach the juvenile cartilage to the base. In non-limiting example, a series of sutures can be used to hold neocartilage to trabecular metal comprised by a subchondral base. Standard suturing instrumentation and techniques well-known to skilled artisans can be used to attach the neocartilage to the at least one trabecular metal. The sutures can be made of any known suture material, such as, for example, an absorbable material such as PLA/PGA. In alternative aspects, cartilage can be attached to a subchondral base using at least one biocompatible adhesive, such as, in non-limiting example, a fibrin-based adhesive, a collagen-based adhesive or a combination thereof. In yet other aspects, attachment of cartilage to a subchondral base can be effected using at least one absorbable fastener. In these aspects, an absorbable fastener can comprise a biocompatible material such as PLA/PGA, and can be, without limitation, a staple, a dart, or a tack, such as a surgical grade staple, dart or tack. A fastener can be applied to cartilage and a subchondral base using any technique known to skilled artisans. In some configurations, cartilage can be attached to a subchondral base by applying a chemical cross-linker such as, in non-limiting example, an aldehyde cross-linker such as formaldehyde or glutaraldehyde, or a homobifunctional or heterobifunctional cross-linker such as a cross-linker having amine-reactive and thiol reactive moieties, for example sulfosuccinimidyl 4-[N-maleimidomethyl]cyclohexane-1-carboxylate, supplied by Pierce Chemical, Rockford Ill.

In various configurations, an implant of the present teachings can be substantially cylindrical in shape. Cylindrically shaped implants comprising non-autologous chondrocytes can be used, for example, in mosaicplasty-type joint repairs (see, e.g., Minas, T. et al., Orthopedics 20: 525-538, 1997; Marcacci, M., et al., Arthroscopy 21: 462-470, 2005; Christel, P., et al., http://www.maitrise-orthop.com/corpusmaitri/orthopaedic/mo76_mosaicplasty/index.shtml). Alternatively, one or more features of an implant can have a shape more closely approximating an anatomical shape, such as, for example, a feature of a joint. Without limitation, an implant of the present teachings can have, in some aspects, a substantially anatomical shape such as a shape of a human condyle, a hemi-condyle, an acetabular cup or a femoral head.

The present disclosure also includes methods of forming an implant of the present teachings. These methods comprise growing a population of chondrocytes in vitro, and contacting the population with a trabecular metal comprising a porous surface. In some configurations, the chondrocyte population can be grown in a scaffold-free environment. As used herein, the term "scaffold" refers to a support for chondrocytes or cartilage tissue onto which cells can attach, proliferate, and/or synthesize new tissue, other than a cell culture apparatus such as a plastic cell culture chamber. For example, chondrocytes obtained from a cadaver can be grown to increase cell numbers by about 1000 fold without any trabecular metal in a cell growth apparatus comprising the chondrocytes (e.g., a cell culture flask). The cells, which can be included within neocartilage, can then be attached to a piece of trabecular metal which can be of a shape appropriate for an osteochondral repair in a patient, and thereby form an implant which can be transplanted to the patient at a site of joint injury, defect or disease.

In some aspects, a chondrocyte population can be grown in contact with a subchondral base comprising trabecular metal. In these configurations, chondrocytes can be grown in an apparatus comprising the subchondral base. In various aspects of these configurations, the chondrocytes can attach and grow directly on the trabecular metal surface in vitro, and thereby form neocartilage directly on the trabecular metal. A resulting implant can then can then be transplanted to a recipient patient. Furthermore, in these configurations, chondrocytes can form neocartilage on the trabecular metal, and thereby form a layered structure comprising a layer of metal covered by a layer of neocartilage. Accordingly, implants can be formed of various shapes for transplantation into a patient. For example, an implant comprising trabecular metal shaped as an acetabular cup for a hip replacement can be covered on its rounded surface with cartilage by growing juvenile chondrocytes in the presence of the trabecular metal.

Accordingly, the present disclosure provides methods of treating joint disease, defect, or injury in a patient in need thereof. As used herein, "joint disease, defect or injury" includes physical conditions or diseases which can benefit from cartilage or osteochondral repair, replacement, or augmentation, such as, in non-limiting example, athletic injury, traumatic injury, congenital disorders, osteoarthritis and joint degeneration from aging. These methods include introduction of an implant of the present teachings into a recipient patient in need of treatment. In some embodiments, the methods comprise transplanting an implant comprising cartilage and/or chondrocytes and a subchondral base as described herein into the patient at a site of joint disease, defect or injury. In other embodiments, some methods comprise implanting into a patient an subchondral base comprising trabecular metal, and applying juvenile chondrocytes to the subchondral base subsequent to the implantation. In some configurations, a subchondral base can further comprise a chondrocyte attachment portion as described above. By temporally separating the attachment of the subchondral base to the bone and the attachment of the chondrocytes to the subchondral base, methods of these embodiments can reduce or eliminate trauma to the cells that can be associated with attaching a hard object to a bone of a patient. In additional embodiments, a positioning device can also be introduced into a patient. The positioning device can be attached to an appropriate site in a patient by a health professional such as a surgeon. In non-limiting example, a positioning device can be attached to a bone or introduced into an aperture in the bone. The positioning device can be configured for the attachment of the at least one trabecular metal base portion. The positioning device can be, in non-limiting example, a screw or a cylinder. A positioning device can comprise any material compatible with a patient's physiology, such as, for example, metal including non-trabecular metal, an absorbable polymer such as polylactic/polyglycolic acid (PLA/PGA) or a non-absorbable polymer. In certain configurations, the subchondral base can be configured to engage the positioning device, for example by comprising an internal screw thread which mates with the screw of the positioning device. Chondrocytes, which can be in the form of neocartilage, can then be applied to the prosthetic device. Alternatively, cartilage and/or chondrocytes can be applied to subchondral base before attaching the latter to the positioning device. In yet other configurations, a positioning device can comprise a surface for attaching chondrocytes and/or cartilage. In these configurations, chondrocytes or cartilage can be attached to the surface; a subchondral base comprising trabecular metal can be inserted into a patient (for example, by insertion of the base into an aperture introduced by a surgeon into a bone of the patient) and the positioning device, including the chondrocytes or cartilage, can then be attached to the subchondral base, thereby forming an implant comprising a subchondral base and chondrocytes and/or cartilage Accordingly, a wide variety of possible combinations comprising a subchondral base, chondrocytes and/or cartilage, and a positioning device are contemplated as within the scope of the present teachings.

EXAMPLES

Various embodiments of the present teachings can be illustrated by the following non-limiting examples. The following examples are illustrative, and are not intended to limit the scope of the claims. The description of a composition or a method in an example does not imply that a described article or composition has, or has not, been produced, or that a described method has, or has not, been performed, irrespective of verb tense.

Example 1

This example illustrates replacement of a femoral head in a patient suffering from a femoral head fracture with an implant.

Figure 1B:
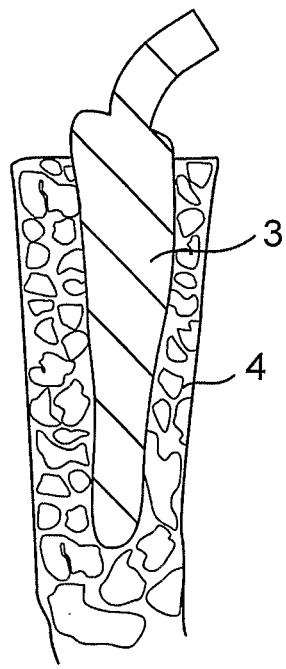
Figure 1C:
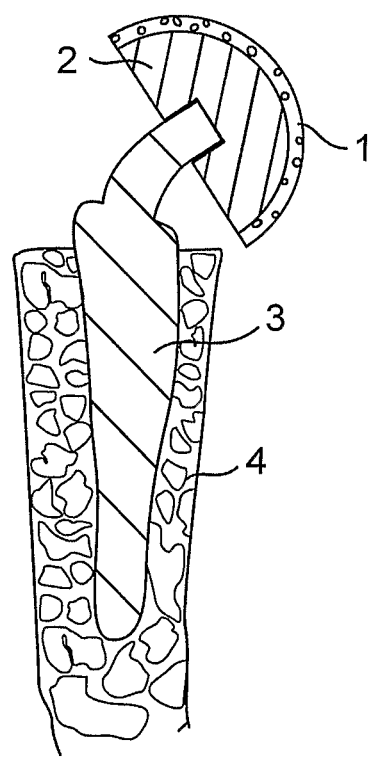

In this example, as shown in FIG. 1, a porous femoral head prosthesis (2) comprising a rounded surface comprising pores of median diameter of about 10 microns, is placed in an in vitro cell growth chamber. Juvenile chondrocytes are seeded onto the rounded surface, and cultured as described in Adkisson, H. D. et al., Clin. Orthop. 391S: S280-S294, 2001; and U.S. Pat. Nos. 6,235,316 and 6,645,316). The chondrocytes are permitted to grow until a layer of neocartilage (1) forms on the surface of the prosthesis (FIG. 1a). A surgeon then drives a spike-shaped subchondral base (3) comprising trabecular metal into the proximal femur (4) of the patient (FIG. 1b). The surgeon then attaches the femoral head prosthesis comprising neocartilage (1) and trabecular metal (2) to the subchondral base (3), thereby forming an implant comprising cartilage and a subchondral base which replaces the patient's fractured femur head (FIG. 1c).

Example 2

This example illustrates attachment of neocartilage to a subchondral base in vitro.

Figure 2A:
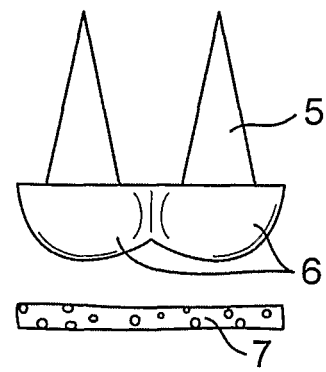
FIG. 2 illustrates attachment of neocartilage to a subchondral base in vitro.
Figure 2B:
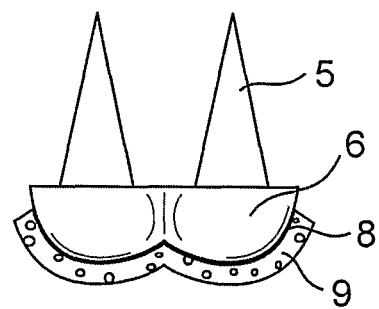

In this example, as shown in FIG. 2, a subchondral base (5) comprising trabecular metal and shaped to replace a condyle (6) is rendered adherent for cartilage by application of a fibrin adhesive to the rounded surfaces of the trabecular metal. The rounded surfaces of the base is then contacted with neocartilage grown in vitro (7) (FIG. 2a). The neocartilage (9) adheres to the adhesive layer (8), providing a layer of neocartilage following the contours of the surface of the base (9), thereby forming an implant which can replace a diseased or injured condyle of a patient (FIG. 2b).

Example 3

This example illustrates use of a positioning structure to introduce an implant into a patient.

Figure 3A:
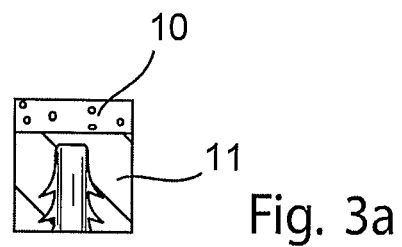
FIG. 3 illustrates a screw-shaped positioning structure inserted into bone, and attachment of an implant to the structure.
Figure 3B:
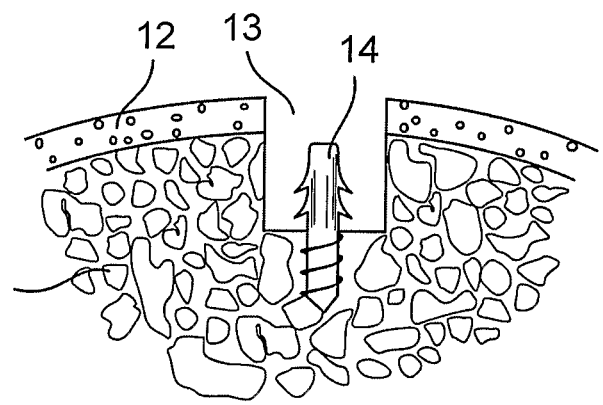
Figure 3C:
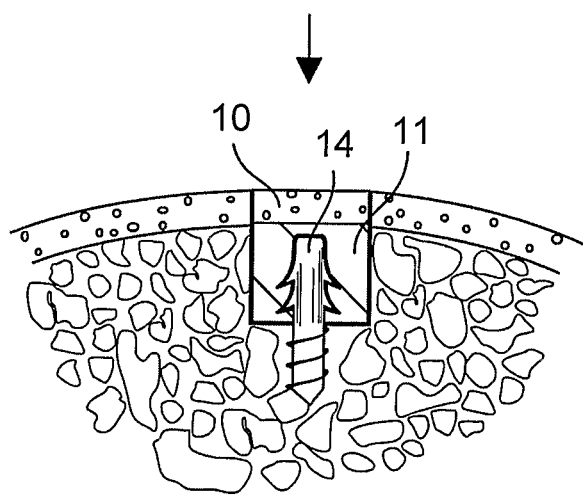

In this example, as shown in FIG. 3, a subchondral base (11) comprising trabecular metal and having an internal screw thread is seeded with chondrocytes which are cultured to form neocartilage (10), thereby providing an implant (FIG. 3a). A surgeon prepares a cylindrical-shape implant site which traverses the patient's cartilage and invades the bone in a condyle of the patient (13). The implant site has a depth and diameter corresponding to the implant. The surgeon then inserts a non-trabecular metal screw (14) into the site, leaving the screw partially exposed (FIG. 3b). The surgeon then lightly presses the implant into the site, thereby engaging the exposed screw (14) with the internal screw thread of the implant. The surgeon presses on the implant until the neocartilage (1) is flush with the patient's cartilage (FIG. 3c). The neocartilage can then heal smoothly with the patient's own condyle cartilage (12), and the trabecular metal can attach to the bone.

Example 4

This example illustrates another configuration that uses a positioning structure to introduce an implant into a patient.

Figure 4A:
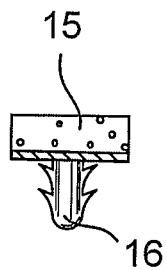
FIG. 4 illustrates a trabecular metal base having receiving screw threads, a positioning structure comprising a screw and a "platform" to which neocartilage is attached, and formation of an implant comprising the trabecular metal and the positioning structure.
Figure 4B:
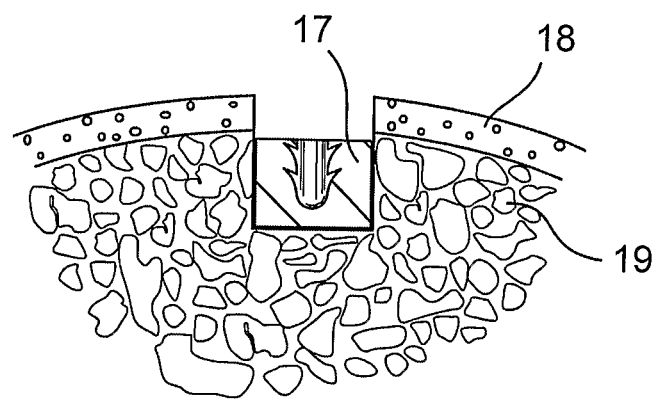
Figure 4C:
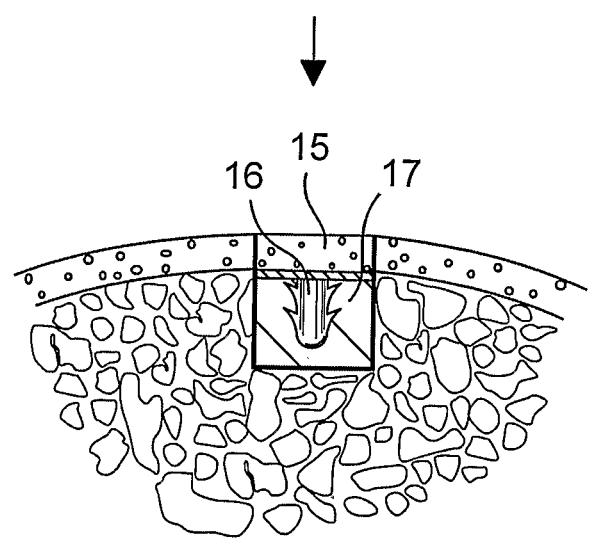

In this example, as shown in FIG. 4, an intermediate positioning structure (16), which does not comprise trabecular metal, comprises a screw thread and a flat surface "platform" to which a fibrin adhesive is applied. Neocartilage (15) is applied to the platform, and cultured until it adheres (FIG. 4a). A surgeon then prepares a cylindrical-shape implant site which traverses the cartilage and invades the bone (19) in a patient, and inserts a cylindrical-shape subchondral base comprising trabecular metal and an internal screw thread (17), as in Example 3 (FIG. 4b). The surgeon then presses the intermediate positioning structure (16) into the subchondral base (17), until the neocartilage (15) is flush with the patient's cartilage (18). The neocartilage can then heal smoothly with the patient's own cartilage, and the trabecular metal can attach to the bone (FIG. 4c).

Example 5

This example, as shown in FIG. 5, illustrates attachment of cartilage to a subchondral base comprising trabecular metal.

Figure 5A:
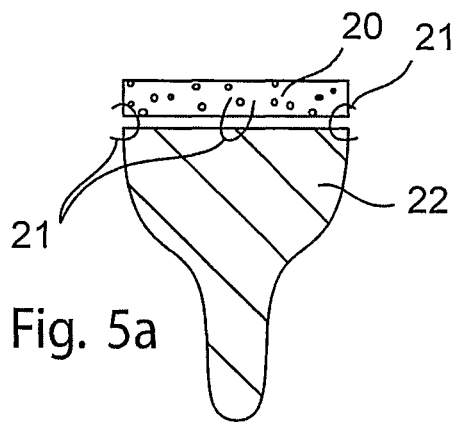
FIG. 5 illustrates attachment of cartilage to a subchondral base comprising trabecular metal.
Figure 5B:
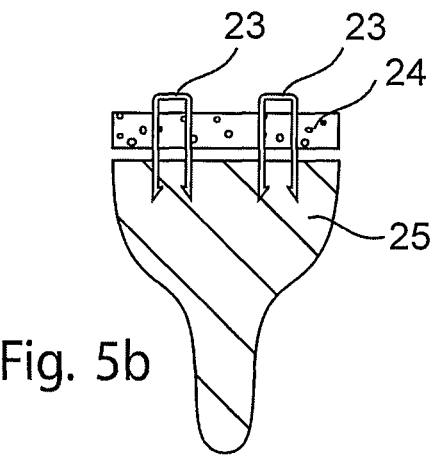
Figure 5C:
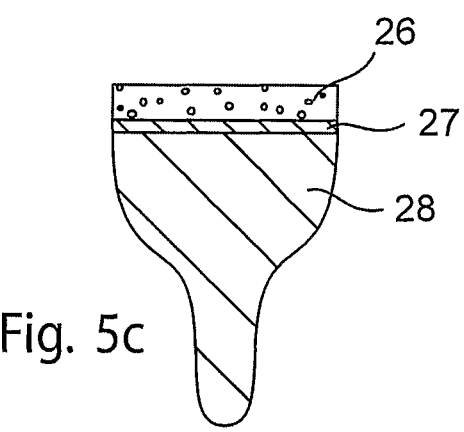

In this example, FIG. 5a shows attachment of cartilage (20) to trabecular metal (22) using sutures (21). FIG. 5b shows attachment of cartilage (24) to trabecular metal (25) using staples, tacks or darts (23). FIG. 5c shows attachment of cartilage (26) to trabecular metal (28) using an adhesive such as fibrin, collagen, or hydrogel (27). These configurations can be transplanted to a patient without in vitro culture, and are particularly useful for forming an implant either in vivo or in the operating room.

Example 6

This example illustrates seeding of chondrocytes onto trabecular metal of a subchondral base.

Figure 6:
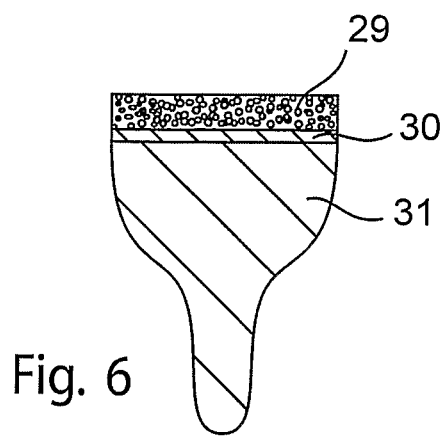
FIG. 6 illustrates seeding of cells onto a trabecular metal component of a subchondral base.

In this example, as shown in FIG. 6, an implant is shown in which juvenile chondrocytes (29) allogeneic to a patient are seeded onto a surface of a subchondral base comprising trabecular metal (31). The surface for cell attachment comprises trabecular metal having a median pore diameter of from about 3 microns to about 20 microns. The surface for cell attachment is treated with sintered porous structured titanium to form a surface layer (30) prior to the seeding of cells.

In related configurations, the surface layer can also be formed with one or more of the following: a) trabecular metal fine pore phase; b) hyaluronic acid; c) collagen I; d) collagen II, e) fibrin (including autologous, allogeneic, xenogeneic, or synthetic); f) absorbable synthetic polymer such as PLA/PLG); synthetic or natural hydrogel; g) titanium screen or porous sheet. The configurations of this example, like those of Example 5, are also useful for forming an implant either in vivo or in the operating room.

Example 7

This example illustrates seeding of cells onto trabecular metal.

In this example, an implant as illustrated in FIG. 6 is prepared as described in Example 6, except that seeding and culturing of cells is performed in vitro such that tissue grows and cells attach to pores of the trabecular metal or surface layer. This example illustrates seeding of cells onto trabecular metal for formation of cartilage in vitro.

Example 8

This example, as shown in FIG. 7, illustrates a variety of useful implant shapes.

Figure 7A:
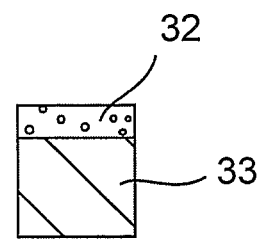
FIG. 7 illustrates a variety of implant shapes useful for chondral or osteochondral repair.

FIG. 7a presents a cylindrical shape comprising a subchondral base comprising trabecular metal (33), and cartilage adherent on one surface (32).

Figure 7B:
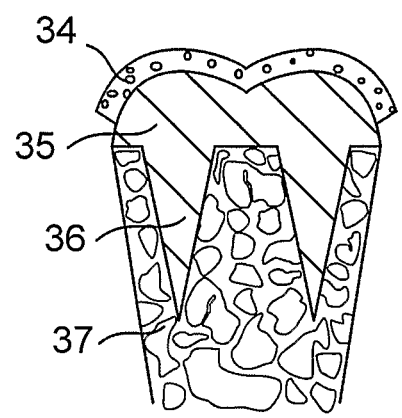

FIG. 7b presents an anatomical shape: the subchondral base comprising trabecular metal (35) comprises a contoured dual-hemispherical surface for cell attachment and two spikes (36) for insertion into bone (37), while the cartilage (34), which adopts the shape of the contoured surface, can replace the condyle of a distal femur.

Figure 7C:
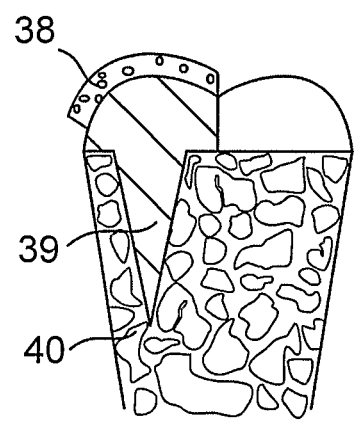

FIG. 7c presents a second anatomical shape: the subchondral base comprising trabecular metal comprises a contoured-hemispherical surface for cell attachment and a spike (39) for insertion into bone (40), while the cartilage (38), which adopts the shape of the contoured surface, can replace a hemi-condyle.

Example 9

This example, as shown in FIG. 8, shows additional anatomical shapes.

Figure 8A:
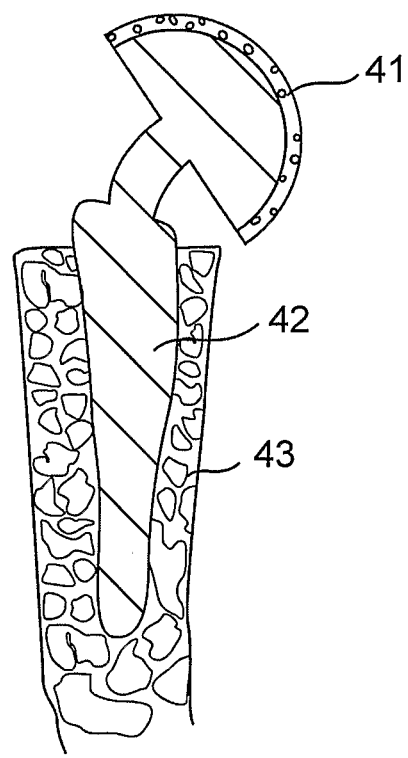
FIG. 8 illustrates an anatomically-shaped implant as inserted into bone.

FIG. 8a presents cartilage (41) attached to an anatomically shaped femoral head prosthesis, as presented in Example 1. The femoral head prosthesis attaches to a spike-shaped trabecular metal component (42) which, in turn, inserts into native bone (43). This shape can be used to repair a proximal femur.

Figure 8B:
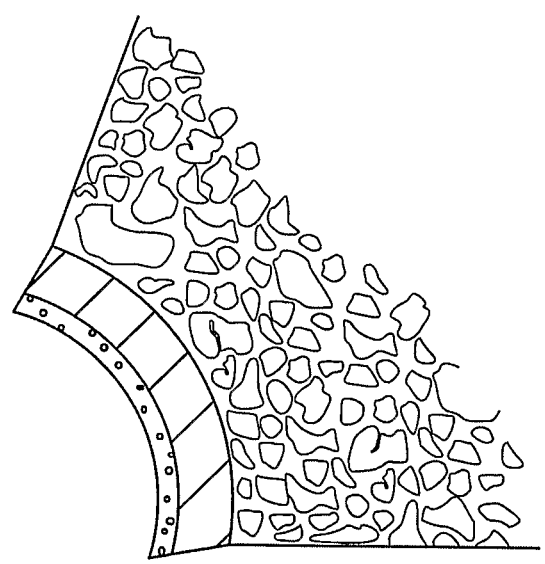

FIG. 8b presents an acetabular cup, which includes a cartilage component attached to a trabecular metal component, attached to native bone.

It is to be understood that particular formulations and processes of the present teachings are not limited to the descriptions of the specific embodiments presented, but rather the descriptions and examples should be viewed in terms of the claims that follow and their equivalents. While some of the examples and descriptions above may include some conclusions about the way the certain embodiments function, the inventors do not intend to be bound by those conclusions and functions, but put them forth only as possible explanations.

It is to be further understood that the specific embodiments of the present teachings as set forth are not intended as being exhaustive or limiting of the invention, and that many alternatives, modifications, and variations will be apparent to those of ordinary skill in the art in light of the foregoing examples and detailed description. Accordingly, the disclosed embodiments are intended to embrace all such alternatives, modifications, and variations that fall within the spirit and scope of the following claims.

All publications, patents, patent applications and other references cited in this application are herein incorporated by reference in their entirety as if each individual publication, patent, patent application or other reference were specifically and individually indicated to be incorporated by reference.

What is claimed is:

1. An implant for administering to a patient in need of treatment for joint disease, defect or injury, the implant comprising:
    minced juvenile cartilage tissue from a human cadaveric donor; and
    a subchondral base comprising at least one trabecular metal.

2. The implant of claim 1 wherein the cartilage tissue comprises articular cartilage.

3. The implant of claim 2 wherein the cartilage tissue and the subchondral base are attached.

4. The implant of claim 1, wherein the subchondral base further comprises at least one porous surface layer and a porous core, the at least one porous surface layer comprising a plurality of pores of median diameter from about 3 microns to about 800 microns wherein the median diameter of the plurality of pores of the at least one porous surface layer is different from that of the plurality of pores of the core of the subchondral base.

5. The implant of claim 1, wherein the subchondral base comprises at least two surfaces, wherein a first surface comprises trabecular metal comprising a plurality of pores having a median pore diameter of from about 100 microns to about 800 microns, and a second surface which is a cartilage-adherent surface.

6. The implant of claim 5, wherein the cartilage-adherent surface comprises a plurality of pores of median diameter from about 3 microns to about 800 microns.

7. The implant of claim 5, wherein the cartilage-adherent surface comprises a cartilage adhesive.

8. The implant of claim 7, wherein the cartilage adhesive comprises a hydrogel.

9. The implant of claim 7, wherein the cartilage-adhesive comprises trans-glutaminase, hyaluronic acid, collagen, fibrin, albumin, elastin or silk.

10. The implant of claim 9, wherein the cartilage adhesive comprises fibrin.

11. The implant of claim 1 wherein the trabecular metal comprises tantalum, niobium, stainless steel, chromium-cobalt alloy or titanium.

12. The implant of claim 11 wherein the trabecular metal comprises tantalum.

13. The implant of claim 1 wherein the subchondral base is cylindrical.

14. The implant of claim 1 wherein the subchondral base approximates the anatomical shape of a human condyle, hemi-condyle, acetabulum or femoral head.

15. A kit for forming the implant of claim 1, the kit comprising:
    an amount of the cartilage tissue;
    the subchondral base comprising at least one trabecular metal; and
    packaging for the cartilage tissue and the subchondral bone.

16. The kit of claim 15 further comprising a cartilage adhesive.

17. The kit of claim 15 wherein the subchondral base is packaged separately from the cartilage tissue and cartilage adhesive.

18. A method of treating joint disease, defect or injury in a patient in need thereof comprising:
    introducing into the patient a subchondral base comprising at least one trabecular metal, wherein the subchondral base is configured to receive cartilage tissue; and
    applying minced juvenile cartilage tissue from a human cadaveric donor to the subchondral base.

19. The method of claim 18 wherein the cartilage tissue is applied to the subchondral base after introducing the subchondral base into the patient.

20. The method of claim 19, wherein applying comprises attaching the cartilage tissue to a surface of the subchondral base.

21. The method of claim 20, wherein attaching comprises applying a cartilage adhesive to an interface between a surface of the subchondral base and a surface of the cartilage tissue prior to contacting the cartilage tissue with the surface of the subchondral base.

22. The method of claim 18 wherein the cartilage tissue comprises articular cartilage.

23. The method of claim 22, further comprising coupling the subchondral base to a positioning structure.

24. The method of claim 23, wherein the positioning structure comprises a non-trabecular metal.

25. The method of claim 23, wherein the positioning structure comprises a biocompatible polymer.

26. The method of claim 23, wherein the positioning structure comprises a screw, cylinder, plat, rod or washer.

27. The method of claim 18 wherein the subchondral base comprises at least one porous surface layer comprising a plurality of pores of median diameter from about 3 microns to about 800 microns and wherein the median diameter of the plurality of pores of the at least one porous surface layer is different from that of the plurality of pores of the subchondral base.

28. The method of claim 27 wherein the at least one porous surface layer comprises a plurality of pores of median pore diameter of about 100 microns to about 800 microns.

29. The method of claim 18, wherein the subchondral base comprises at least two surfaces, wherein a first surface comprises the trabecular metal having a plurality of pores there through, the pores having a median pore diameter of from about 100 microns to about 800 microns, and a second surface which is a cartilage-adherent surface.

30. The method of claim 18, wherein applying comprises attaching the cartilage tissue to a surface of the subchondral base with a fibrin adhesive.

31. The method of claim 18, wherein the subchondral base is cylindrical.

32. The method of claim 18, wherein the at least one trabecular metal comprises tantalum.

33. A method of forming an implant comprising cartilage and a subchondral base comprising:
    obtaining a subchondral base comprising at least one trabecular metal; and
    contacting the subchondral base with minced juvenile cartilage tissue from a human cadaveric donor.

34. The method of claim 33, further comprising coupling the cartilage tissue to a surface of the subchondral base.

35. The method of claim 34, wherein coupling comprises applying a cartilage adhesive to an interface between a surface of the subchondral base and a surface of the cartilage tissue prior to contacting the cartilage tissue with the subchondral base.

36. The method of claim 34, wherein coupling comprises attaching the cartilage tissue to a surface of the subchondral base with a fibrin adhesive.

37. The method of claim 33 wherein the implant further comprises at least one porous surface layer comprising a plurality of pores of median diameter from about 3 microns to about 800 microns wherein the median diameter of the plurality of pores of the at least one porous surface layer is different from that of the plurality of pores of the subchondral base.

38. The method of claim 33 wherein the subchondral base comprises at least two surfaces, wherein a first surface comprises trabecular metal comprising a plurality of pores having a median pore diameter of from about 100 microns to about 800 microns, and a second surface which is a cartilage-adherent surface comprising a plurality of pores having a median diameter from about 3 microns to about 20 microns.

39. The method of claim 38 wherein the cartilage-adherent surface comprises a resorbable polymer.

40. The method of claim 33, wherein the cartilage tissue comprises articular cartilage.

41. The method of claim 33, wherein the at least one trabecular metal comprises tantalum.

42. The method of claim 33, wherein the subchondral base is cylindrical.

* * * * *

UNITED STATES PATENT AND TRADEMARK OFFICE
CERTIFICATE OF CORRECTION

PATENT NO. : 8,480,757 B2  Page 1 of 1
APPLICATION NO. : 12/063291
DATED : July 9, 2013
INVENTOR(S) : Gage et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this
Eighth Day of September, 2015

Michelle K. Lee
*Director of the United States Patent and Trademark Office*